(12) United States Patent
Wickham et al.

(10) Patent No.: US 11,020,435 B2
(45) Date of Patent: Jun. 1, 2021

(54) FUNCTIONALIZED ERYTHROID CELLS

(71) Applicant: RUBIUS THERAPEUTICS, INC., Cambridge, MA (US)

(72) Inventors: Tom Wickham, Groton, MA (US); Tiffany F. Chen, Cambridge, MA (US); Xuqing Zhang, Quincy, MA (US); Carolyn Sayre, Somerville, MA (US); Jordi Mata-Fink, Happy Valley, OR (US); Sivan Elloul, Newton, MA (US); Billy Law, Brookline, MA (US); Lenka Hoffman, Malden, MA (US); Kristian Eric Teichert, Methuen, MA (US); Shamael Rabia Dastagir, Cambridge, MA (US)

(73) Assignee: Rubius Therapeutics, Inc., Cambridge, MA (US)

( * ) Notice: Subject to any disclaimer, the term of this patent is extended or adjusted under 35 U.S.C. 154(b) by 0 days.

(21) Appl. No.: 15/932,341

(22) Filed: Feb. 16, 2018

(65) Prior Publication Data
US 2018/0344770 A1    Dec. 6, 2018

Related U.S. Application Data

(60) Provisional application No. 62/460,589, filed on Feb. 17, 2017, provisional application No. 62/542,142, filed on Aug. 7, 2017.

(51) Int. Cl.
| | | |
|---|---|---|
| *A61K 35/18* | (2015.01) |
| *C12N 5/078* | (2010.01) |
| *A61K 39/385* | (2006.01) |
| *A61K 39/00* | (2006.01) |
| *A61K 38/17* | (2006.01) |

(52) U.S. Cl.
CPC ............ *A61K 35/18* (2013.01); *C12N 5/0641* (2013.01); *A61K 38/1774* (2013.01); *A61K 39/001* (2013.01); *A61K 39/385* (2013.01); *C12N 2510/00* (2013.01)

(58) Field of Classification Search
None
See application file for complete search history.

(56) References Cited

U.S. PATENT DOCUMENTS

| 8,501,478 B2 | 8/2013 | Reineke et al. |
| 8,673,293 B2 | 3/2014 | Martin et al. |
| 8,912,323 B2 | 12/2014 | Baker, Jr. et al. |
| 9,453,843 B2 | 9/2016 | Fontaine et al. |
| 9,517,291 B2 | 12/2016 | Belcheva et al. |
| 9,624,485 B2 | 4/2017 | Liu et al. |
| 9,644,180 B2 | 5/2017 | Kahvejian et al. |
| 10,301,593 B2 | 5/2019 | Kahvejian et al. |
| 10,301,594 B1 | 5/2019 | Kahvejian et al. |
| 10,329,531 B2 | 6/2019 | Kahvejian et al. |
| 10,344,263 B2 | 7/2019 | Kahvejian et al. |
| 10,456,421 B2 | 10/2019 | Kahvejian et al. |
| 10,517,897 B1 | 12/2019 | Kahvejian et al. |
| 10,557,119 B2 | 2/2020 | Kahvejian et al. |
| 2007/0243137 A1 | 10/2007 | Hainfeld |
| 2010/0040546 A1 | 2/2010 | Hyde |
| 2011/0070153 A1 | 3/2011 | Hyde et al. |
| 2015/0182588 A1 | 7/2015 | Kahvejian et al. |
| 2015/0306212 A1 | 10/2015 | Kahvejian et al. |
| 2016/0082046 A1 | 3/2016 | Lodish et al. |
| 2016/0097773 A1 | 4/2016 | Pasqual et al. |
| 2016/0122707 A1 | 5/2016 | Swee et al. |
| 2016/0257932 A1 | 9/2016 | Kahvejian et al. |
| 2017/0020926 A1 | 1/2017 | Mata-Fink et al. |
| 2017/0369843 A1 | 12/2017 | Kahvejian et al. |
| 2018/0030411 A1 | 2/2018 | Kahvejian et al. |
| 2018/0085402 A1 | 3/2018 | Kahvejian et al. |
| 2018/0119101 A1 | 5/2018 | Kahvejian et al. |
| 2018/0135012 A1 | 5/2018 | Mata-Fink et al. |
| 2018/0153989 A1 | 6/2018 | Kahvejian et al. |
| 2018/0187153 A1 | 7/2018 | Kahvejian et al. |
| 2018/0187154 A1 | 7/2018 | Kahvejian et al. |
| 2018/0187155 A1 | 7/2018 | Kahvejian et al. |
| 2018/0193385 A1 | 7/2018 | Kahvejian et al. |
| 2018/0208897 A1 | 7/2018 | Kahvejian et al. |
| 2018/0216067 A1 | 8/2018 | Kahvejian et al. |
| 2018/0265847 A1 | 9/2018 | Kahvejian et al. |
| 2018/0271910 A1 | 9/2018 | Mata-Fink et al. |
| 2019/0062788 A1 | 2/2019 | Harandi et al. |
| 2019/0083540 A1 | 3/2019 | Kahvejian et al. |
| 2019/0144827 A1 | 5/2019 | Kahvejian et al. |
| 2019/0160102 A1 | 5/2019 | Hoffman et al. |

(Continued)

FOREIGN PATENT DOCUMENTS

| WO | WO-2009137629 A2 * | 11/2009 | ........... C12N 5/0641 |
| WO | 2013138314 A1 | 9/2013 | |

(Continued)

OTHER PUBLICATIONS

Mani, et al. (2012) "Highly efficient binding of paramagnetic beads bioconjugated with 100,000 or more antibodies to protein-coated surfaces", Analytical Chemistry, 84: 10485-91. (Year: 2012).*
https://clickchemistrytools.com/product/dbco-peg4-nhs-ester/, Author unknown, published by Click Chemistry Tools, Scottsdale, AZ, 2012, 2 pages long. (Year: 2012).*
https://clickchemistrytools.com/product/6-azidohexanoic-acid-acid-sulfo-nhs-ester/, Author unknown, published by Click Chemistry Tools, Scottsdale, AZ, 2012, 2 pages long. (Year: 2012).*
Muzykantov (2010) "Drug delivery by red blood cells: vascular carriers designed by Mother Nature", Expert Opinion in Drug Delivery, 7(4): 403-27, provided by way of NIH Public Access Manuscript, 40 pages long.*

(Continued)

*Primary Examiner* — Robert M Kelly
(74) *Attorney, Agent, or Firm* — Fish & Richardson P.C.

(57) ABSTRACT

Described herein are novel preparations of functionalized erythroid cells and related compositions, reagents, and methods for use in human pharmaceutical and veterinary applications.

44 Claims, 9 Drawing Sheets
Specification includes a Sequence Listing.

(56) References Cited

U.S. PATENT DOCUMENTS

| | | |
|---|---|---|
| 2019/0161730 A1 | 5/2019 | Kahvejian et al. |
| 2019/0201548 A1 | 7/2019 | Kahvejian et al. |
| 2019/0247440 A1 | 8/2019 | Mata-Fink et al. |
| 2019/0264177 A1 | 8/2019 | Kahvejian et al. |
| 2019/0309261 A1 | 10/2019 | Kahvejian et al. |
| 2019/0309262 A1 | 10/2019 | Kahvejian et al. |
| 2019/0316090 A1 | 10/2019 | Kahvejian et al. |
| 2019/0316091 A1 | 10/2019 | Kahvejian et al. |
| 2019/0330591 A1 | 10/2019 | Yu et al. |
| 2019/0376034 A1 | 12/2019 | Kahvejian et al. |
| 2019/0388473 A1 | 12/2019 | Mata-Fink et al. |
| 2020/0002674 A1 | 1/2020 | Kahvejian et al. |
| 2020/0016209 A1 | 1/2020 | Kahvejian et al. |

FOREIGN PATENT DOCUMENTS

| | | |
|---|---|---|
| WO | 2014183066 A2 | 11/2014 |
| WO | 2014183071 A2 | 11/2014 |
| WO | WO 2015/015302 | 2/2015 |
| WO | WO 2015/073587 | 5/2015 |
| WO | WO 2015/153102 | 10/2015 |
| WO | 2016145031 A1 | 9/2016 |
| WO | WO 2016/183482 | 11/2016 |
| WO | 2017152077 A1 | 9/2017 |
| WO | 2018009838 A1 | 1/2018 |

OTHER PUBLICATIONS

[No Author Listed] "Click Chemistry Azide-Alkyne Cycloaddition," retrieved from the internet, organic-chemistry.org/namedreations/click-chemistry.shtm, last accessed Apr. 21, 2017.

Baskin et al., "Copper-free click chemistry for dynamic in vivo imaging," PNAS (2007) vol. 104, No. 43, pp. 16793-13797.

Becer et al., "Click Chemistry beyond Metal-Catalyzed Cycloaddition," Angew Chem Int Ed (2009) vol. 48, pp. 4900-4908.

Beck et al., "Strategies and challenges for the next generation of antibody-drug conjugates," Nat Rev Drug Discovery (2017) doi:10.1038/nrd.2016.268, 23 pages.

Chen et al., "Site-specific labeling of cell surface proteins with biophysical probes using biotin ligase," Nature Methods (2005) vol. 2, No. 2, pp. 99-104.

Hall et al "Identification of Peptide Ligands Facilitation Nanoparticle Attachment to Erythrocytes" Biotechnol. Prog. (2007) vol. 23, pp. 749-754.

Hein et al. "Click Chemistry, a Powerful Tool for Pharmaceutical Sciences" Pharmaceutical Research (2008) vol. 25, No. 10, pp. 2216-2230.

Hong et al. "Labeling Live Cells by Copper-Catalyzed Alkyne-Azide Click Chemistry" Bioconjugate Chem. (2010) vol. 21, pp. 1912-1916.

Hong et al., "Labeling Live Cells by Copper-Catalyzed Alkyne-Azide Click Chemistry," Bioconj Chem (2010) vol. 21, No. 10, pp. 1912-1916.

International Search Report and Written Opinion for International Application No. PCT/US2018/000042 dated Jun. 20, 2018.

McKay et al., "Click Chemistry in Complex Mixtures: Bioorthogonal Bioconjugation," Chemistry & Biology (2014) vol. 21, pp. 1075-1101.

Mongis et al., "Coupling of Immunostimulants to Live Cells through Metabolic Glycoengineering and Bioorthogonal Click Chemistry," Bioconj Chem (2017) vol. 28, pp. 1151-1165.

Muzykantov et al. "Drug delivery by red blood cells: vascular carriers designed by Mother Nature" Expert Opin. Drug Deliv. (2010) vol. 7, No. 4, pp. 403-427.

Nikic et al., "Labeling proteins on live mammalian cells using click chemistry," Nature Protocols (2015) vol. 10, No. 5, pp. 780-791.

Shi et al. "Engineered red blood cells as carriers for systemic delivery of a wide array of functional probes" PNAS (2014) vol. 111, No. 28, pp. 10131-10136.

Smirnov et al. "Carrier-directed targeting of liposomes and erythrocytes to denuded areas of vessel wall" Proc. Natl. Acad. Sci. (1986) vol. 83, pp. 6603-6607.

Wang et al., "In situ activation of platelets with checkpoint inhibitors for post-surgical cancer immunotherapy," Nature Biomedical Engineering (2017) doi:10.1038/s41551-016-0011, 10 pages.

Zhang et al. "Applications of Azide-Based Bioorthogonal Click Chemistry in Glycobiology" Molecules (2013) vol. 18, pp. 7145-7159.

Agarwal et al., "Blood group phenotype frequencies in blood donors from a tertiary care hospital in North India," Blood Res. 48(1):51-54, 2013.

Al-Lazikani et al., "Standard conformations for the canonical structures of immunoglobulins," J. Mol. Biol. 273(4):927-948, 1997.

Carlmark et al., "New methodologies in the construction of dendritic materials," Chem. Soc. Rev. 38(2):352-362, 2009.

Clickchemistrytools.com, [online], "Click Chemisty Toolbox," 2009, retrieved on Oct. 12, 2020, retrieved from URL<https://clickchemistrytools.com/>, 2 pages.

De Bank et al, "Surface engineering of living myoblasts via selective periodate oxidation," Biotechnol. Bioeng. 81(7):800-808, 2003.

Huang et al, "Extensive Ex Vivo Expansion of Functional Human Erythroid Precursors Established From Umbilical Cord Blood Cells by Defined Factors,"Mol. Ther. 22(2):451-63, 2014.

IL Office Action in Israeli Appln. No. 268359, dated Jun. 14, 2020, 5 pages (with English Translation).

Kolb et al., "Click Chemistry: Diverse Chemical Function from a Few Good Reactions," Angewandte Chemie Intl. Ed. 40:2004-2011, 2001.

Liu et al., "Bacterial glycosidases for the production of universal red blood cells," Nat. Biotech. 25(4):454-464, 2007.

Migliaccio et al., "Blood in a dish: In vitro synthesis of red blood cells," Drug Discov. Today Dis. Mech. 8(1-2)e3-e8, 2011.

Mitra et al., "Blood groups systems," Indian J. Anaesth. 58(5):524-528, 2014.

PCT International Preliminary Report on Patentability in International Appln. No. PCT/US2018/000042, dated Aug. 20, 2019, 8 pages.

Sun et al., "Surface-Engineering of Red Blood Cells as Artificial Antigen Presenting Cells Promising for Cancer Immunotherapy," Adv. Sci. News, 13:1701864, 8 pages, 2017.

Tirapu et al., "Improving efficacy of interleukin-12-transfected dendritic cells injected into murine colon cancer with anti-CD137 monoclonal antibodies and alloantigens," Int. J. Cancer 110(1):51-60, 2004.

Tomoe et al., "Peptidotriazoles on Solid Phase: [1,2,3]-Triazoles by Regiospecitie Copper(I) , Catalyzed 1,3-Dipolar Cycloadditions of Terminal Alkynes to Azides," J. Org. Chem. 67(9)3057-64, 2002.

\* cited by examiner

Exo(BCN)-Lys

SEQUENCE LISTING

<160> NUMBER OF SEQ ID NOS: 64

<210> SEQ ID NO 1
<211> LENGTH: 5
<212> TYPE: PRT
<213> ORGANISM: Unknown
<220> FEATURE:
<223> OTHER INFORMATION: Description of Unknown:
    Sortase recognition site sequence
<220> FEATURE:
<221> NAME/KEY: MOD_RES
<222> LOCATION: (3)..(3)
<223> OTHER INFORMATION: Any amino acid
<220> FEATURE:
<223> OTHER INFORMATION: See specification as filed for detailed
    description of substitutions and preferred embodiments

<400> SEQUENCE: 1

```
Leu Pro Xaa Thr Gly
1               5

<210> SEQ ID NO 2
<211> LENGTH: 6
<212> TYPE: PRT
<213> ORGANISM: Unknown
<220> FEATURE:
<223> OTHER INFORMATION: Description of Unknown:
      Sortase recognition site sequence
<220> FEATURE:
<221> NAME/KEY: MOD_RES
<222> LOCATION: (3)..(3)
<223> OTHER INFORMATION: Any amino acid

<400> SEQUENCE: 2

Leu Pro Xaa Thr Gly Gly
1               5

<210> SEQ ID NO 3
<211> LENGTH: 205
<212> TYPE: PRT
<213> ORGANISM: Unknown
<220> FEATURE:
<223> OTHER INFORMATION: Description of Unknown:
      4-1BBL sequence

<400> SEQUENCE: 3

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
            20                  25                  30

Ala Gly Leu Leu Asp Leu Arg Gln Gly Met Phe Ala Gln Leu Val Ala
        35                  40                  45

Gln Asn Val Leu Leu Ile Asp Gly Pro Leu Ser Trp Tyr Ser Asp Pro
    50                  55                  60

Gly Leu Ala Gly Val Ser Leu Thr Gly Gly Leu Ser Tyr Lys Glu Asp
65                  70                  75                  80

Thr Lys Glu Leu Val Val Ala Lys Ala Gly Val Tyr Tyr Val Phe Phe
                85                  90                  95

Gln Leu Glu Leu Arg Arg Val Val Ala Gly Glu Gly Ser Gly Ser Val
            100                 105                 110

Ser Leu Ala Leu His Leu Gln Pro Leu Arg Ser Ala Ala Gly Ala Ala
        115                 120                 125

Ala Leu Ala Leu Thr Val Asp Leu Pro Pro Ala Ser Ser Glu Ala Arg
    130                 135                 140

Asn Ser Ala Phe Gly Phe Gln Gly Arg Leu Leu His Leu Ser Ala Gly
145                 150                 155                 160

Gln Arg Leu Gly Val His Leu His Thr Glu Ala Arg Ala Arg His Ala
                165                 170                 175

Trp Gln Leu Thr Gln Gly Ala Thr Val Leu Gly Leu Phe Arg Val Thr
            180                 185                 190

Pro Glu Ile Pro Ala Gly Leu Pro Ser Pro Arg Ser Glu
        195                 200                 205

<210> SEQ ID NO 4
<211> LENGTH: 451
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 4

```
Gln Val Gln Leu Gln Gln Pro Gly Ala Glu Leu Val Lys Pro Gly Ala
  1               5                  10                  15
Ser Val Lys Met Ser Cys Lys Ala Ser Gly Tyr Thr Phe Thr Ser Tyr
             20                  25                  30
Asn Met His Trp Val Lys Gln Thr Pro Gly Arg Gly Leu Glu Trp Ile
         35                  40                  45
Gly Ala Ile Tyr Pro Gly Asn Gly Asp Thr Ser Tyr Asn Gln Lys Phe
     50                  55                  60
Lys Gly Lys Ala Thr Leu Thr Ala Asp Lys Ser Ser Thr Ala Tyr
 65                  70                  75                  80
Met Gln Leu Ser Ser Leu Thr Ser Glu Asp Ser Ala Val Tyr Tyr Cys
                 85                  90                  95
Ala Arg Ser Thr Tyr Tyr Gly Gly Asp Trp Tyr Phe Asn Val Trp Gly
            100                 105                 110
Ala Gly Thr Thr Val Thr Val Ser Ala Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Ala Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
```

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 5
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 6
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
        50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
            115                 120                 125

Thr Arg Arg Arg Ser Asn Thr Leu Ser Ser Pro Asn Ser Lys Asn Glu
        130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
        210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 7
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
        50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
                100                 105                 110

Leu Val Arg Glu Arg Gly Pro Gln Arg Val Ala Ala His Ile Thr Gly
            115                 120                 125

Thr Arg Gly Arg Ser Asn Thr Leu Ser Ser Pro Asn Ser Lys Asn Glu
        130                 135                 140

Lys Ala Leu Gly Arg Lys Ile Asn Ser Trp Glu Ser Ser Arg Arg Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 8
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Arg Arg Ser Asn Thr Leu Ser Ser Pro Asn Ser Lys Asn Glu
    130                 135                 140

Lys Ala Leu Gly Ile Lys Ile Asn Ser Trp Glu Ser Ser Arg Arg Gly
145                 150                 155                 160

His Ser Phe Leu Ser Asn Leu His Leu Arg Asn Gly Glu Leu Val Ile

```
                    165                 170                 175
His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
            195                 200                 205

Tyr Ile Tyr Lys Tyr Thr Asp Tyr Pro Asp Pro Ile Leu Leu Met Lys
        210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
            245                 250                 255

Phe Val Ser Val Thr Asn Glu His Leu Ile Asp Met Asp His Glu Ala
            260                 265                 270

Ser Phe Phe Gly Ala Phe Leu Val Gly
            275                 280

<210> SEQ ID NO 9
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
            85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
            165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
            195                 200                 205

Tyr Ile Tyr Lys Tyr Thr Ser Tyr Pro Asp Pro Ile Leu Leu Met Lys
        210                 215                 220

Ser Ala Arg Asn Ser Cys Trp Ser Lys Asp Ala Glu Tyr Gly Leu Tyr
225                 230                 235                 240
```

```
Ser Ile Tyr Gln Gly Gly Ile Phe Glu Leu Lys Glu Asn Asp Arg Ile
            245                 250                 255

Phe Val Ser Val Thr Asn Glu His Leu Ile Asp Met His His Glu Ala
        260                 265                 270

Ser Phe Phe Gly Ala Phe Leu Val Gly
        275                 280

<210> SEQ ID NO 10
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Arg Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met His His Glu Ala
            260                 265                 270

Ser Phe Phe Gly Ala Phe Leu Val Gly
        275                 280

<210> SEQ ID NO 11
<211> LENGTH: 238
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 11

Val Gln Leu Val Glu Ser Gly Gly Gly Leu Val Gln Pro Gly Ser
1               5                   10                  15

Leu Arg Leu Ser Cys Ala Ala Ser Gly Phe Thr Phe Ser Asp Ser Trp
            20                  25                  30

Ile His Trp Val Arg Gln Ala Pro Gly Lys Gly Leu Glu Trp Val Ala
        35                  40                  45

Trp Ile Ser Pro Tyr Gly Gly Ser Thr Tyr Tyr Ala Asp Ser Val Lys
50                  55                  60

Gly Arg Phe Thr Ile Ser Ala Asp Thr Ser Lys Asn Thr Ala Tyr Leu
65                  70                  75                  80

Gln Met Asn Ser Leu Arg Ala Glu Asp Thr Ala Val Tyr Tyr Cys Ala
                85                  90                  95

Arg Arg His Trp Pro Gly Gly Phe Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Ile Gln Met Thr Gln Ser Pro Ser Ser Leu Ser Ala
130                 135                 140

Ser Val Gly Asp Arg Val Thr Ile Thr Cys Arg Ala Ser Gln Asp Val
145                 150                 155                 160

Ser Thr Ala Val Ala Trp Tyr Gln Gln Lys Pro Gly Lys Ala Pro Lys
                165                 170                 175

Leu Leu Ile Tyr Ser Ala Ser Phe Leu Tyr Ser Gly Val Pro Ser Arg
            180                 185                 190

Phe Ser Gly Ser Gly Ser Gly Thr Asp Phe Thr Leu Thr Ile Ser Ser
        195                 200                 205

Leu Gln Pro Glu Asp Phe Ala Thr Tyr Tyr Cys Gln Gln Tyr Leu Tyr
    210                 215                 220

His Pro Ala Thr Phe Gly Gln Gly Thr Lys Val Glu Ile Lys
225                 230                 235

<210> SEQ ID NO 12
<211> LENGTH: 567
<212> TYPE: PRT
<213> ORGANISM: Unknown
<220> FEATURE:
<223> OTHER INFORMATION: Description of Unknown:
      PAL sequence

<400> SEQUENCE: 12

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95
```

```
Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
            115                 120                 125

Ala Asn Ser His Met Arg Gly Ala Ser Gly Ile Arg Leu Glu Leu Ile
            130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
            195                 200                 205

Ser Pro Leu Thr Leu Leu Pro Lys Glu Gly Leu Ala Met Met Asn Gly
            210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
            275                 280                 285

Ala Asn Ser Gln Leu Val Arg Asp Glu Leu Asp Gly Lys His Asp Tyr
            290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
            355                 360                 365

Gly Met Gly Met Asp His Leu Arg Tyr Tyr Ile Gly Leu Leu Ala Lys
            370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
            435                 440                 445

Gln Phe Asn Gln Asn Ile Asn Ser Gln Gly Tyr Thr Ser Ala Thr Leu
            450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510
```

Ser Ala Val Arg His Val Val Gly Gln Lys Pro Thr Ser Asp Arg Pro
515 520 525

Tyr Ile Trp Asn Asp Asn Glu Gln Gly Leu Asp Glu His Ile Ala Arg
530 535 540

Ile Ser Ala Asp Ile Ala Ala Gly Gly Val Ile Val Gln Ala Val Gln
545 550 555 560

Asp Ile Leu Pro Cys Leu His
565

<210> SEQ ID NO 13
<211> LENGTH: 328
<212> TYPE: PRT
<213> ORGANISM: Unknown
<220> FEATURE:
<223> OTHER INFORMATION: Description of Unknown:
Y vb Asparaginase sequence

<400> SEQUENCE: 13

Met Ala Asp Lys Leu Pro Asn Ile Val Ile Leu Ala Thr Gly Gly Thr
1 5 10 15

Ile Ala Gly Ser Ala Ala Thr Gly Thr Gln Thr Thr Gly Tyr Lys Ala
20 25 30

Gly Ala Leu Gly Val Asp Thr Leu Ile Asn Ala Val Pro Glu Val Lys
35 40 45

Lys Leu Ala Asn Val Lys Gly Glu Gln Phe Ser Asn Met Ala Ser Glu
50 55 60

Asn Met Thr Gly Asp Val Val Leu Lys Leu Ser Gln Arg Val Asn Glu
65 70 75 80

Leu Leu Ala Arg Asp Asp Val Asp Gly Val Val Ile Thr His Gly Thr
85 90 95

Asp Thr Val Glu Glu Ser Ala Tyr Phe Leu His Leu Thr Val Lys Ser
100 105 110

Asp Lys Pro Val Val Phe Val Ala Ala Met Arg Pro Ala Thr Ala Ile
115 120 125

Ser Ala Asp Gly Pro Met Asn Leu Leu Glu Ala Val Arg Val Ala Gly
130 135 140

Asp Lys Gln Ser Arg Gly Arg Gly Val Met Val Val Leu Asn Asp Arg
145 150 155 160

Ile Gly Ser Ala Arg Tyr Ile Thr Lys Thr Asn Ala Ser Thr Leu Asp
165 170 175

Thr Phe Lys Ala Asn Glu Glu Gly Tyr Leu Gly Val Ile Ile Gly Asn
180 185 190

Arg Ile Tyr Tyr Gln Asn Arg Ile Asp Lys Leu His Thr Thr Arg Ser
195 200 205

Val Phe Asp Val Arg Gly Leu Thr Ser Leu Pro Lys Val Asp Ile Leu
210 215 220

Tyr Gly Tyr Gln Asp Asp Pro Glu Tyr Leu Tyr Asp Ala Ala Ile Gln
225 230 235 240

His Gly Val Lys Gly Ile Val Tyr Ala Gly Met Gly Ala Gly Ser Val
245 250 255

Ser Val Arg Gly Ile Ala Gly Met Arg Lys Ala Met Glu Lys Gly Val
260 265 270

Val Val Ile Arg Ser Thr Arg Thr Gly Asn Gly Ile Val Pro Pro Asp
275 280 285

Glu Glu Leu Pro Gly Leu Val Ser Asp Ser Leu Asn Pro Ala His Ala
290 295 300

Arg Ile Leu Leu Met Leu Ala Leu Thr Arg Thr Ser Asp Pro Lys Val
305                 310                 315                 320

Ile Gln Glu Tyr Phe His Thr Tyr
                325

<210> SEQ ID NO 14
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Ser Tyr
                20                  25                  30

Trp Met His Trp Val Arg Gln Ala Pro Gly Gln Arg Leu Glu Trp Ile
            35                  40                  45

Gly Glu Ile Asp Pro Ser Glu Ser Asn Thr Asn Tyr Asn Gln Lys Phe
    50                  55                  60

Lys Gly Arg Val Thr Leu Thr Val Asp Ile Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asp Gly Trp Asp Tyr Ala Ile Asp Tyr Trp Gly
            100                 105                 110

Gln Gly Thr Leu Val Thr Val Ser Ser
        115                 120

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Ala Lys Ser
                20                  25                  30

Tyr Gly Asn Thr Tyr Leu Ser Trp Tyr Leu Gln Lys Pro Gly Gln Ser
            35                  40                  45

Pro Gln Leu Leu Ile Tyr Gly Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Gly
                85                  90                  95

Thr His Gln Pro Tyr Thr Phe Gly Gln Gly Thr Lys Val Glu Ile Lys
            100                 105                 110

<210> SEQ ID NO 16
<211> LENGTH: 160
<212> TYPE: PRT
<213> ORGANISM: Homo sapiens -continued

<400> SEQUENCE: 16

```
Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
130                 135                 140

Ile Phe Ile Asn Tyr Ile Glu Ala Tyr Met Thr Met Lys Ile Arg Asn
145                 150                 155                 160
```

<210> SEQ ID NO 17
<211> LENGTH: 448
<212> TYPE: PRT
<213> ORGANISM: Unknown
<220> FEATURE:
<223> OTHER INFORMATION: Description of Unknown:
      Clotting Factor X sequence

<400> SEQUENCE: 17

```
Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190
```

Thr Arg Ile Val Gly Gly Gln Glu Cys Lys Asp Gly Glu Cys Pro Trp
            195                 200                 205

Gln Ala Leu Leu Ile Asn Glu Glu Asn Glu Gly Phe Cys Gly Gly Thr
        210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285

Lys Thr Pro Ile Thr Phe Arg Met Asn Val Ala Pro Ala Cys Leu Pro
290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
        355                 360                 365

Thr Lys Gln Glu Asp Ala Cys Gln Gly Asp Ser Gly Gly Pro His Val
370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
        435                 440                 445

<210> SEQ ID NO 18
<211> LENGTH: 5
<212> TYPE: PRT
<213> ORGANISM: Unknown
<220> FEATURE:
<223> OTHER INFORMATION: Description of Unknown:
      Sortase recognition site sequence
<220> FEATURE:
<221> NAME/KEY: MOD_RES
<222> LOCATION: (3)..(3)
<223> OTHER INFORMATION: Any amino acid

<400> SEQUENCE: 18

Leu Pro Xaa Thr Ala
1               5

<210> SEQ ID NO 19
<211> LENGTH: 5
<212> TYPE: PRT
<213> ORGANISM: Unknown
<220> FEATURE:
<223> OTHER INFORMATION: Description of Unknown:
      Sortase recognition site sequence
<220> FEATURE:
<221> NAME/KEY: MOD_RES
<222> LOCATION: (3)..(3)
<223> OTHER INFORMATION: Asp, Glu, Ala, Asn, Gln, Lys or Arg

```
<400> SEQUENCE: 19

Leu Pro Xaa Thr Gly
1               5

<210> SEQ ID NO 20
<211> LENGTH: 5
<212> TYPE: PRT
<213> ORGANISM: Unknown
<220> FEATURE:
<223> OTHER INFORMATION: Description of Unknown:
      Sortase recognition site sequence
<220> FEATURE:
<221> NAME/KEY: MOD_RES
<222> LOCATION: (3)..(3)
<223> OTHER INFORMATION: Lys, Glu, Asn, Gln or Ala

<400> SEQUENCE: 20

Leu Pro Xaa Thr Gly
1               5

<210> SEQ ID NO 21
<211> LENGTH: 5
<212> TYPE: PRT
<213> ORGANISM: Unknown
<220> FEATURE:
<223> OTHER INFORMATION: Description of Unknown:
      Sortase recognition site sequence
<220> FEATURE:
<221> NAME/KEY: MOD_RES
<222> LOCATION: (3)..(3)
<223> OTHER INFORMATION: Lys, Ser, Glu, Leu, Ala or Asn

<400> SEQUENCE: 21

Leu Pro Xaa Thr Gly
1               5

<210> SEQ ID NO 22
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 22

Leu Pro Lys Thr Gly
1               5

<210> SEQ ID NO 23
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 23

Leu Pro Ile Thr Gly
1               5

<210> SEQ ID NO 24
<211> LENGTH: 5
<212> TYPE: PRT
<213> ORGANISM: Unknown
<220> FEATURE:
<223> OTHER INFORMATION: Description of Unknown:
      Sortase recognition site sequence
```

```
<400> SEQUENCE: 24

Leu Pro Asp Thr Ala
1               5

<210> SEQ ID NO 25
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 25

Ser Pro Lys Thr Gly
1               5

<210> SEQ ID NO 26
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 26

Leu Ala Glu Thr Gly
1               5

<210> SEQ ID NO 27
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 27

Leu Ala Ala Thr Gly
1               5

<210> SEQ ID NO 28
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 28

Leu Ala His Thr Gly
1               5

<210> SEQ ID NO 29
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 29

Leu Ala Ser Thr Gly
1               5

<210> SEQ ID NO 30
<211> LENGTH: 5
<212> TYPE: PRT
```

```
<213> ORGANISM: Unknown
<220> FEATURE:
<223> OTHER INFORMATION: Description of Unknown:
      Sortase recognition site sequence

<400> SEQUENCE: 30

Leu Pro Leu Thr Gly
1               5

<210> SEQ ID NO 31
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 31

Leu Ser Arg Thr Gly
1               5

<210> SEQ ID NO 32
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 32

Leu Pro Glu Thr Gly
1               5

<210> SEQ ID NO 33
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 33

Val Pro Asp Thr Gly
1               5

<210> SEQ ID NO 34
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 34

Ile Pro Gln Thr Gly
1               5

<210> SEQ ID NO 35
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 35

Tyr Pro Arg Arg Gly
1               5
```

<210> SEQ ID NO 36
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 36

Leu Pro Met Thr Gly
1               5

<210> SEQ ID NO 37
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 37

Leu Ala Phe Thr Gly
1               5

<210> SEQ ID NO 38
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 38

Leu Pro Gln Thr Ser
1               5

<210> SEQ ID NO 39
<211> LENGTH: 4
<212> TYPE: PRT
<213> ORGANISM: Unknown
<220> FEATURE:
<223> OTHER INFORMATION: Description of Unknown:
      Sortase recognition site sequence

<400> SEQUENCE: 39

Asn Pro Gln Ser
1

<210> SEQ ID NO 40
<211> LENGTH: 4
<212> TYPE: PRT
<213> ORGANISM: Unknown
<220> FEATURE:
<223> OTHER INFORMATION: Description of Unknown:
      Sortase recognition site sequence

<400> SEQUENCE: 40

Leu Pro Ser Thr
1

<210> SEQ ID NO 41
<211> LENGTH: 4
<212> TYPE: PRT
<213> ORGANISM: Unknown
<220> FEATURE:
<223> OTHER INFORMATION: Description of Unknown:
      Sortase recognition site sequence

```
<400> SEQUENCE: 41

Asn Ser Lys Thr
1

<210> SEQ ID NO 42
<211> LENGTH: 4
<212> TYPE: PRT
<213> ORGANISM: Unknown
<220> FEATURE:
<223> OTHER INFORMATION: Description of Unknown:
      Sortase recognition site sequence

<400> SEQUENCE: 42

Asn Pro Gln Thr
1

<210> SEQ ID NO 43
<211> LENGTH: 4
<212> TYPE: PRT
<213> ORGANISM: Unknown
<220> FEATURE:
<223> OTHER INFORMATION: Description of Unknown:
      Sortase recognition site sequence

<400> SEQUENCE: 43

Asn Ala Lys Thr
1

<210> SEQ ID NO 44
<211> LENGTH: 4
<212> TYPE: PRT
<213> ORGANISM: Unknown
<220> FEATURE:
<223> OTHER INFORMATION: Description of Unknown:
      Sortase recognition site sequence

<400> SEQUENCE: 44

Leu Pro Ile Thr
1

<210> SEQ ID NO 45
<211> LENGTH: 4
<212> TYPE: PRT
<213> ORGANISM: Unknown
<220> FEATURE:
<223> OTHER INFORMATION: Description of Unknown:
      Sortase recognition site sequence

<400> SEQUENCE: 45

Leu Ala Glu Thr
1

<210> SEQ ID NO 46
<211> LENGTH: 5
<212> TYPE: PRT
<213> ORGANISM: Unknown
<220> FEATURE:
<223> OTHER INFORMATION: Description of Unknown:
      Sortase recognition site sequence
<220> FEATURE:
<221> NAME/KEY: MOD_RES
<222> LOCATION: (3)..(3)
<223> OTHER INFORMATION: Any amino acid

<400> SEQUENCE: 46

Leu Pro Xaa Ala Gly
1               5
```

```
<210> SEQ ID NO 47
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 47

Leu Pro Asn Ala Gly
1               5

<210> SEQ ID NO 48
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 48

Leu Pro Asn Thr Ala
1               5

<210> SEQ ID NO 49
<211> LENGTH: 5
<212> TYPE: PRT
<213> ORGANISM: Unknown
<220> FEATURE:
<223> OTHER INFORMATION: Description of Unknown:
      Sortase recognition site sequence
<220> FEATURE:
<221> NAME/KEY: MOD_RES
<222> LOCATION: (3)..(3)
<223> OTHER INFORMATION: Any amino acid

<400> SEQUENCE: 49

Leu Gly Xaa Thr Gly
1               5

<210> SEQ ID NO 50
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 50

Leu Gly Ala Thr Gly
1               5

<210> SEQ ID NO 51
<211> LENGTH: 5
<212> TYPE: PRT
<213> ORGANISM: Unknown
<220> FEATURE:
<223> OTHER INFORMATION: Description of Unknown:
      Sortase recognition site sequence
<220> FEATURE:
<221> NAME/KEY: MOD_RES
<222> LOCATION: (3)..(3)
<223> OTHER INFORMATION: Any amino acid

<400> SEQUENCE: 51

Ile Pro Xaa Thr Gly
1               5
```

```
<210> SEQ ID NO 52
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 52

Ile Pro Asn Thr Gly
1               5

<210> SEQ ID NO 53
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 53

Ile Pro Glu Thr Gly
1               5

<210> SEQ ID NO 54
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 54

Asn Pro Gln Thr Asn
1               5

<210> SEQ ID NO 55
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 55

Asn Pro Lys Thr Gly
1               5

<210> SEQ ID NO 56
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 56

Asn Ser Lys Thr Ala
1               5

<210> SEQ ID NO 57
<211> LENGTH: 5
<212> TYPE: PRT
<213> ORGANISM: Unknown
<220> FEATURE:
<223> OTHER INFORMATION: Description of Unknown:
      Sortase recognition site sequence
```

```
<400> SEQUENCE: 57

Asn Pro Gln Thr Gly
1               5

<210> SEQ ID NO 58
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 58

Asn Ala Lys Thr Asn
1               5

<210> SEQ ID NO 59
<211> LENGTH: 5
<212> TYPE: PRT
<213> ORGANISM: Unknown
<220> FEATURE:
<223> OTHER INFORMATION: Description of Unknown:
      Sortase recognition site sequence

<400> SEQUENCE: 59

Asn Pro Gln Ser Ser
1               5

<210> SEQ ID NO 60
<211> LENGTH: 5
<212> TYPE: PRT
<213> ORGANISM: Unknown
<220> FEATURE:
<223> OTHER INFORMATION: Description of Unknown:
      Sortase recognition site sequence
<220> FEATURE:
<221> NAME/KEY: MOD_RES
<222> LOCATION: (3)..(3)
<223> OTHER INFORMATION: Glu, Ala, Ser or His

<400> SEQUENCE: 60

Asn Ala Xaa Thr Gly
1               5

<210> SEQ ID NO 61
<211> LENGTH: 5
<212> TYPE: PRT
<213> ORGANISM: Unknown
<220> FEATURE:
<223> OTHER INFORMATION: Description of Unknown:
      Sortase recognition site sequence
<220> FEATURE:
<221> NAME/KEY: MOD_RES
<222> LOCATION: (3)..(3)
<223> OTHER INFORMATION: Any amino acid

<400> SEQUENCE: 61

Leu Ala Xaa Thr Gly
1               5

<210> SEQ ID NO 62
<211> LENGTH: 6
<212> TYPE: PRT
<213> ORGANISM: Unknown
<220> FEATURE:
<223> OTHER INFORMATION: Description of Unknown:
      Sortase recognition site sequence

<400> SEQUENCE: 62
```

```
Gln Val Pro Thr Gly Val
1               5

<210> SEQ ID NO 63
<211> LENGTH: 6
<212> TYPE: PRT
<213> ORGANISM: Unknown
<220> FEATURE:
<223> OTHER INFORMATION: Description of Unknown:
      Sortase recognition site sequence
<220> FEATURE:
<221> NAME/KEY: MOD_RES
<222> LOCATION: (3)..(3)
<223> OTHER INFORMATION: Gln or Lys
<220> FEATURE:
<221> NAME/KEY: MOD_RES
<222> LOCATION: (5)..(5)
<223> OTHER INFORMATION: Ala or Ser

<400> SEQUENCE: 63

Leu Pro Xaa Thr Xaa Thr
1               5

<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Phe Cys Pro Phe
1
```

FUNCTIONALIZED ERYTHROID CELLS

RELATED APPLICATIONS

This application claims priority to U.S. Ser. No. 62/460,589 filed Feb. 17, 2017 and U.S. Ser. No. 62/542,142 filed Aug. 7, 2017, the contents of each of which are incorporated herein by reference in their entirety.

SEQUENCE LISTING

The instant application contains a Sequence Listing which has been filed electronically in ASCII format and is hereby incorporated by reference in its entirety. Said ASCII copy, created on Feb. 15, 2018, is named R2081-702110_SL.txt and is 48,634 bytes in size.

BACKGROUND

Erythroid cells such as red blood cells can be engineered to express a wide variety of exogenous therapeutic proteins in order to treat a number of different diseases, as described in WO2015/073587 (Rubius Therapeutics, Inc.). This engineering can involve introducing a transgene into erythroid cell precursors, and then inducing the precursors to differentiate and express the transgene. However, some proteins are difficult to express, e.g., because they require a post-translational modification or because they compromise the growth or function of a host cell. There exists a need for improved methods of producing cells comprising such proteins.

SUMMARY OF THE INVENTION

Described herein are novel preparations of functionalized erythroid cells and related compositions, reagents, and methods that have advantageous and surprising qualities for use in human pharmaceutical and veterinary applications. For example, methods and compositions disclosed herein provide for functionalized erythroid cells having optimized yield, purity, stability, viability, immunogenicity, function, integrity, and/or biological function for use in therapeutic applications. The functionalized erythroid cells described herein are particularly well suited for delivery of agents to the surface of the cells or for complex or difficult to express agents, e.g., polypeptides, e.g., multimeric polypeptides; large polypeptides; agents derivatized in vitro, e.g., polypeptides; agents that may be toxic to, or which cannot be expressed efficiently in, the erythroid cells. The agent may also be a lipid, nucleic acid, sugar, drug, or small molecule.

The methods and compositions disclosed herein provide optimized erythroid cells derivatized with therapeutic or diagnostic agents for use in a broad range of indications. Optimized reagents, intermediates and synthetic methods are also provided.

In one aspect, the invention features a preparation, e.g., pharmaceutical preparation, of erythroid cells, e.g., hematopoietic stem cells, reticulocytes, or erythrocytes, comprising, as many as, at least, more than, or about 5,000, 10,000, 50,000, 100,000, 200,000, 300,000, 400,000, 500,000 coupling reagents per cell. For instance, in some aspects the disclosure features a preparation, e.g., pharmaceutical preparation, of erythroid cells comprising at least 5,000, 10,000, 50,000, 100,000, 200,000, 300,000, 400,000, 500, 000 coupling reagents per cell. In some embodiments, a pharmaceutical preparation described herein comprises up to 10,000, 50,000, 100,000, 200,000, 300,000, 400,000, 500,000 coupling reagents per cell. In an embodiment, at least 50, 60, 70, 80, 90, 95, 99, or 99.9% of the cells in the preparation have the recited level of coupling reagent, e.g., an alkyne coupling reagent (KR) per cell or an azide coupling reagent (AR) per cell. In an embodiment at least about 1, 2, 3, 5, 10, 20, 30, or 40% of the cells in the preparation have the recited level of agent per cell. In an embodiment, the preparation comprises, as many as, at least, more than, or about, 10,000, 50,000, 100,000, $10^6$, $10^7$, $10^8$, or $10^9$ cells. In an embodiment, the preparation comprises, as many as, at least, more than, or about, $10^{10}$, $10^{11}$, or $10^{12}$ cells. In an embodiment, the cell further comprises a polypeptide expressed from an exogenous nucleic acid, e.g., inside the cell or at the cell surface.

In another aspect, the invention features a preparation, e.g., pharmaceutical preparation, of erythroid cells, e.g., hematopoietic stem cells, reticulocytes, or erythrocytes, comprising, as many as, at least, more than, or about 1,000, 2,000, 3,000, 4,000, or 5,000 coupling reagents per cell. For instance, in some aspects the disclosure features a preparation, e.g., pharmaceutical preparation, of erythroid cells comprising at least 1,000, 2,000, 3,000, 4,000, or 5,000 coupling reagents per cell.

In another aspect, the invention features a preparation, e.g., pharmaceutical preparation, of erythroid cells, e.g., hematopoietic stem cells, reticulocytes, or erythrocytes, comprising, as many as, at least, more than, or about 5,000, 10,000, 50,000, 100,000, 200,000, 300,000, 400,000, 500,000, copies of an agent, e.g., heterologous agent, coupled to the cell by a residual linker. In some embodiments, the residual linker comprises a click signature. For instance, in some aspects the disclosure features a preparation, e.g., pharmaceutical preparation, of erythroid cells comprising at least 5,000, 10,000, 50,000, 100,000, 200,000, 300,000, 400,000, 500,000, copies of a heterologous agent, coupled to the cell by residual linker comprising a click signature.

In an embodiment at least about 50, 60, 70, 80, 90, 95, 99, or 99.9% of the cells in the preparation have the recited level of agent per cell. In an embodiment at least about 50, 60, 70, 80, 90, 95, 99, or 99.9% of the cells in the preparation comprise a first agent and a second agent, e.g., wherein a cell is considered positive for an agent if the level of agent is greater than that measured in 99% of otherwise similar unlabeled cells. In an embodiment at least about 1, 2, 3, 5, 10, 20, 30, or 40% of the cells in the preparation have the recited level of agent per cell. In an embodiment the preparation comprises, as many as, at least, more than, or about, 10,000, 50,000, 100,000, $10^6$, $10^7$, $10^8$, or $10^9$ cells. In an embodiment, the preparation comprises, as many as, at least, more than, or about, $10^{10}$, $10^{11}$, or $10^{12}$ cells.

In an embodiment, the erythroid cells are reticulocytes, e.g., from in vitro expanded, differentiated and enucleated HSCs. In embodiments, the erythroid cells comprise hematopoietic precursor cells, e.g., CD34+ cells.

In an embodiment, the erythroid cells are erythrocytes, e.g., obtained from blood.

In an embodiment, the erythroid cells are genetically modified, e.g., the cells comprise a polypeptide expressed from an exogenous nucleic acid (e.g., DNA or RNA, e.g., mRNA).

In an embodiment, the erythroid cells are encapsulated, e.g., hypotonically loaded, with an exogenous protein.

In an embodiment, the preparation is free or substantially free of free coupling reagent, unreacted coupling reagent, an organic solvent, a metal (e.g., copper), a catalyst, or unlabeled cells or unmodified cells.

In an embodiment, the agent is an agent described in WO2015/15302; or in WO2015/073587, each of which is hereby incorporated by reference in its entirety.

In an embodiment, the agent comprises a peptidic agent, e.g., a polypeptide, an enzyme, or an antibody. In an embodiment, the peptidic agent comprises a cytokine, a receptor, a ligand, a hormone, a growth factor, a blood factor, a lysosomal storage enzyme, asparaginase, or a fragment of any of the foregoing comprising an extracellular domain, counterligand binding domain, or other biologically active domain, or a fragment or variant thereof. In an embodiment, the agent comprises an antigen, e.g., a tumor antigen, and infectious disease antigen, and autoantigen.

In an embodiment, the agent comprises a lipid; nucleic acid, e.g. RNA, DNA, siRNA; sugar; drug; or small molecule.

In an embodiment, the agent comprises a polypeptide of greater than about 30, 50, 75, 100, 150, 200, 250, 300, 350, or 400 kilodaltons. In an embodiment, the agent comprises a polypeptide of about 1-2, 1-5, 2-5, 5-10, 10-20, 20-50, 50-100, 100-200, or 200-500 kDa. In an embodiment, the agent comprises a polypeptide of greater than 10, 15, 20, 25, 30, 40, 50, 100, 200, 300, 400, or 500 amino acids.

In an embodiment, the agent, e.g., a polypeptide, comprises post-translational modification, e.g., a post-translational modification that is not made by erythroid cells, or made inefficiently by erythroid cells. In embodiments, the polypeptide, e.g., an antibody, comprises one or more disulfide bridges. In embodiments, the agent, e.g., a polypeptide, lacks a post-translational modification or comprises the modification at a lower level than the protein produced by a mammalian cell, e.g., a CHO cell. In embodiments, the polypeptide (e.g., an antibody) undergoes deglycosylation. In embodiments, the deglycosylation leads to lower ADCC induction and/or lower interaction with Fc gamma receptors.

In some embodiments, the agent, e.g., a polypeptide, does not comprise a post-translational modification that is ordinarily present if the polypeptide is produced in a human cell, e.g., a human erythroid cell. In some embodiments, the agent, e.g., polypeptide, comprises a post-translational modification at a lower level than is ordinarily present if the polypeptide is produced in a human cell, e.g., at least 10%, 20%, 30%, 40%, 50%, 60%, 70%, 80%, 90% lower.

In some embodiments, a polypeptide agent comprises one or more non-canonical amino acids. The non-canonical amino acid may be, for example, p-methoxyphenylalanine (pMpa); p-acetylphenylalanine (pApa); p-benzoylphenylalanine (pBpa); p-iodophenylalanine (pIpa); p-azidophenylalanine (pAzpa); p-propargyloxyphenylalanine (pPpa); α-aminocaprylic acid; o-nitrobenzylcysteine (o-NBC); 1,5-dansylalanine; and o-nitrobenzylserine (o-NBS).

In an embodiment, the agent, e.g., a polypeptide, is toxic to, or compromises the growth, function, life span, or development of an erythroid cell. In embodiments, an agent that is toxic to a cell is an agent (e.g., enzyme) that produces a metabolite toxic to the cell.

In an embodiment, the agent comprises a multimeric polypeptide, e.g., a dimer, e.g., a homodimer or heterodimer, a trimer, e.g., a homotrimer or heterotrimer, or a tetramer, e.g., a homotetramer or heterotetramer, e.g., an antibody or a cell surface receptor, e.g., a receptor for a disease vector, e.g., a virus, a drug, or a toxin.

In an embodiment, the agent comprises a polypeptide, e.g., a multimeric polypeptide, comprising a plurality of cysteine bridges. In an embodiment, the agent comprises a polypeptide, e.g., a multimeric polypeptide, comprising one or more cysteine bridges.

In an embodiment, the agent comprises a difficult to express protein. In embodiments, a difficult to express protein is a protein that comprises a post-translational modification that does not normally occur in erythroid cells. In embodiments, the post-translational modification comprises cleavage by a protease that is not normally expressed in erythroid cells. In embodiments, the difficult to express protein comprises an activated clotting factor, and the protease that activates the clotting factor is not ordinarily expressed in erythroid cells. Exemplary activated clotting factors that are activated by cleavage include Factor Va, VIIa, VIIIa, IXa, Xa, XIa, XIIIa, and thrombin.

In an embodiment, the agent comprises an antibody molecule, e.g., a polypeptide comprising one or more of the following: a) sufficient variable region to bind cognate antigen, e.g., HC CDR1, HC CDR2, and HC CDR3, LC CDR1, LC CDR2, and LC CDR3; b) a heavy chain constant sequence comprising one or more of CH1, CH2, and CH3; c) a functional Fc region; and d) a modified or inactive Fc region, e.g., a mutationally inactivated Fc region or an Fc region having a glycosylation state that impairs Fc activity, e.g., a deglycosylated Fc region. In an embodiment, an antibody is a multispecific antibody, e.g., a bispecific antibody. Examples of antibodies include, but are not limited to, Fab, Fab', F(ab')2, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide bridge at the hinge region, an isolated epitope binding fragment of an antibody, maxibodies, minibodies, nanobodies, intrabodies, diabodies, triabodies, tetrabodies, v-NAR and bis-scFv. In embodiments, the CDRs are defined according to Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), or a combination thereof.

In an embodiment, the agent comprises an antibody, e.g., an IgA, IgG, IgG1, IgG2, IgM, IgE, or IgD.

In an embodiment, the agent comprises an anti-PDL1 antibody molecule, an anti 4-1BB antibody molecule, or an anti-α4β7 antibody molecule. In an embodiment, the agent comprises an anti-PDL1 antibody, an anti 4-1BB antibody, anti-α4β7 antibody, or protein A/G. In an embodiment, the agent comprises 4-1BBL, Factor VIIa, Factor Xa, asparaginase, IL-10, or MOG peptide. In an embodiment, the agent comprises asparaginase and the asparaginase activity of the cells is about $1 \times 10^{-12}$-$1 \times 10^{-9}$ U/cell, $1 \times 10^{-12}$-$1 \times 10^{-11}$ U/cell, $1 \times 10^{-11}$-$1 \times 10^{-10}$ U/cell, or $1 \times 10^{-10}$-$1 \times 10^{-9}$ U/cell.

In another aspect, the invention features a preparation, e.g., pharmaceutical preparation, of erythroid cells, e.g., hematopoietic stem cells, reticulocytes, or erythrocytes, comprising: as many as, at least, more than, or about 1,000, 2,000, 3,000, 4,000, 5,000, 10,000, 50,000, 100,000, 200,000, 300,000, 400,000, or 500,000 copies of a first agent, e.g., a heterologous agent, coupled to the cell by a residual linker; and as many as, at least, more than, or about 1,000, 2,000, 3,000, 4,000, 5,000, 10,000, 50,000, 100,000, 200,000, 300,000, 400,000, or 500,000, copies of a second agent, e.g., a heterologous agent, coupled to the cell by a second residual linker. For instance, in some aspects, the disclosure features a preparation, e.g., pharmaceutical preparation, of erythroid cells, comprising at least 1,000 copies of a first heterologous agent, coupled to the cell by a residual linker having a click signature; and at least 1,000 copies of a second heterologous agent, coupled to the cell by a second residual linker having a second click signature. In an embodiment, the first and second residual linkers have different structures. In an embodiment, the first and second residual linkers have the same structure. In an embodiment, the first and second residual linkers have the same structures but have the opposite orientation. In embodiments, the first click signature is different from the second click signature. In some embodiments, the cell comprises at least 2,000 copies of the first heterologous agent and at least 2,000 copies of the second heterologous agent. In some embodiments, the cell comprises at least 5,000 copies of the first heterologous agent and at least 5,000 copies of the second heterologous agent. In some embodiments, the cell comprises at least 10,000 copies of the first heterologous agent and at least 10,000 copies of the second heterologous agent. In some embodiments, the cell comprises at least 50,000 copies of the first heterologous agent and at least 50,000 copies of the second heterologous agent. In some embodiments, the cell comprises at least 100,000 copies of the first heterologous agent and at least 100,000 copies of the second heterologous agent.

In an embodiment, at least about 1, 2, 3, 5, 10, 20, 30, 40, 50, 60, 70, 80, 90, 95, 99, or 99.9% of the cells in the preparation have the recited level of agents per cell. In an embodiment the preparation comprises, as many as, at least, more than, or about 10,000, 50,000, 100,000, $10^6$, $10^7$, $10^8$, $10^9$, $10^{10}$, $10^{11}$, or $10^{12}$ cells. In an embodiment the preparation comprises at least 10,000, 50,000, 100,000, $10^6$, $10^7$, $10^8$, $10^9$, $10^{10}$, $10^{11}$, or $10^{12}$ cells.

In an embodiment, the erythroid cells further comprise one or more additional agent, e.g., an Nth agent, where N is at least 3, 4, 5, 6, 7, 8, 9, 10, 50, 100, or 200 agents, wherein for each additional agent the cell comprises as many as, at least, more than, or about 1,000, 2,000, 3,000, 4,000, 5,000, 10,000, 50,000, 100,000, 200,000, 300,000, 400,000, or 500,000, copies of the additional agent, e.g., a heterologous agent, coupled to the cell by a residual linker.

In an embodiment, a preparation, e.g., pharmaceutical preparation, disclosed herein is free or substantially free of free coupling reagent, unreacted coupling reagent, an organic solvent, a metal (e.g., copper), a catalyst, or unlabeled cells or unmodified cells.

In an embodiment, in a cell or preparation, e.g., pharmaceutical preparation, disclosed herein, less than 10%, 20%, 30%, 40%, 50%, 60%, 70%, 80%, or 90% of the coupling reagent on the cell is unreacted coupling reagent. In an embodiments, m a cell or preparation, e.g., pharmaceutical preparation, disclosed herein, less than 15%, 14%, 13%, 12%, 11%, or 10% of the coupling reagent on the cell is unreacted coupling reagent.

In an embodiment, the agent comprises a peptidic agent, e.g., a polypeptide, a protein drug, an enzyme, an antibody (e.g., an scFv), a cytokine, a cytokine receptor, a receptor molecule, a ligand, a hormone, a growth factor, a blood factor, a lysosomal storage enzyme, asparaginase, an antigen (e.g., a tumor antigen, an infectious disease antigen, or autoantigen), or an immune stimulatory molecule (e.g., a costimulatory molecule). In embodiments, the antibody comprises a whole antibody, a fragment thereof, single-chain antibody, humanized antibody; murine antibody; chimeric, mouse-human, mouse-primate, primate-human monoclonal antibody, anti-idiotype antibody, antibody fragments, such as, e.g., scFv, (scFv)2, Fab, Fab', and F(ab')2, F(ab1)2, Fv, dAb, and Fd fragments, diabodies, and an antibody-related polypeptide.

In another aspect, the invention features a method of making a pharmaceutical preparation, product, or intermediate comprising: a) coupling a first coupling reagent, e.g., a GMP grade coupling reagent, to an erythroid cell, thereby making a pharmaceutical preparation, product, or intermediate. In an embodiment, the method further comprises: b) contacting the cell with an agent coupled to a second coupling reagent, e.g., a GMP grade coupling reagent, e.g., under conditions suitable for reaction of the first coupling reagent with the second coupling reagent. In embodiments, the method comprises coupling the second coupling reagent to the agent, e.g., before or after step a). In embodiments, the intermediate of step a) is stored before the contacting of step b). In embodiments, the agent coupled to a second coupling reagent is stored before the contacting of step b).

In an embodiment, the method comprises providing a population of erythroid cells for coupling in a). In an embodiment, the method comprises reducing or minimizing entities in the preparation that react with the first coupling reagent. In an embodiment, the method comprises treating, e.g., washing the cell to remove unbound material, e.g., protein, from the cell, e.g., capable of reacting with the first coupling reagent.

In an embodiment, a second agent is coupled to the cell, wherein the method comprises: c) coupling a second coupling reagent, e.g., a GMP grade coupling reagent to an erythroid cell, and d) contacting the cell with a second agent coupled to a second coupling reagent, e.g., a GMP grade coupling reagent, e.g., under conditions suitable for reaction of the first coupling reagent with the second coupling reagent.

In embodiments, the method comprises:
a) coupling a first coupling reagent to the cell,
b) contacting the cell with a first agent coupled to a second coupling reagent which is capable of reacting with the first coupling reagent,
c) coupling a third coupling reagent to the cell, and
d) contacting the cell with a second agent coupled to a fourth coupling reagent which is capable of reacting with the third coupling reagent.

In embodiments, steps a), b), c), and d) are carried out in one of the following orders:
a), then b), then c), and then d);
a), then c), then b), and then d);
a), then c), then d), and then b);
a), then c), then b) and d) simultaneously;
c), then d), then a), and then b);
c), then a), then b), and then d);
c), then a), then d), and then b);
c), then a), then b) and d) simultaneously;
a) and c) simultaneously, then b), and then d);
a) and c) simultaneously, then d), and then b); or
a) and c) simultaneously, then b) and d) simultaneously.

In an embodiment, the conjugation efficiency of the coupling reaction is greater than 50%, 60%, 70%, 80%, 85%, 90%, 95%, 97%, or 98%.

In an embodiment, the erythroid cells are reticulocytes, e.g., from in vitro expanded, differentiated and enucleated HSCs.

In an embodiment, the erythroid cells are erythrocytes, e.g., obtained from blood.

In an embodiment, the erythroid cells are genetically modified, e.g., the cells comprise a polypeptide expressed from an exogenous nucleic acid (e.g., DNA or RNA, e.g., mRNA).

In an embodiment, the erythroid cells are encapsulated, e.g., hypotonically loaded, with an exogenous protein, an agent that binds to a cellular protein, DNA, or RNA.

In some embodiments, an enucleated cell described herein is a reticulocyte, an erythrocyte, or a platelet.

In another aspect, the invention features a method of administering an agent to a subject, e.g., treating a subject, comprising administering a preparation, a composition, or cells described herein to the subject, thereby administering an agent to the subject, e.g., treating the subject. In an embodiment, the method comprises, providing, e.g., by making, or obtaining from another entity, the preparation, composition, or cells. In another aspect, the invention features a cell (e.g., enucleated erythroid cell) described herein, for use in treating a disease or disorder, e.g., a disease or disorder described herein. In another aspect, the invention features the a cell (e.g., enucleated erythroid cell) described herein, for the manufacture of a medicament for treating a disease or disorder, e.g., a disease or disorder described herein.

In an embodiment, the cells are allogeneic to the subject.

In an embodiment, the cells are autologous to the subject.

In an embodiment, an agent is coupled to the cells. In an embodiment, the agent comprises a peptidic agent, e.g., a polypeptide, an enzyme, or an antibody. In an embodiment, the agent comprises a cytokine, a receptor, a ligand, a hormone, a growth factor, a blood factor, a lysosomal storage enzyme, asparaginase, or a fragment of any of the foregoing comprising an extracellular domain, counterligand binding domain, or other biologically active domain.

In an embodiment, less than 7, 6, 5, 4, 3, 2, or 1 day elapses between coupling an agent to the cells and administering the cells to the subject.

In an embodiment, the cells are autologous and less than 7, 6, 5, 4, 3, 2, or 1 day elapses between removal of the cell from the subject and administering the cells to the subject.

In an embodiment, at least 1, 2, 3, 4, 5, 6, 7, 14, 21, or 28 days elapse between removal of the cell from a subject and administering the cells to a subject (e.g., the same or a different subject).

In an embodiment, the method comprises evaluating the subject, and responsive to the evaluation, selecting an agent for coupling to the cell.

In embodiments, a coupling step occurs in vivo or ex vivo. For instance, in embodiments, a coupling agent is administered to a subject under conditions that allow the coupling reagent to couple to a cell, e.g., an erythroid cell. In some embodiments, an agent coupled to a second coupling reagent is administered to a subject under conditions that allow the agent to couple to a cell, e.g., an erythroid cell.

In another aspect, the invention features a method of providing a preparation, composition, or cells comprising: receiving from an entity the identity of an agent, e.g., an agent suitable for the treatment of a subject, and coupling the agent to a cell by a method described herein, thereby providing a preparation, composition, or cells.

In another aspect, the invention features a kit comprising one or more of the following: a) optionally, an erythroid cell; b) a first coupling reagent; c) a second coupling reagent; d) an agent; e) optionally, an erythroid cell coupled to a coupling reagent; f) an agent coupled to a coupling reagent; or g) a reagent for detecting the presence of any of a-f.

In an embodiment the kit comprise one or more of b, c, d, f and g.

In some aspects, the invention features a kit comprising: a) an activated cell (e.g., erythroid cell), b) a first activated agent, c) a second activated agent, and d) optionally a third or further activated agents.

In some aspects, the invention features a method of making a functionalized cell (e.g., a functionalized cell described herein), comprising: a) receiving instructions from a third party (e.g., a doctor, doctor's office, or hospital) to provide a functionalized cell having one or more specified agents, b) contacting an activated cell with an agent or a plurality (e.g., 2, 3, 4, 5, 10, 20, or more) different agents, thereby making the functionalized cell, and c) providing the functionalized cell to the third party.

In some aspect, the invention features a method of obtaining a functionalized cell (e.g., a functionalized cell described herein), comprising: a) transmitting instructions to a third party (e.g., a laboratory) to provide a functionalized cell having one or more specified agents, b) receiving the functionalized cell from the third party, and c) administering the functionalized cell to a subject in need thereof.

In some aspects, the disclosure features a cell (e.g., an erythroid cell and/or an enucleated cell, e.g., an enucleated erythroid cell), comprising:

an agent (e.g., an exogenous polypeptide) at the cell surface, and a linker, e.g., a residual linker, covalently linking the agent to the cell surface (e.g., to a polypeptide or carbohydrate at the cell surface), wherein the residual linker comprises a click signature.

In some embodiments, the click signature was formed as the product of a click reaction. In some embodiments, the click signature has the structure of a click signature described herein.

The disclosure provides, in some aspects, a cell (e.g., an erythroid cell and/or an enucleated cell, e.g., an enucleated erythroid cell), comprising an exogenous polypeptide agent covalently linked to the cell surface by a residual linker comprising a click signature, via an amino acid side chain of a protein comprised by the cell, e.g., a protein at the cell surface, wherein the click signature was formed as the product of a click reaction or has the structure of a click signature, e.g., a click signature described herein.

The disclosure provides, in some aspects, a cell (e.g., an erythroid cell and/or an enucleated cell, e.g., an enucleated erythroid cell), comprising:

a plurality of exogenous polypeptide agents, each exogenous polypeptide agent of the plurality being covalently linked to the cell surface by a residual linker comprising a click signature, wherein at least 10%, 20%, 30%, 40%, 50%, 60%, 70%, 80%, 90%, 95%, or 99% of exogenous polypeptide agents on the cell are linked via an amino acid side chain to a protein comprised by the cell, e.g., a protein at the cell surface, wherein the click signature was formed as the product of a click reaction or has the structure of a click signature, e.g., a click signature described herein.

In some aspects, the disclosure provides an enucleated erythroid cell, comprising a plurality of copies of an exogenous polypeptide agent covalently linked to the cell surface by a residual linker comprising a click signature, wherein the click signature was formed as the product of a click reaction or has the structure of a click signature, wherein one or more of List 1 herein applies. In some embodiments, the cell lacks a sortase transfer signature. In some embodiments, the cell does not comprise a sortase transfer signature covalently linked to the click signature.

In some aspects, the disclosure provides an enucleated erythroid cell, comprising a plurality of copies of an exogenous polypeptide agent covalently linked to the cell surface by a residual linker comprising a click signature, wherein the click signature was formed as the product of a click reaction or has the structure of a click signature, wherein at least 50%, 60%, 70%, 80%, or 90% of the plurality of exogenous polypeptide agents have the same orientation relative to the cell surface. In some embodiments, the cell lacks a sortase transfer signature. In some embodiments, the cell does not comprise a sortase transfer signature covalently linked to the click signature. In some embodiments, the cell is not genetically engineered, e.g., does not comprise a polypeptide that was expressed from an exogenous nucleic acid. In other embodiments, the cell is genetically engineered, e.g., comprises a polypeptide that was expressed from an exogenous nucleic acid. In some embodiments, the cell does not comprise a non-natural amino acid. In some embodiments, the cell does not comprise a transmembrane protein having a non-natural amino acid.

In some embodiments, the exogenous polypeptide agent comprises a π-clamp. In some embodiments, the exogenous polypeptide agent is covalently linked to the enucleated erythroid cell via the π-clamp. In some embodiments, the exogenous polypeptide agent comprises a ncAA. In some embodiments, the exogenous polypeptide agent is covalently linked to the enucleated erythroid cell via the ncAA. In some embodiments, the exogenous polypeptide agent comprises two or more cysteine residues. In some embodiments, the exogenous polypeptide agent is covalently linked to the enucleated erythroid cell via the two or more cysteine residues, e.g., via a ThioLinker.

In some embodiments, the exogenous polypeptide agent is a peptide ligand that binds a binding partner.

In some embodiments, the cell further comprises a second agent, e.g., a second exogenous polypeptide agent, e.g., wherein the second exogenous polypeptide agent is covalently linked to the cell surface by a second residual linker comprising a click signature. In some embodiments, the cell further comprises a third agent, e.g., a third exogenous polypeptide agent, e.g., wherein the third exogenous polypeptide agent is covalently linked to the cell surface by a second residual linker comprising a click signature.

In some embodiments, the agent, e.g., exogenous polypeptide agent, is covalently linked to an endogenous molecule of the cell, e.g., an endogenous polypeptide at the cell surface.

In some embodiments, at least 50%, 60%, 70%, 80%, or 90% of the exogenous polypeptide agents are covalently linked to the cell surface with a preselected orientation, e.g., are attached by the same moiety or moieties of the exogenous polypeptide agents (e.g., an N-terminus, a C-terminus, or a particular residue, e.g., a particular ncAA, or a particular plurality of residues, e.g., two cysteine residues). In some embodiments of the preparations described herein, at least 50%, 60%, 70%, 80%, or 90% of the exogenous polypeptide agents in the preparation are covalently linked to an enucleated erythroid cell surface with a preselected orientation, e.g., are attached by the same moiety or moieties of the exogenous polypeptide agents (e.g., an N-terminus, a C-terminus, or a particular residue, e.g., a particular ncAA, or a particular plurality of residues, e.g., two cysteine residues).

In some embodiments, the agent, e.g., exogenous polypeptide agent is covalently linked to an endogenous molecule of the cell, e.g., an endogenous polypeptide at the cell surface. In some embodiments, the linker connects the agent to an endogenous molecule of the cell, e.g., an endogenous polypeptide or sugar at the cell surface. In some embodiments, the linker connects the agent to an exogenous molecule of the cell, e.g., an exogenous polypeptide or sugar at the cell surface.

In some embodiments, the click signature comprises a cyclic moiety, e.g., a heterocycle such as triazole e.g., a disubstituted triazole, or a cycloadduct. In some embodiments, the click signature comprises a cycloalkene such as cyclohexene, an alkyl sulfide, a dihydropyrazine such as a 1,2-dihydropyrazine, a diazole, or a sulfur-containing ring such as a thiopyran.

In some embodiments, the click signature was formed by or is capable of being formed by cycloaddition (e.g., a 1,3-dipolar cycloaddition or hetero-Diels-Alder cycloaddition), nucleophilic ring-opening (e.g., openings of strained heterocyclic electrophiles such as aziridines, epoxides, cyclic sulfates, aziridinium ions, and episulfonium ions), carbonyl chemistry of non-aldol type (e.g., formation of ureas, thioureas, hydrazones, oxime ethers, amides, or aromatic heterocycles), or an addition to a carbon-carbon multiple bond (e.g., epoxidation, aziridination, dihydroxylation, sulfenyl halide addition, nitosyl halide addition, or Michael addition).

In some aspects, the disclosure features a method of making (e.g., manufacturing) a cell (e.g., an erythroid cell, e.g., an enucleated erythroid cell), functionalized with an agent comprising:

(a) providing an activated cell comprising a cell bound, e.g., covalently bound, to a first coupling moiety, e.g., a first click handle, (b) providing an activated agent comprising an agent (e.g., an exogenous polypeptide) bound, e.g., covalently bound, to a second coupling moiety capable of reacting with the first coupling moiety, e.g., a second click handle capable of reacting with the first click handle, and (c) contacting the activated cell with the activated agent, thereby producing a cell functionalized with the agent.

In embodiments, the method comprises contacting a cell with a first coupling reagent which comprises the first coupling moiety e.g., first click handle, thereby producing the activated cell. In embodiments, the method comprises contacting the agent with a second coupling reagent which comprises the second coupling moiety, e.g., second click handle, thereby producing the activated agent. In embodiments, the method comprises synthesizing the agent to contain the second coupling moiety, e.g., second click handle, e.g., through incorporation of a non-canonical amino acid. In embodiments, the method comprises making a cell comprising a first coupling moiety, e.g., through incorporation of a non-canonical amino acid comprising the first coupling moiety or through incorporation of a sugar (e.g., into a carbohydrate) comprising the first coupling moiety.

In embodiments, contacting the cell with the first coupling reagent occurs before or after contacting the agent with the second coupling reagent. In embodiments, contacting the cell with the first coupling reagent and contacting the agent with the second coupling reagent occur at the same time, e.g., begin at the same time, end at the same time, or have partial overlap.

In embodiments, the first coupling reagent is membrane impermeable. In embodiments, the second coupling reagent is membrane impermeable. In embodiments, the first coupling reagent is membrane permeable. In embodiments, the second coupling reagent is membrane permeable.

In some aspects, the disclosure features a cell, e.g., an erythroid cell, e.g., an enucleated erythroid cell, produced by a method herein. In some embodiments, the method comprises (a) providing an activated cell comprising a cell covalently bound to a first click handle, (b) providing an activated agent comprising an agent (e.g., an exogenous polypeptide) covalently bound to a second click handle capable of reacting with the first click handle, and (c) contacting the activated cell with the activated agent, thereby producing a cell functionalized with the agent.

In some aspects, the disclosure features a method of treating a disease, comprising administering a functionalized cell described herein to a subject in need thereof.

In some embodiments, the first coupling reagent comprises a first substrate-reactive moiety that reacts with one of the following moieties on the agent:
  a) a primary amine (—NH$_2$) e.g., in a lysine or N-terminus,
  b) carboxyl (—COOH) e.g., in an aspartic acid, glutamic acid, or C-terminus,
  c) sulfhydryl (—SH) e.g., in cysteine, or
  d) carbonyl (—CHO) e.g., a ketone or aldehyde group e.g. in a glycoprotein e.g., an oxidized glycoprotein.

In some embodiments, the second coupling reagent comprises a first substrate-reactive moiety that reacts with one of the following moieties on the cell (e.g., a moiety of a protein or carbohydrate on the cell):
  a) a primary amine (—NH$_2$) e.g., in a lysine or N-terminus,
  b) carboxyl (—COOH) e.g., in an aspartic acid, glutamic acid, or C-terminus,
  c) sulfhydryl (—SH) e.g., in cysteine, or
  d) carbonyl (—CHO) e.g., a ketone or aldehyde group e.g., in a glycoprotein, e.g., an oxidized glycoprotein.

In some embodiments, the first substrate-reactive moiety and the second substrate-reactive moiety react with the same type of moiety, e.g., the first substrate-reactive moiety reacts with a first primary amine and the second substrate-reactive moiety reacts with a second primary amine. In some embodiments, the first substrate-reactive moiety and the second substrate-reactive moiety react with different types of moiety.

In some embodiments, the first or second coupling reagent comprises a sortase recognition site e.g., an N-terminal GGG or a C-terminal LPXTG (SEQ ID NO: 1).

In some embodiments, the coupling reagent (e.g., first or second coupling reagent) comprises a click handle. In embodiments, the click handle comprises an alkyne, e.g., a strained alkyne, e.g., a cyclooctyne, e.g., DBCO-sulfo-NHS ester. In some embodiments, the click handle comprises an azide, e.g., a 3-azidopropionic acid sulfo-NHS ester.

In some embodiments, a method herein further comprises contacting the functionalized cell with a terminating reagent which comprises only one coupling moiety, e.g., one click handle. In embodiments, the terminating reagent can react with un-reacted click handles on the cell, thereby reducing the number of un-reacted click handles on the cell. In embodiments, the terminating reagent can react with un-reacted click handles on the agent, thereby reducing the number of un-reacted click handles on the agent. In embodiments, the method comprises sequentially, in either order, contacting the functionalized cell with a terminating reagent can react with un-reacted click handles on the cell and contacting the functionalized cell with a terminating reagent can react with un-reacted click handles on the agent. In embodiments, un-reacted terminating reagent is washed away between the two contacting steps. In embodiments, the terminating reagent has a lower molecular weight and/or lower steric hindrance than the agent. In embodiments, the terminating reagent comprises a detectable label. In some embodiments, the terminating reagent with a detectable label is contacted with an aliquot of a batch of functionalized cells. In some embodiments, if the amount of detectable label that reacts with the functionalized cell is below a predetermined threshold, the batch is approved or released. In some embodiments, if the amount of detectable label that reacts with the functionalized cell is above a predetermined threshold, the batch is withheld or subjected to further processing, e.g., is contacted with a terminating reagent. In embodiments, the terminating reagent comprises an azide or an alkyne group. In embodiments, once the terminating reagent reacts with an agent or cell, it is not substantially reactive, e.g., no more reactive than the N-terminus of wild-type human glycophorin A.

In some embodiments, at least 70%, 80%, 90%, 95%, 97%, 98%, 99%, 99.5%, 99.5%, 99.8%, or 99.9% of the enucleated erythroid cells are labeled, e.g., wherein a cell is considered labeled if the level of agent is greater than that measured in 99% of otherwise similar unlabeled cells.

In some embodiments, the enucleated erythroid cells are labeled with an average of (or an enucleated erythroid cell described herein is labeled with) 50-200,000 copies per cell of the agent, e.g., 50-100, 100-200, 200-500, 500-1,000, 1,000-2,000, 2,000-5,000, 5,000-10,000, 10,000-20,000, 20,000-50,000, 50,000-100,000, or 100,000-200,000 copies per cell of the agent, or with at least 50, 100, 200, 500, 1,000, 2,000, 5,000, 10,000, 20,000, 50,000, 100,000, or 200,000 copies per cell of the agent, or with up to 50, 100, 200, 500, 1,000, 2,000, 5,000, 10,000, 20,000, 50,000, 100,000, or 200,000 copies per cell of the agent.

In some embodiments, at least $10^7$, $10^8$, or $10^9$ enucleated erythroid cells are labeled.

In some embodiments, the population of enucleated erythroid cells are labeled with at least 1, 2, 5, 10, 20, 50, 100, 200, or 500 ng of the agent, e.g., exogenous polypeptide.

In some embodiments, the linked polypeptide agent comprises anti-PD-L1, anti-α4β7, anti-m41BBL, 4-1BBL, Factor VIIa, Factor Xa, asparaginase, or MOG peptide.

In some embodiments, at least 50, 60, 70, 80, 95, 90, 95, 96, 97, 98, or 99% of the labeled erythroid cells bind a ligand, e.g., in a flow cytometry assay of Example 6. In some embodiments, at least 50, 60, 70, 80, 95, 90, 95, 96, 97, 98, or 99% of the enucleated erythroid cells comprise an agent that binds a ligand, e.g., in a flow cytometry assay of Example 6. In embodiments, the cell is considered to bind the ligand by a flow cytometry assay of Example 6 if it has a signal greater than that measured in 99% of otherwise similar cells that lack the agent.

In embodiments, the agent is linked (e.g., adjacently linked with no intervening atoms, or having one or more atoms between the agent and endogenous polypeptide) to an amino acid of an endogenous polypeptide. In embodiments, the linker has a length of at least 5, 10, 20, 30, 40 50, 60, 70, 80, 90, or 100 nm. In embodiments, the linker has a length of about 30-100, 40-90, 50-80, or 60-70 nm. In embodiments, the linker has a length such that the agent is outside of the glycocalyx of the erythroid cell. In some embodiments, the linker comprises PEG, e.g., PEG having a length of about 3-20, e.g., 4-13, e.g., about 4, 5, 12, or 13. In some embodiments, the length of the PEG component is between about 30-60 Angstroms, e.g., 30-40, 40-50, or 50-60 Angstroms. In some embodiments, the linker comprises PEG having a length of about 50-200, 200-400, 400-600, 600-800 or 800-1000 Angstroms.

In some embodiments one or more of List 1 applies, wherein List 1 is:
a) the agent is linked (e.g., via a residual linker) to an amino acid other than a glycine of an endogenous membrane protein, e.g., is linked to at least one non-glycine residue;
b) the agent is linked (e.g., via a residual linker) to a site other than the N-terminus or C-terminus of an endogenous membrane protein;
c) the agent is linked (e.g., via a residual linker) to a site other than the N-terminus or C-terminus of an membrane protein;
d) the agent is linked (e.g., via a residual linker) to a full length endogenous membrane protein;
e) the agent is linked to at least 10, 20, 50, or 100 sequence-distinct polypeptides, e.g., endogenous polypeptides;
f) the cell functionalized with an agent lacks a sortase transfer signature (i.e., a sequence that can be created by a sortase reaction) such as LPXTG (SEQ ID NO: 1).
g) the agent is not linked to a sortase transfer signature,
h) at least 10%, 20%, 30%, 40%, 50%, 60%, 70%, 80%, 90%, 95%, or 99% of agents on the cell are not linked to a sortase transfer signature,
i) the click signature is not linked to a sortase transfer signature,
j) at least 10%, 20%, 30%, 40%, 50%, 60%, 70%, 80%, 90%, 95%, or 99% of click signatures on the cell are not linked to a sortase transfer signature,
k) the agent is not linked to an extracellular sortase transfer signature;
l) at least 10%, 20%, 30%, 40%, 50%, 60%, 70%, 80%, 90%, 95%, or 99% of agents on the cell are not linked to an extracellular sortase transfer signature,
m) the click signature is not linked to an extracellular sortase transfer signature,
n) at least 10%, 20%, 30%, 40%, 50%, 60%, 70%, 80%, 90%, 95%, or 99% of click signatures on the cell are not linked to an extracellular sortase transfer signature,
o) the agent is not linked to an extracellular sortase transfer signature that is within 1, 2, 3, 4, 5, 10, 20, 50, or 100 amino acids of a transmembrane segment;
p) at least 10%, 20%, 30%, 40%, 50%, 60%, 70%, 80%, 90%, 95%, or 99% of agents on the cell are not linked an extracellular sortase transfer signature that is within 1, 2, 3, 4, 5, 10, 20, 50, or 100 amino acids of a transmembrane segment,
q) the click signature is not linked to an extracellular sortase transfer signature that is within 1, 2, 3, 4, 5, 10, 20, 50, or 100 amino acids of a transmembrane segment,
r) at least 10%, 20%, 30%, 40%, 50%, 60%, 70%, 80%, 90%, 95%, or 99% of click signatures on the cell are not linked to an extracellular sortase transfer signature that is within 1, 2, 3, 4, 5, 10, 20, 50, or 100 amino acids of a transmembrane segment,
s) the agent is not linked to a sortase transfer signature that is within 1, 2, 3, 4, 5, 10, 20, 50, or 100 amino acids of the agent,
t) at least 10%, 20%, 30%, 40%, 50%, 60%, 70%, 80%, 90%, 95%, or 99% of agents on the cell are not linked to a sortase transfer signature that is within 1, 2, 3, 4, 5, 10, 20, 50, or 100 amino acids of the agent,
u) the click signature is not linked to a sortase transfer signature that is within 1, 2, 3, 4, 5, 10, 20, 50, or 100 amino acids of the click signature,
v) at least 10%, 20%, 30%, 40%, 50%, 60%, 70%, 80%, 90%, 95%, or 99% of click signatures on the cell are not linked to a sortase transfer signature that is within 1, 2, 3, 4, 5, 10, 20, 50, or 100 amino acids of the click signature,
w) the polypeptide, e.g., an endogenous polypeptide, to which the agent is linked does not have a sortase transfer signature at a position corresponding to the N or C terminus;
x) at least 1%, 5%, 10%, 20%, 30%, 40%, 50%, 60%, 70%, 80%, 90%, 95%, or 99% of agents on the cell are linked via an amino acid side chain of a protein comprised by the cell, e.g., a protein at the cell surface, wherein in an embodiment the side chain is a side chain of lysine, cysteine, aspartic acid, or glutamic acid, linked such that at least one atom of an amino acid side chain is disposed between the agent and the backbone of the protein,
y) the agent is connected to a polypeptide (e.g., endogenous protein) on the cell surface,
z) the functionalized cell was not contacted with a sortase,
aa) the functionalized cell does not comprise a sortase transfer signature that comprises a bond that was formed extracellularly,
bb) at least 10%, 20%, 30%, 40%, 50%, 60%, 70%, 80%, 90%, 95%, or 99% of click signatures on the cell were produced by reacting the cell with a coupling reagent, or
cc) wherein the cell is made by a method that does not comprise contacting the cell with a non-natural sugar, e.g., a sugar comprising a click handle, or a combination thereof.

In some embodiments, the cell comprises over 1,000, 5,000, 5,000, 10,000, 50,000, 100,000, 200,000, 300,000, 400,000, or 500,000, copies of the agent.

In some embodiments:
i) the agent has a clearance rate wherein at least 20% of the agent remains in the circulatory system of the subject over 1, 2, 3, 4, 5, 6, or 7 days,
ii) the population of cells has a clearance rate wherein at least 20% of the agent remains in the circulatory system of the subject over 1, 2, 3, 4, 5, 6, or 7 days,
iii) the population of cells has a clearance rate wherein at least 20% of the functional erythroid cells remain in the circulatory system of the subject over 1, 2, 3, 4, 5, 6, or 7 days;
iv) the agent has a clearance rate wherein at least 20% of the agent that is in the circulatory system of the subject after 1 day remains in the circulatory system after another 1, 2, 3, 4, 5, 6, 7, 14, or 21 days;
iv) the population of cells has a clearance rate wherein at least 20% of the agent that is in the circulatory system of the subject after 1 day remains in the circulatory system after another 1, 2, 3, 4, 5, 6, 7, 14, or 21 days;
iv) the population of cells has a clearance rate wherein at least 20% of the population of cells that is in the circulatory system of the subject after 1 day remains in the circulatory system after another 1, 2, 3, 4, 5, 6, 7, 14, or 21 days;

In some embodiments, at least at least 50%, 60%, 70%, 80%, 90%, 95%, 97%, 98%, or 99%, of the erythroid cells of the population are enucleated.

In some embodiments, the cells are not hypotonically loaded cells.

In some embodiments, the enucleated erythroid cell has one or more of the following characteristics:

a) an osmotic fragility of less than 50% cell lysis at 0.3%, 0.35%, 0.4%, 0.45%, or 0.5% NaCl;
b) a cell volume of about 10-200 fL or a cell diameter of between about 1 micron and about 20 microns, between about 2 microns and about 20 microns, between about 3 microns and about 20 microns, between about 4 microns and about 20 microns, between about 5 microns and about 20 microns, between about 6 microns and about 20 microns, between about 5 microns and about 15 microns, or between about 10 microns and about 30 microns;
c) greater than 1%, 2%, 3%, 4%, 5%, 6%, 7%, 8%, 9% or 10% fetal hemoglobin; or at least about 20, 25, or 30 pg/cell of hemoglobin; or
d) phosphatidylserine content of the outer leaflet is less than 30%, 25%, 20%, 15%, 10%, or 5% as measured by Annexin V staining.

In some embodiments, the residual linker or click signature is within 1, 2, 5, 10, 20, or 50 atoms of an amino acid (e.g., a canonical amino acid) of a polypeptide on the cell. In some embodiments, the residual linker or click signature is not within 1, 2, 5, 10, 20, or 50 atoms of a carbohydrate moiety of the cell. In some embodiments, the agent is linked to a polypeptide that is not glycosylated. In some embodiments, the agent is linked to an amino acid side chain, N-terminus, or C-terminus of a polypeptide that is glycosylated.

In some embodiments, the residual linker is not within 1, 2, 5, 10, 20, or 50 atoms of a mannose moiety on the cell. In some embodiments, at least 10%, 20%, 30%, 40%, 50%, 60%, 70%, 80%, 90%, 95%, or 99% of residual linkers or click signatures on the cell are not within 1, 2, 5, 10, 20, or 50 atoms of a mannose moiety on the cell. In some embodiments, the residual linker are linked to at least two (e.g., 3, 4, 5, or more) types of sugar on the cell. For instance, a first residual linker can be within 1, 2, 5, 10, 20, or 50 atoms of a first sugar moiety on the cell, and a second residual linker can be within 1, 2, 5, 10, 20, or 50 atoms of a second sugar moiety on the cell.

In some embodiments, the cell is not genetically engineered.

In some embodiments, the cell does not comprise a non-canonical amino acid. In some embodiments, less than 1%, 0.1%, 0.01%, 0.001%, or 0.0001% of amino acids in the cell are non-canonical amino acids.

The disclosure contemplates all combinations of any one or more of the foregoing aspects and/or embodiments, as well as combinations with any one or more of the embodiments set forth in the detailed description and examples.

Although methods and materials similar or equivalent to those described herein can be used in the practice or testing of the present invention, suitable methods and materials are described below. All publications, patent applications, patents, and other references (e.g., sequence database reference numbers) mentioned herein are incorporated by reference in their entirety. For example, all GenBank, Unigene, NCBI, and Entrez sequences referred to herein, e.g., in any Table herein, are incorporated by reference. Unless otherwise specified, the sequence accession numbers specified herein, including in any Table herein, refer to the database entries current as of Aug. 7, 2017. When one gene or protein references a plurality of sequence accession numbers, all of the sequence variants are encompassed.

BRIEF DESCRIPTION OF THE DRAWINGS

FIG. 7A, high dose ASNase mRBCs; FIG. 7B, low dose ASNase mRBCs.

FIG. 8A, IL-2 secretion; FIG. 8B, interferon-γ secretion.

FIG. 9A, chemical structure of exo(BCN)-lysine; FIG. 9B, western blot showing that clicked mouse 41BBL was produced at concentrations of exo(BCN)-lysine of 1 mM or above.

DETAILED DESCRIPTION OF THE INVENTION

Figure 1:
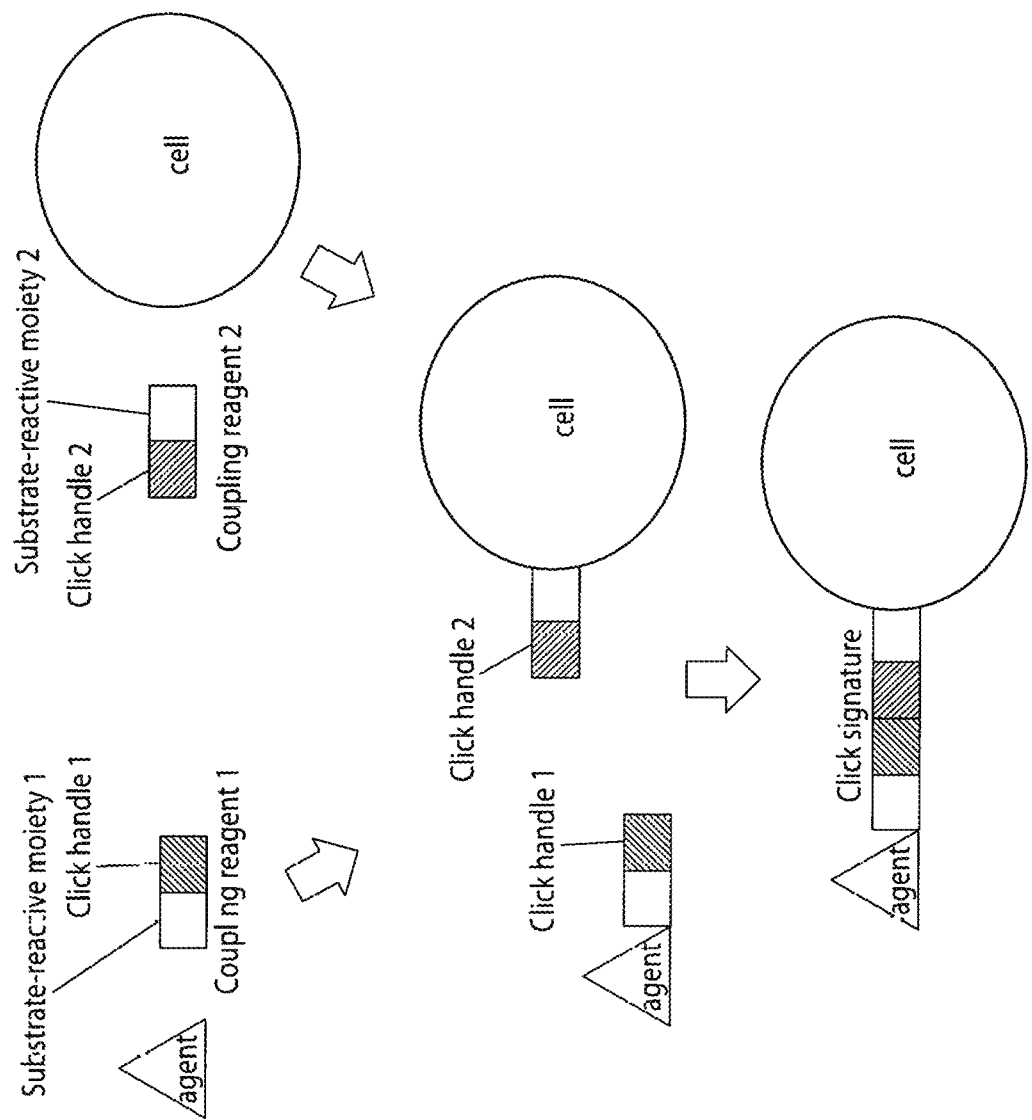
FIG. 1 is a diagram showing a method of clicking an agent onto a cell. An activated agent can be made, e.g., by contacting an agent with a first coupling reagent having a first substrate reactive moiety and a first coupling moiety which is a click handle, and allowing the first substrate reactive moiety to react with the agent. An activated cell can be made, e.g., by contacting a cell with a second coupling reagent having a second substrate reactive moiety and a second coupling moiety which is a click handle, and allowing the second substrate reactive moiety to react with the cell. The activated agent and activated cell are then combined under conditions that allow the first click handle to react with the second click handle, producing a residual linker comprising a click signature.

Described herein are compositions and methods that include functionalization of erythroid cells using selective, biocompatible reactions to couple the cells with an agent (e.g., a peptidic agent) of interest. In some embodiments, the reactions are cycloaddition reactions (e.g., a Huisgen 1,3-dipolar cycloaddition reaction) using reagents that are water-soluble and membrane impermeable.

Definitions

A "click signature," as that term is used herein, refers to a plurality of atoms disposed between and covalently linking entity A and entity B, wherein the click signature is formed as the product of a click reaction that links entity A and entity B. In an embodiment the click signature has the structure of a click signature that is formed as the product of a click reaction that links entity A and entity B, but is not limited a click signature made by any particular process, e.g., not limited to a click signature formed by a click reaction, but can be formed or provided by another process. In an embodiment, the click signature is an alkyne/azide click signature, e.g., the click signature comprises a triazole.

A "click reaction", as that term is used herein, refers to a range of reactions used to covalently link a first and a second moiety, for convenient production of linked products. It typically has one or more of the following characteristics: it is fast, is specific, is high-yield, is efficient, is spontaneous, does not significantly alter biocompatibility of the linked entities, has a high reaction rate, produces a stable product, favors production of a single reaction product, has high atom economy, is chemoselective, is modular, is stereoselective, is insensitive to oxygen, is insensitive to water, is high purity, generates only inoffensive or relatively non-toxic byproducts that can be removed by nonchromatographic methods (e.g., crystallization or distillation), needs no solvent or can be performed in a solvent that is benign or physiologically compatible, e.g., water, stable under physiological conditions. Examples include an alkyne/azide reaction, a diene/dienophile reaction, or a thiol/alkene reaction. Other reactions can be used. In some embodiments, the click reaction is fast, specific, and high-yield. For instance, in embodiments, a fast click reaction has a second order forward rate constant of 10-200 $M^{-1} s^{-1}$, 1-20 $M^{-1} s^{-1}$, or at least 1, 2, 3, 5, 10, 20, 50, 60, 100, 200, 500, 1E3, 2E3, 5E3, 1E4, 2E4, 5E4, 1E5, 2E5, 5E5, or 1E6 $M^{-1} s^{-1}$, e.g., at 20° C. in PBS. In some embodiments, a specific click reaction is one in which, when an unmodified cell (e.g., a human red blood cell isolated from peripheral circulation) is contacted with an agent having a click handle, less than 10%, 5%, 4%, 3%, 2%, or 1% of the cells are detectably linked to the agent, e.g., after a reaction time of 1 hour at 20° C. in PBS, e.g., in an assay of Example 21. In some embodiments, a high-yield click reaction is one which has at least 75%, 80%, 85%, 90%, 95%, 96%, 97%, 98%, or 99% yield, e.g., for a reaction time of 1 hour at 20° C. in PBS.

A "click handle," as that term is used herein, refers to a chemical moiety that is capable of reacting with a second click handle in a click reaction to produce a click signature. In embodiments, a click handle is comprised by a coupling reagent, and the coupling reagent may further comprise a substrate reactive moiety.

As used herein, a "sortase transfer signature" is a sequence that can be created by a sortase reaction that links a first sortase recognition motif with a second sortase recognition motif, wherein the sortase transfer signature comprises the amino acid sequence of the first sortase recognition motif and the amino acid sequence second recognition motif, minus any amino acids (e.g., Gly-Gly) removed during the sortase reaction. For instance, a sortase-mediated reaction of LPXTGG (SEQ ID NO: 2) with $(G)_n$ can produce a sortase transfer signature of $LPXT(G)_n$ (SEQ ID NO: 1).

Cells

The present invention features compositions comprising functionalized cells and methods of use thereof. In embodiments, the cells comprise erythroid cells. In embodiments, the cell is other than a platelet, platelet precursor, or platelet progenitor. In embodiments, the cells are nucleated or enucleated. In embodiments, the cells are eukaryotic cells, e.g., mammalian cells, e.g., human cells. In embodiments, the cells comprise T cells (e.g., CD4 T cells or CD8 T cells), B cells, natural killer cells, natural killer T cells, Myeloid Cells, Dendritic Cells, Platelets, or Neutrophils. In embodiments, the cells comprise endoderm-derived cells, ectoderm-derived cells, or mesoderm-derived cells. In embodiments, the cells comprise stem cells, mesenchymal stem cells, neural stem cells, cardiomyocytes, cells for allogeneic transplant, cells for xenogeneic transplant, or pancreatic beta cells.

Erythroid Cells

The present invention features compositions comprising functionalized erythroid cells and methods of use thereof. "Erythroid cells," as used herein, are cells of the erythrocytic series including hematopoietic stem cells (HSCs), and nucleated and enucleated red blood cell precursors, enucleated red blood cells, and any intermediates between HSCs and enucleated red blood cells. In an embodiment, an erythroid cell is a proerythroblast, basophilic erythroblast, polychromatophilic erythroblast, orthochromatic erythroblast, reticulocyte, and erythrocyte. In an embodiment, an erythroid cell is a cord blood stem cell, a CD34+ cell, a hematopoietic stem cell (HSC), a spleen colony forming (CFU-S) cell, a common myeloid progenitor (CMP) cell, a blastocyte colony-forming cell, a burst forming unit-erythroid (BFU-E), a megakaryocyte-erythroid progenitor (MEP) cell, an erythroid colony-forming unit (CFU-E), a reticulocyte, an erythrocyte, an induced pluripotent stem cell (iPSC), a mesenchymal stem cell (MSC), a polychromatic normoblast, an orthochromatic normoblast, or a combination thereof.

In embodiments, the erythroid cells are, or are derived from, immortal or immortalized cells. For example, immortalized erythroblast cells can be generated by retroviral transduction of CD34+ hematopoietic progenitor cells to express Oct4, Sox2, Klf4, cMyc, and suppress TP53 (e.g., as described in Huang et al. (2013) Mol Ther, epub ahead of print September 3).

In embodiments, the erythroid cells may be intended for autologous use or provide a source for allogeneic transfusion. In some embodiments, erythroid cells are cultured. In an embodiment an erythroid cell is an enucleated red blood cell.

In embodiments, an erythroid cell is obtained from a biological sample, e.g., erythrocytes from human blood, or HSCs from bone marrow.

In embodiments, an erythroid cell is obtained from an ex-vivo or in vitro process, e.g., whereby precursor cells, e.g., hematopoietic stem cells (e.g., human hematopoietic stem cells isolated from bone marrow, cytokine-stimulated peripheral blood or umbilical cord blood) are expanded and or differentiated and enucleated ex vivo to produce, e.g., reticulocytes. Ex vivo methods of manufacturing enucleated erythroid cells (e.g., reticulocytes) from stem cells are described, e.g., in Migliaccio and Palis (2011) Drug Discov Today Dis Mech. 8(1-2): e3-e8; WO2015/073587 and WO2015/153102, each of which is incorporated by reference in its entirety. Erythroid cells, e.g., reticulocytes, prepared via this process may be functionalized according to the methods described herein.

In an embodiment an enucleated cell is a cell that has lost its nucleus through differentiation from a precursor cell, e.g., a hematopoietic stem cell (e.g., a CD34+ cell), a common myeloid progenitor (CMP), a megakaryocyte erythrocyte progenitor cell (MEP), a burst-forming unit erythrocyte (BFU-E), a colony-forming unit erythrocyte (CFU-E), a pro-erythroblast, an early basophilic erythroblast, a late basophilic erythroblast, a polychromatic erythroblast, or an orthochromatic erythroblast, or an induced pluripotent cell, into a reticulocyte or mature red blood cell. In an embodiment an enucleated cell is a cell that has lost its nucleus through in vitro differentiation from a precursor cell, e.g., a hematopoietic stem cell (e.g., a CD34+ cell), a common myeloid progenitor (CMP), a megakaryocyte erythrocyte progenitor cell (MEP), a burst-forming unit erythrocyte (BFU-E), a colony-forming unit erythrocyte (CFU-E), a pro-erythroblast, an early basophilic erythroblast, a late basophilic erythroblast, a polychromatic erythroblast, or an orthochromatic erythroblast, or an induced pluripotent cell into a reticulocyte or mature red blood cell.

An erythroid cell used in the functionalization methods described herein may be unmodified or may be modified, e.g., genetically engineered (e.g., genetically engineered to express an exogenous protein); may be encapsulated, e.g., hypotonically loaded, with an exogenous protein. An erythroid cell used in the treatment methods described herein may be autologous, allogeneic, or xenogeneic.

Exemplary cells for use in preparations, compounds, methods and kits described herein are described herein. In an embodiment, the cell, e.g., erythroid cell, e.g., erythrocyte, comprises one or more of the following properties: a) it is obtained from blood, an in vitro culture, or was differentiated from a more primitive cell type in vitro, e.g., a hematopoietic stem cell; b) it has been hypotonically loaded with an agent; or c) it is a genetically engineered erythroid cell, e.g., expressing an exogenous agent, e.g., a polypeptide.

In an embodiment, the cell is differentiated from a more primitive cell type in vitro, e.g., a hematopoietic stem cell.

In an embodiment, the cell is a genetically engineered erythroid cell, e.g., expressing an exogenous agent, e.g., a polypeptide.

In an embodiment, the cell is an erythrocyte obtained from blood.

In an embodiment, the cell has been hypotonically loaded with an agent.

In an embodiment, the cell is from an in vitro culture.

In an embodiment, the cell is a genetically engineered erythroid cell, e.g., expressing an exogenous agent, e.g., a polypeptide.

Physical Characteristics of Enucleated Erythroid Cells

In some embodiments, the enucleated erythroid cells described herein have one or more (e.g., 2, 3, 4, or more) physical characteristics described herein, e.g., osmotic fragility, cell size, hemoglobin concentration, or phosphatidylserine content. While not wishing to be bound by theory, in some embodiments an enucleated erythroid cell described herein has physical characteristics that resemble a wild-type, untreated erythroid cell. In contrast, a hypotonically loaded erythroid cell sometimes displays aberrant physical characteristics such as increased osmotic fragility, altered cell size, reduced hemoglobin concentration, or increased phosphatidylserine levels on the outer leaflet of the cell membrane.

In some embodiments, the erythroid cell is in a composition that lacks a stabilizer.

Osmotic Fragility

In some embodiments, the enucleated erythroid cell exhibits substantially the same osmotic membrane fragility as an isolated, uncultured enucleated erythroid cell. In some embodiments, the population of enucleated erythroid cells has an osmotic fragility of less than 50% cell lysis at 0.3%, 0.35%, 0.4%, 0.45%, or 0.5% NaCl. Osmotic fragility is determined, in some embodiments, using the method of Example 59 of WO2015/073587.

Cell Size

In some embodiments, the enucleated erythroid cell has approximately the diameter or volume as a wild-type, untreated erythroid cell.

In some embodiments, the population of erythroid cells has an average diameter of about 4, 5, 6, 7, or 8 microns, and optionally the standard deviation of the population is less than 1, 2, or 3 microns. In some embodiments, the one or more erythroid cell has a diameter of about 4-8, 5-7, or about 6 microns. In some embodiments, the diameter of the erythroid cell is less than about 1 micron, larger than about 20 microns, between about 1 micron and about 20 microns, between about 2 microns and about 20 microns, between about 3 microns and about 20 microns, between about 4 microns and about 20 microns, between about 5 microns and about 20 microns, between about 6 microns and about 20 microns, between about 5 microns and about 15 microns or between about 10 microns and about 30 microns. Cell diameter is measured, in some embodiments, using an Advia 120 hematology system.

In some embodiment the volume of the mean corpuscular volume of the erythroid cell is greater than 10 fL, 20 fL, 30 fL, 40 fL, 50 fL, 60 fL, 70 fL, 80 fL, 90 fL, 100 fL, 110 fL, 120 fL, 130 fL, 140 fL, 150 fL, or greater than 150 fL. In one embodiment the mean corpuscular volume of the erythroid cell is less than 30 fL, 40 fL, 50 fL, 60 fL, 70 fL, 80 fL, 90 fL, 100 fL, 110 fL, 120 fL, 130 fL, 140 fL, 150 fL, 160 fL, 170 fL, 180 fL, 190 fL, 200 fL, or less than 200 fL. In one embodiment the mean corpuscular volume of the erythroid cells is between 80-100, 100-200, 200-300, 300-400, or 400-500 femtoliters (fL). In some embodiments, a population of erythroid cells has a mean corpuscular volume set out in this paragraph and the standard deviation of the population is less than 50, 40, 30, 20, 10, 5, or 2 fL. The mean corpuscular volume is measured, in some embodiments, using a hematological analysis instrument, e.g., a Coulter counter.

Hemoglobin Concentration

In some embodiments, the enucleated erythroid cell has a hemoglobin content similar to a wild-type, untreated erythroid cell. In some embodiments, the erythroid cells comprise greater than 1%, 2%, 3%, 4%, 5%, 6%, 7%, 8%, 9% or greater than 10% fetal hemoglobin. In some embodiments, the erythroid cells comprise at least about 20, 22, 24, 26, 28, or 30 pg, and optionally up to about 30 pg, of total hemoglobin. Hemoglobin levels are determined, in some embodiments, using the Drabkin's reagent method of Example 33 of WO2015/073587.

Phosphatidylserine Content

In some embodiments, the enucleated erythroid cell has approximately the same phosphatidylserine content on the outer leaflet of its cell membrane as a wild-type, untreated erythroid cell. Phosphatidylserine is predominantly on the inner leaflet of the cell membrane of wild-type, untreated erythroid cells, and hypotonic loading can cause the phosphatidylserine to distribute to the outer leaflet where it can trigger an immune response. In some embodiments, the population of erythroid cells comprises less than about 30, 25, 20, 15, 10, 9, 8, 6, 5, 4, 3, 2, or 1% of cells that are positive for Annexin V staining. Phosphatidylserine exposure is assessed, in some embodiments, by staining for Annexin-V-FITC, which binds preferentially to PS, and measuring FITC fluorescence by flow cytometry, e.g., using the method of Example 54 of WO2015/073587.

Other Characteristics

In some embodiments, the population of erythroid cells comprises at least about 50%, 60%, 70%, 80%, 90%, or 95% (and optionally up to 90 or 100%) of cells that are positive for GPA. The presence of GPA is detected, in some embodiments, using FACS.

In some embodiments, the enucleated erythroid cells have a half-life of at least 30, 45, or 90 days in a subject.

In some embodiments, a population of cells comprising erythroid cells comprises less than about 10, 5, 4, 3, 2, or 1% echinocytes.

In some embodiments, an erythroid cell is enucleated. In some embodiments, a cell, e.g., an erythroid cell, contains a nucleus that is non-functional, e.g., has been inactivated.

Universal Donor Erythroid Cells

In some embodiments, erythroid cells described herein are autologous or allogeneic to the subject to which the cells will be administered. For example, erythroid cells allogeneic to the subject include one or more of blood type specific erythroid cells (e.g., the cells can be of the same blood type as the subject) or one or more universal donor erythroid cells. In some embodiments, the enucleated erythroid cells described herein have reduced immunogenicity compared to a reference cell, e.g., have lowered levels of one or more blood group antigens.

Where allogeneic cells are used for transfusion, a compatible ABO blood group can be chosen to prevent an acute intravascular hemolytic transfusion reaction. The ABO blood types are defined based on the presence or absence of the blood type antigens A and B, monosaccharide carbohydrate structures that are found at the termini of oligosaccharide chains associated with glycoproteins and glycolipids on the surface of the erythrocytes (reviewed in Liu et al., Nat. Biotech. 25:454-464 (2007)). Because group O erythrocytes contain neither A nor B antigens, they can be safely transfused into recipients of any ABO blood group, e.g., group A, B, AB, or O recipients. Group O erythrocytes are considered universal and may be used in all blood transfusions. Thus, in some embodiments, an erythroid cell described herein is type O. In contrast, group A erythroid cells may be given to group A and AB recipients, group B erythroid cells may be given to group B and AB recipients, and group AB erythroid cells may be given to AB recipients.

In some instances, it may be beneficial to convert a non-group O erythroid cell to a universal blood type. Enzymatic removal of the immunodominant monosaccharides on the surface of group A and group B erythrocytes may be used to generate a population of group O-like erythroid cells (See, e.g., Liu et al., Nat. Biotech. 25:454-464 (2007)). Group B erythroid cells may be converted using an α-galactosidase derived from green coffee beans. Alternatively or in addition, α-N-acetylgalactosaminidase and α-galactosidase enzymatic activities derived from *E. meningosepticum* bacteria may be used to respectively remove the immunodominant A and B antigens (Liu et al., Nat. Biotech. 25:454-464 (2007)), if present on the erythroid cells. In one example, packed erythroid cells isolated as described herein, are incubated in 200 mM glycine (pH 6.8) and 3 mM NaCl in the presence of either α-N-acetylgalactosaminidase and α-galactosidase (about 300 pg/ml packed erythroid cells) for 60 min at 26° C. After treatment, the erythroid cells are washed by 3-4 rinses in saline with centrifugation and ABO-typed according to standard blood banking techniques.

While the ABO blood group system is the most important in transfusion and transplantation, in some embodiments it can be useful to match other blood groups between the erythroid cells to be administered and the recipient, or to select or make erythroid cells that are universal for one or more other (e.g., minor) blood groups. A second blood group is the Rh system, wherein an individual can be Rh+ or Rh−. Thus, in some embodiments, an erythroid cell described herein is Rh−. In some embodiments, the erythroid cell is Type O and Rh−.

In some embodiments, an erythroid cell described herein is negative for one or more minor blood group antigens, e.g., Le(a−b−) (for Lewis antigen system), Fy(a−b−) (for Duffy system), Jk(a−b−) (for Kidd system), M−N− (for MNS system), K−k− (for Kell system), Lu(a−b−) (for Lutheran system), and H-antigen negative (Bombay phenotype), or any combination thereof. In some embodiments, the erythroid cell is also Type O and/or Rh−. Minor blood groups are described, e.g., in Agarwal et al "Blood group phenotype frequencies in blood donors from a tertiary care hospital in north India" Blood Res. 2013 March; 48(1): 51-54 and Mitra et al "Blood groups systems" Indian J Anaesth. 2014 September-October; 58(5): 524-528, each of which is incorporated herein by reference in its entirety.

Erythroid Cell Compositions

In some embodiments, the population of erythroid cells comprises at least 30, 35, 40, 45, 50, 55, 60, 65, 70, 75, 80, 85, 90, 95, or 98% (and optionally up to about 80, 90, or 100%) enucleated erythroid cells. In some embodiments, the population of erythroid cells contains less than 1% live nucleated cells, e.g., contains no detectable live nucleated cells. Enucleation is measured, in some embodiments, by FACS using a nuclear stain. In some embodiments, at least 30, 35, 40, 45, 50, 55, 60, 65, 70, 75, or 80% (and optionally up to about 70, 80, 90, or 100%) of erythroid cells in the population comprise one or more (e.g., 2, 3, 4 or more) of the agents. Presence of the agent is measured, in some embodiments, by FACS using a labeled protein (e.g., antibody) that binds the agent. In some embodiments, at least 30, 35, 40, 45, 50, 55, 60, 65, 70, 75, or 80% (and optionally up to about 70, 80, 90, or 100%) of erythroid cells in the population are enucleated and comprise one or more agents. In some embodiments, the population of erythroid cells comprises about $1\times10^9$-$2\times10^9$, $2\times10^9$-$5\times10^9$, $5\times10^9$-$1\times10^{10}$, $1\times10^{10}$-$2\times10^{10}$, $2\times10^{10}$—$5\times10^{10}$, $5\times10^{10}$-$1\times10^{11}$, $1\times10^{11}$-$2\times10^{11}$, $2\times10^{11}$-$5\times10^{11}$, $5\times10^{11}$-$1\times10^{12}$, $1\times10^{12}$-$2\times10^{12}$, $2\times10^{12}$-$5\times10^{12}$, or $5\times10^{12}$-$1\times10^{13}$ cells.

Clickable Format Cells

In some embodiments, the cell comprises a conjugation agent without requiring a step of chemically reacting the cell with the conjugation agent. For example, the cell can be contacted with a molecule that comprises a metabolite (e.g., an amino acid or sugar) and a coupling moiety (e.g., a click handle). The cell is then allowed to incorporate the metabolite, e.g., into proteins or carbohydrates, e.g., on the surface of the cell. The metabolite can be, e.g., a non-canonical amino acid. In embodiments, the metabolite is incorporated using a tRNA/amino-acyl-tRNA-synthetase pair that directs the metabolite into a specific position, e.g., one encoded by an Amber stop codon. The resulting activated cell comprises the coupling moiety (e.g., click handle). The activated cell can then be contacted with an activated agent, e.g., an activated agent described herein.

A variety of molecules that comprise a metabolite and a coupling moiety can be used. For instance, in embodiments, the molecule is chosen from:

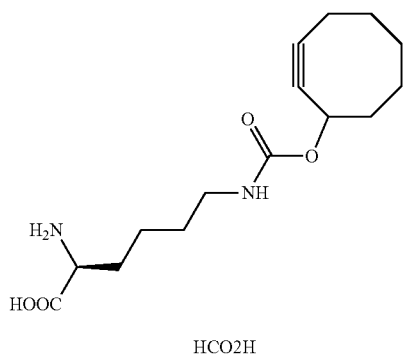 [SMILES: N[C@@H](CCCCNC(=O)OC1C#CCCCCC1)C(=O)O ; "HCO2H"]

SCO-Lysine, e.g., for use in a strain-promoted alkyne-azide cycloaddition (SPAAC) reaction;

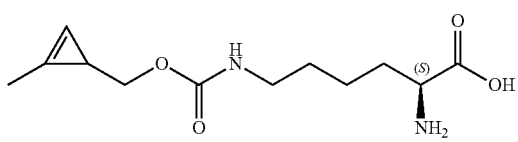

Cyclopropene lysine, e.g., for use in a strain-promoted inverse-electron-demand Diels-Alder cycloaddition (SPIEDAC) reaction;

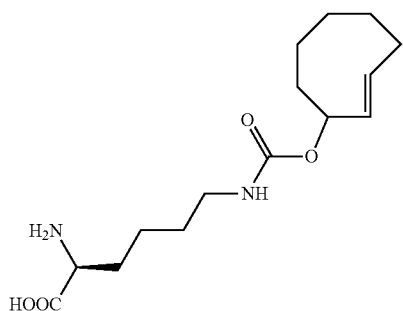 [SMILES: N[C@@H](CCCCNC(=O)OC1/C=C/CCCCC1)C(=O)O]

TCO*A-Lysine, e.g., for use in a SPIEDAC reaction;

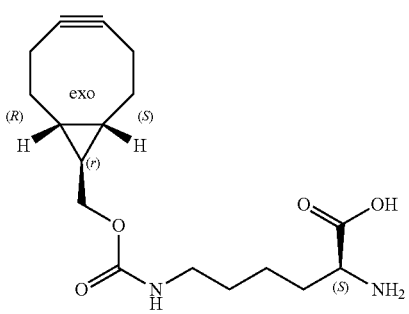

Exo-BCN-Lysine, e.g., for use in a SPAAC reaction;

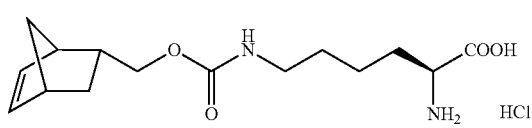 [SMILES: N[C@@H](CCCCNC(=O)OCC1CC2C=CC1C2)C(=O)O ; Cl]

NBO-Lysine, e.g., for use in a SPIEDAC reaction;

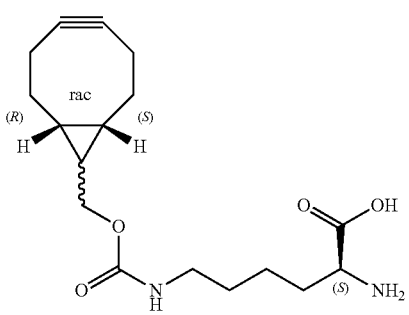

rac-BCN-Lysine, e.g., for use in a SPAAC reaction;

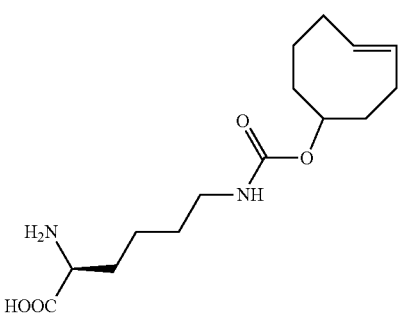 [SMILES: N[C@@H](CCCCNC(=O)OC1CC/C=C/CCC1)C(=O)O]

TCO-Lysine, e.g., for use in a SPIEDAC reaction;

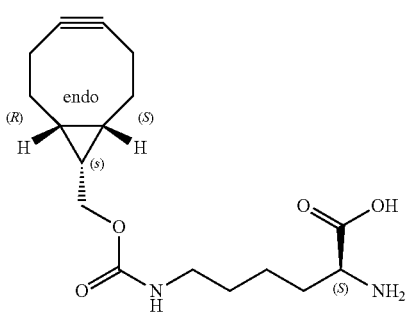

Endo-BCN-Lysine, e.g., for use in a SPAAC reaction

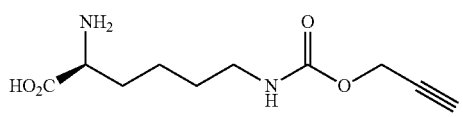

PrK-HCL-salt, e.g., for use in a SPAAC or SPIEDAC reaction;

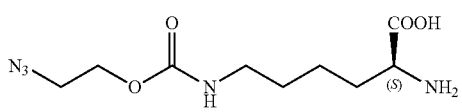

N3-Lysine, e.g., for use in a SPAAC or SPIEDAC reaction

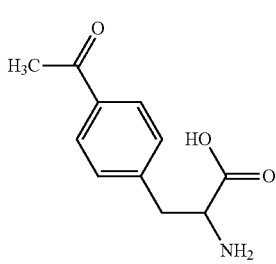

p-acetylphenylalanine, e.g., for use with a site-specific oxime ligation (e.g., mediated by DBCO-amine), followed by SPAAC

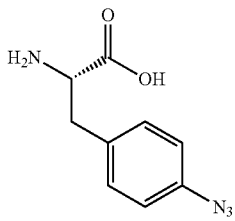 [SMILES: [N-]=[N+]=Nc1ccc(C[C@H](N)C(=O)O)cc1]

p-azidomethylphenylalanine, e.g., for use in a SPAAC or SPIEDAC reaction; or

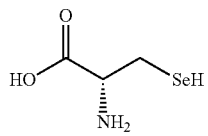

seleno-cysteine, e.g., for reaction with maleimide.

Coupling Reagents

Described herein are compositions of erythroid cells functionalized with an agent, wherein the cells and the agent are linked through a set of bispecific coupling reagents. In some embodiments, a set of bispecific coupling reagents comprises a first coupling reagent and a second coupling reagent. The first coupling reagent comprises a coupling moiety, e.g., an alkyne moiety, that reacts specifically with the coupling moiety, e.g, an azide, on the second coupling reagent. The coupling moieties do not self-react. In embodiments, the coupling moiety is a click handle. A click handle may comprise an azide or an alkyne.

Each coupling reagent also comprises a substrate reactive moiety, suitable, e.g., for binding (e.g., covalently) to a substrate of interest, e.g., an erythroid cell, or an agent for attachment to an erythroid cell, e.g., a polypeptide, lipid, nucleic acid, sugar, drug, small molecule. In embodiments, the substrate reactive moiety is capable of reacting non-enzymatically with a substrate. In embodiments, the substrate reactive moiety is capable of reacting with a substrate other than in a sortase reaction.

In embodiments, a coupling reagent is capable of covalently linking a first entity (e.g., a cell) with a second entity (e.g., an exogenous polypeptide).

The first coupling reagent can be linked via its substrate reactive moiety to a first substrate, e.g., an erythroid cell. The second coupling reagent can be linked via its substrate reactive moiety to a second substrate, e.g., a polypeptide or drug. The thus derivatized substrates can then be linked to one another.

Linkage of the two substrates typically results in a residual linker between the first and second substrate. For example, in the case of coupling reagents comprising an azide and an alkyne, a residual linker may be formed comprising a triazole (e.g., a 1,2,3-triazole). Exemplary coupling reagents include alkyne coupling reagents (KR) and azide coupling reagents (AR).

In some embodiments, the coupling reagent comprises an alkyne coupling reagent. In some embodiments, the alkyne coupling reagent comprises a propargyl moiety or a cyclooctynyl moiety. Exemplary alkyne coupling reagents include diarylcyclooctyne (DBCO)-sulfo-NHS-ester, diarylcyclooctyne (DBCO)-PEG-NHS-ester, diarylcyclooctyne (DBCO)-C6-NHS-ester, diarylcyclooctyne (DBCO)-NHS-ester, diarylcyclooctyne (DBCO)-amine, diarylcyclooctyne (DBCO)-acid, sulfo diarylcyclooctyne (DBCO)-maleimide, diarylcyclooctyne (DBCO)-maleimide, bis-sulfone-PEG-diarylcyclooctyne (DBCO), propargyl-NHS ester, propargyl-maleimide, alkyne-PEG-NHS ester, alkyne-PEG-maleimide, or a derivative thereof.

In some embodiments, the coupling reagent comprises an azide coupling reagent. In some embodiments, the azide coupling reagent comprises an azidoalkyl moiety, azidoaryl moiety, or an azidoheteroaryl moiety. Exemplary azide coupling reagents include 3-azidopropionic acid sulfo-NHS ester, azidoacetic acid NHS ester, azido-PEG-NHS ester, azidopropylamine, azido-PEG-amine, azido-PEG-maleimide, bis-sulfone-PEG-azide, or a derivative thereof.

Coupling reagents may also comprise an alkene moiety, e.g., a transcycloalkene moiety, an oxanorbornadiene moiety, or a tetrazine moiety. Additional coupling reagents can be found in *Click Chemistry Tools* (https://clickchemistry-tools.com/), Lahann, J (ed) (2009) *Click Chemistry for Biotechnology and Materials Science*, McKay et al, "Click chemistry in complex mixtures: bioorthogonal bioconjugation" Chem Biol. 2014 Sep. 18; 21(9):1075-101, Becer et al. "Click chemistry beyond metal-catalyzed cycloaddition" Angew Chem Int Ed Engl. 2009; 48(27):4900-8, and Hein et al. "Click chemistry, a powerful tool for pharmaceutical sciences" Pharm Res. 2008 October; 25(10):2216-30, each of which is incorporated herein by reference in its entirety.

In embodiments, the coupling reagent comprises a tetrazine moiety, e.g., for reaction with an alkene moiety. For instance, in embodiments, the tetrazine is a 1, 2, 4, 5 tetrazine and the alkene is a strained alkene. In embodiments, the alkene coupling reagent comprises a trans-cyclooctene, (E)-Cyclooct-4-enol, (E)-Cyclooct-4-enyl 2,5-dioxo-1-pyrrolidinyl carbonate, 5-Norbornene-2-acetic acid succinimidyl ester, 5-Norbornene-2-endo-acetic acid, TCO PEG4 succinimidyl ester, TCO-amine, or TCO-PEG3-maleimide. In embodiments, the tetrazine coupling reagent comprises (4-(1,2,4,5-Tetrazin-3-yl)phenyl)methanamine or 2,5-Dioxo-1-pyrrolidinyl 5-[4-(1,2,4,5-tetrazin-3-yl)benzylamino]-5-oxopentanoate, 5-[4-(1,2,4,5-Tetrazin-3-yl)benzylamino]-5-oxopentanoic acid. In embodiments, the tetrazine and alkene react in a Diels-Alder cycloaddition to yield a stable covalent linkage. In embodiments, a catalyst is not needed. In embodiments, the only byproduct is dinitrogen. In embodiments, the reaction at least one order of magnitude faster than azide-cyclooctyne based click chemistry. Without wishing to be bound by theory, tetrazine/alkene reactions can be used with low concentrations of reactant (e.g., the agent).

In some embodiments, the coupling moieties of each coupling reagent react via an azide-alkyne Huisgen cycloaddition. In some embodiments, an azide-alkyne Huisgen cycloaddition comprises a copper(I)-catalyzed azide-alkyne cycloaddition or a strain-promoted azide-alkyne cycloaddition.

In some embodiments, the coupling moieties of each coupling reagent react to form a heteroaryl, e.g., a triazole. In some embodiments, the triazole comprises a 1,2,3-triazole, e.g., a 1,4-disubstituted 1,2,3-triazole or a 1,5-disubstituted 1,2,3-triazole.

In some embodiments, the coupling reagent comprises a substrate reactive moiety to link the coupling reagent to an agent (e.g., an agent described herein). In some embodiments, the substrate reactive moiety reacts with a carbonyl, an ester, a carboxylic acid, an amine, or a sulfhydryl group. In some embodiments, the substrate reactive moiety comprises a succinimide (e.g., NHS-ester), a maleimide, an amine, a hydrazine, an alkoxyamine, a carboxylic acid, an aldehyde, a ketone, a disulfide, an acyl halide, an isothiocyanate, or a derivative thereof.

In some embodiments, the substrate reactive moiety comprises a linker. In some embodiments, the linker comprises a polyethylene glycol (PEG) moiety. In some embodiments, the linker is a straight chain. In some embodiments, the linker is a branched chain.

In some embodiments, the coupling reagent comprises an alkyne and reacts with an amine. In some embodiments, the coupling agent comprises a cyclooctyne and reacts with an amine. In some embodiments, the coupling agent is diarylcyclooctyne (DBCO)-sulfo-NHS-ester or diarylcyclooctyne (DBCO)-PEG5-NHS-ester.

In some embodiments, the coupling agent comprises an azide and reacts with an amine. In some embodiments, the coupling agent is 3-azidopropionic acid sulfo-NHS ester or azido-PEG4-NHS-ester.

In an embodiment, the coupling reagent is water soluble. In an embodiment, the coupling reagent is membrane impermeable, e.g., has sufficient charge to render it membrane impermeable. In an embodiment the coupling reagent is charged, e.g., positively charged or negatively charged. In an embodiment, the coupling reagent comprises a cationic moiety or an anionic moiety, e.g., a $SO_3$ moiety.

In some embodiments, the coupling agent comprises a detection agent, e.g., useful for detection of the functionalize erythroid cell. Exemplary detection agents may include a fluorescent molecule (e.g., a cyanine dye, e.g., Cy3, Cy 3.5, Cy5, Cy5.5, Cy7, or Cy7.5), a metal chelate, a contrast agent, a radionuclide, a positron emission tomography (PET) imaging agent, an infrared imaging agent, a near-IR imaging agent, a computer assisted tomography (CAT) imaging agent, a photon emission computerized tomography imaging agent (e.g., DIBO-DFO, where DFO chelates Zirconium-89), an X-ray imaging agent, or a magnetic resonance imaging (MRI) agent.

In an embodiment, a coupling reagent is a GMP grade material.

In some embodiments, the click reaction is a cycloaddition (e.g., a 1,3-dipolar cycloaddition or hetero-Diels-Alder cycloaddition), nucleophilic ring-opening (e.g., openings of strained heterocyclic electrophiles such as aziridines, epoxides, cyclic sulfates, aziridinium ions, and episulfonium ions), carbonyl chemistry of no-aldol type (e.g., formation of ureas, thioureas, hydrazones, oxime ethers, amides, or aromatic heterocycles), or an addition to a carbon-carbon multiple bond (e.g., epoxidation, aziridination, dihydroxylation, sulfenyl halide addition, nitosyl halide addition, or Michael addition). Examples of these types of click reaction are described in greater detail in Hein et al., Pharm. Res. 2008 October; 25(10):2216-2230, which is herein incorporated by reference in its entirety. In embodiments, the click reaction is a metal-free [3+2] cycloaddition reaction, Diels-Alder reaction, or thiol-alkene radical reaction. Examples of these types of click reaction are described in greater detail in Becer et al., Angew. Chem. Int. Ed. 2009, 48, 4900-4908, which is herein incorporated by reference in its entirety.

In an embodiment, the click signature is an alkyne/azide click signature (e.g., wherein the alkyne is a cyclooctyne, activated alkyne, or electron-deficient alkyne), e.g., the click signature comprises a triazole, e.g., a 1,2,3-triazole and/or a disubstituted triazole. In an embodiment, the click signature is a diene/dienophile click signature (e.g., wherein the dienophile comprises an alkene moiety), e.g., the click signature comprises a cycloalkene, e.g., a disubstituted alkene. In embodiments, the click signature is a tetrazine/alkene click signature, e.g., the click signature comprises a dihydropyrazine, e.g., a 1,2-dihydropyrazine. In embodiments, the click signature is a tetrazole/alkene click signature, e.g., the click signature comprises a diazole. In embodiments, the click signature is a dithioester/diene click signature, e.g., the click signature comprises a sulfur-containing ring, e.g., a tetrahdrothiophene, e.g., a disubstituted tetrahdrothiophene. In embodiments, the click signature is a dithioester/diene signature, e.g., the click signature comprises a sulfur-containing ring, e.g., a thiopyran. In embodiments, the click signature is a thiol/alkene click signature, e.g., the click signature comprises an alkyl sulfide.

In embodiments, the click reaction does not require a catalyst. In embodiments, the click reaction does not require copper ions, e.g., proceeds at substantially the same rate in the absence of copper ions as in the presence of copper ions, e.g., under conditions described in Tornoe, C. W. et al (2002). "Peptidotriazoles on Solid Phase: [1,2,3]-Triazoles by Regiospecific Copper(I)-Catalyzed 1,3-Dipolar Cycloadditions of Terminal Alkynes to Azides". In embodiments, the click reaction proceeds efficiently at a temperature of about 10-40, 20-40, 20-30, 20-25, 30-40, or 35-40, or about 37 C. In embodiments, the click reaction proceeds efficiently at a temperature of below 50, 45, 40, 35, 30, 25, or 20 C.

In embodiments, the activation barrier for a click reaction is 24-30, 25-29, or 26-28 kcal/mol, e.g., about 27.8 kcal/mol or 26 kcal/mol. In embodiments, the activation barrier for a click reaction is the same as or no less than 50%, 40%, 30%, 20%, or 10%, different from the activation barrier of a Huisgen Cu-catalyzed cycloaddition reaction between an azide and a terminal alkene, e.g., as described in Hein et al. Click chemistry, a powerful tool for pharmaceutical sciences" Pharm Res. 2008 October; 25(10):2216-30.

In embodiments, the click reaction is exergonic, e.g., having a ΔG° of between −10 and −100, −20 and −90, −30 and −70, −40 and −70, −50 and −60, or about −61 kcal/mol. In embodiments, the ΔG° for a click reaction is the same as or no less than 50%, 40%, 30%, 20%, or 10%, different from the ΔG° of a Huisgen Cu-catalyzed cycloaddition reaction between an azide and a terminal alkene.

In embodiments, the click reaction has a ΔG° of between −30 and −140, −40 and −130, −50 and −120, −60 and −110, −70 and −100, −80 and −90, or about 84 kJ/mol.

One example of a cycloaddition reaction is the Huisgen 1,3-dipolar cycloaddition of a dipolarophile with a 1,3 dipolar component that produce five membered (hetero) cycles. Examples of dipolarophiles are alkenes, alkynes, and molecules that possess related heteroatom functional groups, such as carbonyls and nitriles. Specifically, another example is the 2+3 cycloaddition of alkyl azides and acetylenes. Other cycloaddition reactions include Diels-Alder reactions of a conjugated diene and a dienophile (such as an alkyne or alkene). Examples of cycloaddition reactions are described, e.g., in U.S. Pat. No. 9,517,291, which is herein incorporated by reference in its entirety.

Other examples of click reactions include a hydrosilation reaction of H—Si and simple non-activated vinyl compounds, urethane formation from alcohols and isocyanates, Menshutkin reactions of tertiary amines with alkyl iodides or alkyl trifluoromethanesulfonates, Michael additions, e.g., the very efficient maleimide-thiol reaction, atom transfer radical addition reactions between —$SO_2Cl$ and an olefin ($R^1$, $R^2$—C≡C—$R^3$, $R^4$), metathesis, Staudinger reaction of phosphines with alkyl azides, oxidative coupling of thiols, nucleophilic substitution, especially of small strained rings like epoxy and aziridine compounds, carbonyl chemistry like formation of ureas, and addition reactions to carbon-carbon double bonds like dihydroxylation. Therefore, attached functionality may be chosen from acetylene bond, an azido-group, a nitrile group, acetylenic, amino group, phosphino group. The click chemistry reaction may result in the addition of a functional group selected from amino, primary amino, hydroxyl, sulfonate, benzotriazole, bromide, chloride, chloroformate, trimethylsilane, phosphonium bromide or bio-responsive functional group including polypeptides, proteins and nucleic acids.

Thus, suitable coupling reagents may comprise, for example, an amine, sulfate, thiol, hydroxyl, azide, alkyne, alkene, carboxyl groups aldehyde groups, sulfone groups, vinylsulfone groups, isocyanate groups, acid anhydride groups, epoxide groups, aziridine groups, episulfide groups, groups such as —CO$_2$N(COCH$_2$)2, —CO$_2$N(COCH$_2$)$_2$, —CO$_2$H, —CHO, —CHOCH$_2$, —N.dbd.C.dbd.O, —SO$_2$CH.dbd.CH$_2$, —N(COCH)$_2$, —S—S—(C$_5$H$_4$N) and groups of the following structures wherein X is halogen and R is hydrogen or C$_1$ to C$_4$ alkyl:

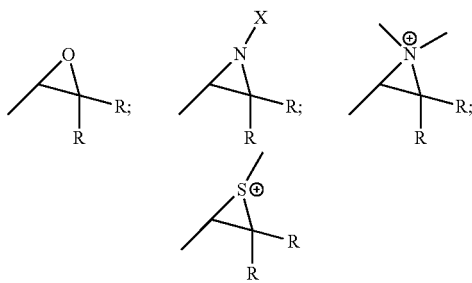

In some embodiments, a click reaction forms very energy-efficient carbon-heteroatom bonds, in particular a ring opening nucleophilic reaction or a cycloaddition reaction. A type of reaction which is widely represented in click chemistry is the abovementioned alkyne-azide cycloaddition catalyzed with Cu(I). Examples of click reactions are also described, e.g., in U.S. Pat. No. 9,453,843, which is herein incorporated by reference in its entirety.

Click chemistry may generate substances quickly and reliably by joining small modular units together (see, e.g., Kolb et al. (2001) Angewandte Chemie Intl. Ed. 40:2004-2011; Evans (2007) Australian J. Chem. 60:384-395; Carlmark et al. (2009) Chem. Soc. Rev. 38:352-362; each herein incorporated by reference in its entirety). Examples of click chemistry are described, e.g., in U.S. Pat. No. 8,912,323, which is herein incorporated by reference in its entirety.

Agents, e.g., Exogenous Polypeptide Agents

The present invention features compositions of erythroid cells functionalized with an agent, and methods, preparations, and kits comprising the same. Exemplary agents for use in the invention are described herein.

In an embodiment, the agent is an agent described in WO2015/15302; or in WO2015/073587, each of which is hereby incorporated by reference in its entirety.

In an embodiment, the agent comprises a peptidic agent, e.g., a polypeptide, an enzyme, or an antibody.

In an embodiment, the agent comprises an exogenous polypeptide, e.g., a polypeptide that is not produced by a wild-type cell of that type or is present at a lower level in a wild-type cell than in a cell containing the exogenous polypeptide. In some embodiments, an exogenous polypeptide is a polypeptide conjugated to the surface of the cell by chemical or enzymatic means. In some embodiments, an exogenous polypeptide is a polypeptide encoded by a nucleic acid that was introduced into the cell, which nucleic acid is optionally not retained by the cell.

In an embodiment, the agent comprises a cytokine, a receptor, a ligand, a hormone, a growth factor, a blood factor, a lysosomal storage enzyme, asparaginase, or a fragment of any of the foregoing comprising an extracellular domain, counterligand binding domain, or other biologically active domain.

In an embodiment, the agent comprises an antigen, e.g., a tumor antigen, and infectious disease antigen, and autoantigen.

In an embodiment, the agent comprises a lipid, nucleic acid, e.g. RNA, DNA, siRNA, sugar, drug, or small molecule.

In an embodiment, the agent comprises a polypeptide of greater than about 30, 50, 75, 100, 150, 200, 250, 300, 350, or 400 kilodaltons.

In an embodiment, the agent, e.g., a polypeptide, comprises post translational modification, e.g., a post translational modification that is not made by erythroid cells, or made inefficiently by erythroid cells.

In an embodiment, the agent, e.g., a polypeptide, is toxic to, or compromises the growth, function, life span, or development of an erythroid cell.

In an embodiment, the agent comprises a multimeric polypeptide, e.g., a dimer, e.g., a homodimer or heterodimer, a trimer, e.g., a homotrimer or heterotrimer, or a tetramer, e.g., a homotetramer or heterotetramer, e.g., an antibody or a cell surface receptor, e.g., a receptor for a disease vector, e.g., a virus, a drug, or a toxin.

In an embodiment, the agent comprises a polypeptide, e.g., a multimeric polypeptide, comprising a plurality of cysteine bridges. In an embodiment, the agent comprises a polypeptide, e.g., a multimeric polypeptide, comprising one or more cysteine bridges.

In an embodiment, the agent comprises a difficult to express protein. For instance, in embodiments, the polypeptide agent has an amino acid sequence that, if expressed genetically in an erythroid cell, would reach a copy number of less than 1,000, 500, 200, or 100 copies of the protein per cell. In embodiments, the polypeptide agent has an amino acid sequence that, if expressed genetically in an erythroid cell, has inefficient translation or transcription, e.g., reaching a protein or mRNA level of less than 50%, 40%, 30%, 20%, 10%, 5%, 2%, 1% of a reference value, e.g., expression of a control protein such as ADA as described in WO2015/073587. In an embodiment, the polypeptide agent comprises an isoform, e.g., a splice variant, that if expressed genetically in an erythroid cell, would not be the most abundant isoform, e.g., would be present at a level at least 10%, 20%, 30%, 40%, 50%, 60%, 70%, 80%, or 90% lower than the level of the most abundant isoform.

In an embodiment, the agent comprises an antibody molecule, e.g., a polypeptide comprising one or more of the following: a) sufficient variable region to bind cognate antigen, e.g., HC CDR1, HC CDR2, and HC CDR3, LC CDR1, LC CDR2, and LC CDR3; b) a heavy chain constant sequence comprising one or more of CH1, CH2, and CH3; c) a functional Fc region; and d) a modified or inactive Fc region, e.g., a mutationally inactivated Fc region or an Fc region having a glycosylation state that impairs Fc activity, e.g., a deglycosylated Fc region.

In an embodiment, the agent comprises an antibody, e.g., an IgA, IgG, IgG1, IgG2, IgM, IgE, or IgD.

In an embodiment, the agent comprises an anti-PDL1 antibody, an anti 4-1BB antibody, anti-α4β7 antibody, or protein A/G.

In some embodiments, the agent is deglycosylated. For instance, a glycosylated precursor may be treated with a deglycosylating enzyme (e.g., EndoS) to produce an agent.

In some embodiments, the agent comprises a polypeptide selected from or derived from one or more of the following classes, including but not limited to: an enzyme, a protease, a nuclease, a glycosidase, a lipase, a DNase, an antigen, an antibody-like molecule (e.g., a nanobody, an scFv, a duobody, or a multispecific antibody), a ligand of an antibody, a growth factor, a transporter, a cytokine, a chemokine, a growth factor receptor, a cytokine receptor, a chemokine receptor, an enzymatic recognition sequence, a transpeptidase recognition sequence, a protease recognition sequence, a cleavable domain, an intein, a DNA binding protein, an RNA binding protein, a complement regulatory molecule, a complement cascade molecule, a clotting cascade molecule, a chelator, a complement regulatory domain, an SCR domain, a CCP domain, an immunoglobulin or immunoglobulin-like domain, an armadillo repeat, a leucine zipper, a death effector domain, a cadherin repeat, an EF hand, a phosphotyrosine binding domain, a pleckstrin homology domain, an SCR homology 2 domain, a zinc finger domain, a cyclic peptide, a cell-penetrating peptide, a chaperone molecule, an integrin, a collagen, a carrier protein (e.g., albumin), a toxin binding peptide (e.g., a peptide that binds to a toxin from a bacterium, a parasite, a fungus or the environment), a myelination molecule, a prion protein binding molecule, a cluster of differentiation (CD) molecule, an immunomodulatory molecule (e.g., a co-stimulatory molecule, an activator of a co-stimulatory molecule, an inhibitor of a co-stimulatory molecule, a co-inhibitory molecule, an inhibitor of a co-inhibitory molecule or an activator of a co-inhibitory molecule), a cancer antigen or cancer cell marker, an antigen-presenting molecule, a pro-apoptotic molecule, a targeting moiety, an Fc receptor binding molecule, a tumor starvation enzyme, a DNA damage inhibitor, a cell-cycle inhibitor, a flexible linker, or an epitope tag. Specific examples of agents, e.g., polypeptides, are found, e.g., in WO2015/073587, WO2015/153102, and WO2016/183482, each of which is incorporated by reference in its entirety.

In some embodiments, the agent comprises one or more non-canonical amino acids. Non-canonical amino acids include, e.g., p-methoxyphenylalanine (pMpa); p-acetylphenylalanine (pApa); p-benzoylphenylalanine (pBpa); p-iodophenylalanine (pIpa); p-azidophenylalanine (pAzpa); p-propargyloxyphenylalanine (pPpa); α-aminocaprylic acid; o-nitrobenzylcysteine (o-NBC); 1,5-dansylalanine; and o-nitrobenzylserine (o-NBS), and other described in, e.g., U.S. Pat. No. 9,624,485, which is herein incorporated by reference in its entirety.

In some embodiments, the agent is other than a polypeptide. For instance, the agent can be a carbohydrate, small molecule, lipid, nucleic acid, therapeutic agent, naturally occurring or synthetic compound, or combinations thereof.

An exemplary exogenous polypeptide, e.g., a polypeptide agent of Table 1 or a variant thereof, includes:

a) a naturally occurring form of the polypeptide;

b) the polypeptide having a sequence appearing in a database, e.g., GenBank database, on Aug. 7, 2017;

c) a polypeptide having a sequence that differs by no more than 1, 2, 3, 4, 5 or 10 amino acid residues from a sequence of a) or b);

d) a polypeptide having a sequence that differs at no more than 1, 2, 3, 4, 5 or 10% its amino acids residues from a sequence of a) or b);

e) a polypeptide having a sequence that does not differ substantially from a sequence of a) or b); or f) a polypeptide having a sequence of c), d), or e) that does not differ substantially in a biological activity, e.g., an enzymatic activity (e.g., specificity or turnover) or binding activity (e.g., binding specificity or affinity) from a protein having the sequence of a) or b).

In embodiments, the polypeptide comprises a polypeptide or fragment thereof, e.g., all or a fragment of a polypeptide of a), b), c), d), e), or f) of the preceding paragraph.

In embodiments, the agent comprises a polypeptide of Table 1, or an amino acid sequence having at least 70%, 75%, 80%, 85%, 90%, 95%, 96%, 97%, 98%, 99%, or 99.5% identity thereto, or a functional fragment thereof.

TABLE 1

Amino acid sequences of exemplary agents

| Agent | Sequence |
|---|---|
| 4-1BBL | ACPWAVSGARASPGSAASPRLREGPELSPDDPAGLLDLRQGMFAQLVAQN VLLIDGPLSWYSDPGLAGVSLTGGLSYKEDTKELVVAKAGVYYVFFQLEL RRVVAGEGSGSVSLALHLQPLRSAAGAAALALTVDLPPASSEARNSAFGFQ GRLLHLSAGQRLGVHLHTEARARHAWQLTQGATVLGLFRVTPEIPAGLPSP RSE (SEQ ID NO: 3) |
| Anti-CD20 | Rituximab heavy chain chimeric: QVQLQQPGAELVKPGASVKMSCKASGYTFTSYNMHWVKQTPGRGLEWIG AIYPGNGDTSYNQKFKGKATLTADKSSSTAYMQLSSLTSEDSAVYYCARST YYGGDWYFNVWGAGTTVTVSAASTKGPSVFPLAPSSKSTSGGTAALGCLV KDYFPEPVTVSWNSGALTSGVHTFPAVLQSSGLYSLSSVVTVPSSSLGTQTY ICNVNHKPSNTKVDKKAEPKSCDKTHTCPPCPAPELLGGPSVFLFPPKPKDT LMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGK (SEQ ID NO: 4) Rituximab light chain chimeric: QIVLSQSPAILSASPGEKVTMTCRASSSVSYIHWFQQKPGSSPKPWIYATSNL ASGVPVRFSGSGSGTSYSLTISRVEAEDAATYYCQQWTSNPPTFGGGTKLEI |

TABLE 1-continued

Amino acid sequences of exemplary agents

| Agent | Sequence |
|---|---|
| | KRTVAAPSVFIFPPSDEQLKSGTASVVCLLNNFYPREAKVQWKVDNALQSG<br>NSQESVTEQDSKDSTYSLSSTLTLSKADYEKHKVYACEVTHQGLSSPVTKS<br>FNRGEC (SEQ ID NO: 5) |
| TRAIL | Soluble TRAIL variant DR4-1<br><br>MAMMEVQGGPSLGQTCVLIVIFTVLLQSLCVAVTYVYFTNELKQMQDKYS<br>KSGIACFLKEDDSYWDPNDEESMNSPCWQVKWQLRQLVRKMILRTSEETIS<br>TVQEKQQNISPLVRERGPQRVAAHITGTRRRSNTLSSPNSKNEKALGRKINS<br>WESSRSGHSFLSNLHLRNGELVIHEKGFYYIYSQTYFRFQEEIKENTKNDKQ<br>MVQYIYKYTSYPDPILLMKSARNSCWSKDAEYGLYSIYQGGIFELKENDRIF<br>VSVTNEHLIDMDHEASFFGAFLVG (SEQ ID NO: 6)<br><br>Soluble TRAIL variant DR4-2<br><br>MAMMEVQGGPSLGQTCVLIVIFTVLLQSLCVAVTYVYFTNELKQMQDKYS<br>KSGIACFLKEDDSYWDPNDEESMNSPCWQVKWQLRQLVRKMILRTSEETIS<br>TVQEKQQNISPLVRERGPQRVAAHITGTRGRSNTLSSPNSKNEKALGRKINS<br>WESSRRGHSFLSNLHLRNGELVIHEKGFYYIYSQTYFRFQEEIKENTKNDKQ<br>MVQYIYKYTSYPDPILLMKSARNSCWSKDAEYGLYSIYQGGIFELKENDRIF<br>VSVTNEHLIDMDHEASFFGAFLVG (SEQ ID NO: 7)<br><br>Soluble TRAIL variant DR4-3<br><br>MAMMEVQGGPSLGQTCVLIVIFTVLLQSLCVAVTYVYFTNELKQMQDKYS<br>KSGIACFLKEDDSYWDPNDEESMNSPCWQVKWQLRQLVRKMILRTSEETIS<br>TVQEKQQNISPLVRERGPQRVAAHITGTRRRSNTLSSPNSKNEKALGIKINS<br>WESSRRGHSFLSNLHLRNGELVIHEKGFYYIYSQTYFRFQEEIKENTKNDKQ<br>MVQYIYKYTDYPDPILLMKSARNSCWSKDAEYGLYSIYQGGIFELKENDRI<br>FVSVTNEHLIDMDHEASFFGAFLVG (SEQ ID NO: 8)<br><br>Soluble TRAIL variant DR5-1<br><br>MAMMEVQGGPSLGQTCVLIVIFTVLLQSLCVAVTYVYFTNELKQMQDKYS<br>KSGIACFLKEDDSYWDPNDEESMNSPCWQVKWQLRQLVRKMILRTSEETIS<br>TVQEKQQNISPLVRERGPQRVAAHITGTRGRSNTLSSPNSKNEKALGRKINS<br>WESSRSGHSFLSNLHLRNGELVIHEKGFYYIYSQTYFRFQEEIKENTKNDKQ<br>MVQYIYKYTSYPDPILLMKSARNSCWSKDAEYGLYSIYQGGIFELKENDRIF<br>VSVTNEHLIDMHHEASFFGAFLVG (SEQ ID NO: 9)<br><br>Soluble TRAIL variant DR5-2<br><br>MAMMEVQGGPSLGQTCVLIVIFTVLLQSLCVAVTYVYFTNELKQMQDKYS<br>KSGIACFLKEDDSYWDPNDEESMNSPCWQVKWQLRQLVRKMILRTSEETIS<br>TVQEKQQNISPLVRERGPQRVAAHITGTRGRSNTLSSPNSKNEKALGRKINS<br>WESSRSGHSFLSNLHLRNGELVIHEKGFYIYSQTYFRFQERIKENTKNDKQ<br>MVQYIYKYTSYPDPILLMKSARNSCWSKDAEYGLYSIYQGGIFELKENDRIF<br>VSVTNEHLIDMHHEASFFGAFLVG (SEQ ID NO: 10) |
| Anti-PD-<br>L1 scFv | VQLVESGGGLVQPGGSLRLSCAASGFTFSDSWIHWVRQAPGKGLEWVAWI<br>SPYGGSTYYADSVKGRFTISADTSKNTAYLQMNSLRAEDTAVYYCARRHW<br>PGGFDYWGQGTLVTVSSGGGGSGGGGSGGGGSIQMTQSPSSLSASVGDRV<br>TITCRASQDVSTAVAWYQQKPGKAPKLLIYSASFLYSGVPSRFSGSGSGTDF<br>TLTISSLQPEDFATYYCQQYLYHPATFGQGTKVEIK (SEQ ID NO: 11) |
| PAL | MKTLSQAQSKTSSQQFSFTGNSSANVIIGNQKLTINDVARVARNGTLVSLTN<br>NTDILQGIQASCDYINNAVESGEPIYGVTSGFGGMANVAISREQASELQTNL<br>VWFLKTGAGNKLPLADVRAAMLLRANSHMRGASGIRLELIKRMEIFLNAG<br>VTPYVYEFGSIGASGDLVPLSYITGSLIGLDPSFKVDFNGKEMDAPTALRQL<br>NLSPLTLLPKEGLAMMNGTSVMTGIAANCVYDTQILTAIAMGVHALDIQAL<br>NGTNQSFHPFIHNSKPHPGQLWAADQMISLLANSQLVRDELDGKHDYRDH<br>ELIQDRYSLRCLPQYLGPIVDGISQIAKQIEIEINSVTDNPLIDVDNQASYHGG<br>NFLGQYVGMGMDHLRYYIGLLAKHLDVQIALLASPEFSNGLPPSLLGNRER<br>KVNMGLKGLQICGNSIMPLLTFYGNSIADRFPTHAEQFNQNINSQGYTSATL<br>ARRSVDIFQNYVAIALMFGVQAVDLRTYKKTGHYDARACLSPATERLYSA<br>VRHVVGQKPTSDRPYIWNDNEQGLDEHIARISADIAAGGVIVQAVQDILPC<br>LH (SEQ ID NO: 12) |
| Y vb<br>Aspara-<br>ginase | MADKLPNIVILATGGTIAGSAATGTQTTGYKAGALGVDTLINAVPEVKKLA<br>NVKGEQFSNMASENMTGDVVLKLSQRVNELLARDDVDGVVITHGTDTVE<br>ESAYFLHLTVKSDKPVVFVAAMRPATAISADGPMNLLEAVRVAGDKQSRG<br>RGVMVVLNDRIGSARYITKTNASTLDTFKANEEGYLGVIIGNRIYYQNRIDK<br>LHTTRSVFDVRGLTSLPKVDILYGYQDDPEYLYDAAIQHGVKGIVYAGMG<br>AGSVSVRGIAGMRKAMEKGVVVIRSTRTGNGIVPPDEELPGLVSDSLNPAH<br>ARILLMLALTRTSDPKVIQEYFHTY (SEQ ID NO: 13) |

TABLE 1-continued

Amino acid sequences of exemplary agents

| Agent | Sequence |
|---|---|
| AnTi-a4b7 | Heavy chain variable region:<br><br>QVQLVQSGAEVKKPGASVKVSCKGSGYTFTSYWMHWVRQAPGQRLEWIG<br>EIDPSESNTNYNQKFKGRVTLTVDISASTAYMELSSLRSEDTAVYYCARGG<br>YDGWDYAIDYWGQGTLVTVSS (SEQ ID NO: 14)<br><br>Light chain variable region:<br><br>DVVMTQSPLSLPVTPGEPASISCRSSQSLAKSYGNTYLSWYLQKPGQSPQLL<br>IYGISNRFSGVPDRFSGSGSGTDFTLKISRVEAEDVGVYYCLQGTHQPYTFG<br>QGTKVEIK (SEQ ID NO: 15) |
| Human IL10 | SPGQGTQSENSCTHFPGNLPNMLRDLRDAFSRVKTFFQMKDQLDNLLLKES<br>LLEDFKGYLGCQALSEMIQFYLEEVMPQAENQDPDIKAHVNSLGENLKTLR<br>LRLRRCHRFLPCENKSKAVEQVKNAFNKLQEKGIYKAMSEFDIFINYIEAY<br>MTMKIRN (SEQ ID NO: 16) |
| Clotting Factor X | ANSFLEEMKKGHLERECMEETCSYEEAREVFEDSDKTNEFWNKYKDGDQ<br>CETSPCQNQGKCKDGLGEYTCTCLEGFEGKNCELFTRKLCSLDNGDCDQF<br>CHEEQNSVVCSCARGYTLADNGKACIPTGPYPCGKQTLERRKRSVAQATSS<br>SGEAPDSITWKPYDAADLDPTENPFDLLDFNQTQPERGDNNLTRIVGGQEC<br>KDGECPWQALLINEENEGFCGGTILSEFYILTAAHCLYQAKRFKVRVGDRN<br>TEQEEGGEAVHEVEVVIKHNRFTKETYDFDIAVLRLKTPITFRMNVAPACLP<br>ERDWAESTLMTQKTGIVSGFGRTHEKGRQSTRLKMLEVPYVDRNSCKLSS<br>SFIITQNMFCAGYDTKQEDACQGDSGGPHVTRFKDTYFVTGIVSWGEGCAR<br>KGKYGIYTKVTAFLKWIDRSMKTRGLPKAKSHAPEVITSSPLK<br>(SEQ ID NO: 17) |

In some embodiments, an exogenous polypeptide described herein is at least 200, 300, 400, 500, 600, 700, or 800 amino acids in length. In some embodiments, the exogenous polypeptide is between 200-300, 300-400, 400-500, 500-600, 600-700, or 700-800 amino acids in length.

In some embodiments, an erythroid cell, e.g., an enucleated erythroid cell, comprises at least 1,000, 5,000, 10,000, 15,000, 20,000, 25,000, 30,000, 50,000, 100,000, 200,000, or 500,000 copies of an exogenous polypeptide described herein, e.g., of Table 1.

In embodiments, the agent comprises one or more post-translational modifications. Post-translation modifications include cleavage (e.g., proteolytic cleavage), cyclization, glycosylation, phosphorylation, conjugation to a hydrophobic group (e.g., myristoylation, palmitoylation, isoprenylation, prenylation, or glypiation), conjugation to a cofactor (e.g., lipoylation, flavin moiety (e.g., FMN or FAD), heme C attachment, phosphopantetheinylation, or retinylidene Schiff base formation), diphthamide formation, ethanolamine phosphoglycerol attachment, hypusine formation, acylation (e.g. O-acylation, N-acylation, or S-acylation), formylation, acetylation, alkylation (e.g., methylation or ethylation), amidation, butyrylation, gamma-carboxylation, malonylation, hydroxylation, iodination, nucleotide addition such as ADP-ribosylation, oxidation, phosphate ester (O-linked) or phosphoramidate (N-linked) formation, (e.g., phosphorylation or adenylylation), propionylation, pyroglutamate formation, S-glutathionylation, S-nitrosylation, succinylation, sulfation, ISGylation, SUMOylation, ubiquitination, Neddylation, or a chemical modification of an amino acid (e.g., citrullination, deamidation, eliminylation, or carbamylation), formation of a disulfide bridge, racemization (e.g., of proline, serine, alanine, or methionine), or any combination thereof. In embodiments, glycosylation includes the addition of a glycosyl group to arginine, asparagine, cysteine, hydroxylysine, serine, threonine, tyrosine, or tryptophan, resulting in a glycoprotein. In embodiments, the glycosylation comprises, e.g., O-linked glycosylation or N-linked glycosylation.

In embodiments, the cell comprises a plurality of agents, e.g., at least 10, 20, 50, 100, 200, 500, or 1,000 different agents. In some embodiments, the plurality of agents comprise a plurality of vaccine antigens. In some embodiments, the plurality of agents have sequence similarity to each other but vary between each other at at least 1, 2, 5, 10, 20, 50, or 100 amino acid positions. In some embodiments, each agent in the plurality has at least 70%, 80%, 85%, 90%, 95%, 96%, 97%, 98%, or 99% identity to each other agent in the plurality. In some embodiments, each agent in the plurality has at least 70%, 80%, 85%, 90%, 95%, 96%, 97%, 98%, or 99% identity to at least 1, 2, 5, 10, 20, 50, or 100 other agents in the plurality.

Geometry of Coupling Reagents on Agents

A coupling agent can be attached a variety of different positions on an agent. A coupling agent can comprise a substrate reactive moiety suitable, e.g., for binding (e.g., covalently) to a substrate such as an agent (e.g., polypeptide). A coupling agent can further comprise a coupling moiety, e.g., a click coupling moiety suitable, e.g., for binding (e.g., covalently) to a second coupling agent. A suitable substrate reactive moiety can be chosen to direct the attachment of the coupling agent with the agent (e.g., polypeptide).

For instance, in some embodiments, the substrate reaction moiety is capable of reacting with an NH$_2$ group, e.g., on a side chain of lysine or the N terminus of the agent. An example of a substrate reaction moiety capable of reacting with an NH$_2$ group is an NHS ester, Imidoester, Pentafluorophenyl ester, or Hydroxymethyl phosphine. In some embodiments, the substrate reaction moiety is capable of reacting with a carboxyl of the agent, e.g., on a side chain of aspartic acid or glutamic acid or the C-terminus of the agent. An example of a substrate reaction moiety capable of reacting with a carboxyl is a carbodiimide. In some embodiments, the substrate reaction moiety is capable of reacting with a sulfhydryl of the agent, e.g., on a side chain of cysteine. An example of a substrate reaction moiety capable of reacting with a sulfhydryl is Maleimide, Haloacetyl (e.g., Bromo- or Iodo-), Pyridyldisulfide, Thiosulfonate, or Vinylsulfone. An agent having a disulfide bridge may be placed under reducing conditions to convert the disulfide bridge to sulfhydryls. In some embodiments, the substrate reaction moiety is capable of reacting with a carbonyl of the agent. For instance, a ketone or aldehyde group can be created in glycoproteins, e.g., by oxidizing the polysaccharide post-translational modifications, for instance with sodium meta-periodate. An example of a substrate reaction moiety capable of reacting with a carbonyl is a hydrazide or alkoxyamine.

A moiety on an agent can be linked to a preselected moiety on a cell. For instance, in some embodiments, an $NH_2$ group on the agent is linked to an $NH_2$ group, carboxyl, sulfhydryl, or carbonyl of the cell. In embodiments, a carboxyl group on the agent is linked to an $NH_2$ group, carboxyl, sulfhydryl, or carbonyl of the cell. In embodiments, a sulfhydryl group on the agent is linked to an $NH_2$ group, carboxyl, sulfhydryl, or carbonyl of the cell. In embodiments, a carbonyl group on the agent is linked to an $NH_2$ group, carboxyl, sulfhydryl, or carbonyl of the cell.

Clickable Format Agents

In some embodiments, the agent is a polypeptide with a coupling agent linked to a predetermined amino acid. Briefly, the polypeptide agent can be produced in a first cell (a "factory cell", such that a non-canonical amino acid (ncAA) comprising a first coupling reagent is present at one or more amino acid positions of the polypeptide agent. The agent can then be coupled to a second cell that has a second coupling reagent at the cell surface, thereby coupling the polypeptide agent to the second cell. This technology can use site-specific incorporation of the ncAA, such that the orientation of the agent on the cell surface is controlled.

For instance, ncAAs can be introduced into the polypeptide agent by genetically incorporating an Amber stop codon (TAG) at the site of interest in a nucleic acid encoding the polypeptide agent, e.g., as described in Nikic et al. Nature Protocols 2015 which is herein incorporated by reference in its entirety. The amber stop codon can be incorporated, e.g., at the N-terminus, C-terminus, or interior of the protein. This plasmid encoding the polypeptide agent can be co-transfected into a factory cell (e.g., HEK293 or CHO cell) with another plasmid encoding an aminoacyl-tRNA synthase/tRNA pair that is orthogonal to the host's translational machinery. In the presence of ncAA, there is read through of the Amber codon and incorporation of the ncAA. For instance, one may use *M. mazei* pyrrolysine aminoacyl-tRNA synthetase/tRNA (PylRS/tRNAPyl) with Y306A and Y384F mutations and the ncAAs: cyclooctyne-lysine (SCO), Endo Bicyclo [6.1.0] nonyne-lysine (endoBCN), Exo Bicyclo [6.1.0] nonyne-lysine (exoBCN), or Rac Bicyclo [6.1.0] nonyne-lysine (racBCN). Other suitable ncAAs are described in the section herein entitled "Clickable format cells". The plasmid may further encode a sequence that directs secretion of the protein. Transient transfection or a stable cell line can be used.

Once the clickable format protein is produced, it can be reacted with a cell having a second coupling agent. For instance, the cell can by an erythroid cell having a click linker, e.g., a click linker comprising an azide.

Geometry of Coupling Reagents on Cells

A coupling agent can be attached a variety of different positions on a cell. A coupling agent can comprise a substrate reactive moiety suitable, e.g., for binding (e.g., covalently) to a substrate such as a cell (e.g., a polypeptide or carbohydrate moiety on the cell). A coupling agent can further comprise a coupling moiety, e.g., a click coupling moiety suitable, e.g., for binding (e.g., covalently) to a second coupling agent. A suitable substrate reactive moiety can be chosen to direct the attachment of the coupling agent with the cell.

Suitable substrate reaction moieties are described herein, e.g., in the section entitled "Geometry of coupling reagents on agents."

A moiety on a cell can be linked to a preselected moiety on an agent. For instance, in some embodiments, an $NH_2$ group on the cell is linked to an $NH_2$ group, carboxyl, sulfhydryl, or carbonyl of the agent. In embodiments, a carboxyl group on the cell is linked to an $NH_2$ group, carboxyl, sulfhydryl, or carbonyl of the agent. In embodiments, a sulfhydryl group on the cell is linked to an $NH_2$ group, carboxyl, sulfhydryl, or carbonyl of the agent. In embodiments, a carbonyl group on the cell is linked to an $NH_2$ group, carboxyl, sulfhydryl, or carbonyl of the agent.

Sortase and Click

In some embodiments, a transpeptidase reaction such as a sortase reaction is used to attach a linker to an agent or to a cell.

For instance, in some embodiments a polypeptide agent comprises a transpeptidase recognition sequence, e.g., a sortase recognition sequence. The polypeptide agent may be contacted with a sortase and a coupling reagent that has a compatible sortase recognition sequence, thereby sortagging the coupling reagent onto the polypeptide agent. The polypeptide agent can then be reacted with a cell having a second coupling agent. The second coupling agent may be, e.g., on an $NH_2$ group, carboxyl, sulfhydryl, or carbonyl of the cell.

In some embodiments a cell (e.g., a polypeptide or carbohydrate on the cell) comprises a transpeptidase recognition sequence, e.g., a sortase recognition sequence. For instance, the cell may genetically express a transmembrane protein comprising a sortase recognition sequence at the cell surface. The cell may be contacted with a sortase and a coupling reagent that has a compatible sortase recognition sequence, thereby sortagging the coupling reagent onto the cell. The cell can then be reacted with a polypeptide agent having a second coupling agent. The second coupling agent may be, e.g., on an $NH_2$ group, carboxyl, sulfhydryl, or carbonyl of the polypeptide agent.

In some embodiments, the polypeptide agent does not comprise a transpeptidase recognition sequence, e.g., a sortase recognition sequence. In embodiments, the cell does not comprise an exogenous transpeptidase recognition sequence, e.g., a sortase recognition sequence. In embodiments, the method does not comprise a sortagging step. In embodiments, the functionalized erythroid cell does not comprise a sortase transfer signature.

A sortase can enzymatically conjugate two sortase recognition motifs together. The first sortase recognition motif can be a sortase donor motif and the second sortase recognition motif can be a sortase acceptor motif.

Sortase recognition motifs include LPXTA (SEQ ID NO: 18) and LPXTG (SEQ ID NO: 1), in which X is any amino acid residue. One exemplary sortase recognition motif is LPXTG (SEQ ID NO: 1), in which X can be any amino acid residue (naturally-occurring or non-canonical), e.g., any of the 20 standard amino acids found most commonly in proteins found in living organisms. In some examples, the recognition motif is LPXTG (SEQ ID NO: 19) or LPXT, in which X is D, E, A, N, Q, K, or R. In other examples, X is selected from K, E, N, Q, or A in an LPXTG (SEQ ID NO:

20) or LPXT motif, which are recognizable by a sortase A. In yet other examples, X is selected from K, S, E, L, A, or N in an LPXTG (SEQ ID NO: 21) or LPXT motif, which are recognizable by a class C sortase. Exemplary sortase recognition motifs include, but are not limited to, LPKTG (SEQ ID NO: 22), LPITG (SEQ ID NO: 23), LPDTA (SEQ ID NO: 24), SPKTG (SEQ ID NO: 25), LAETG (SEQ ID NO: 26), LAATG (SEQ ID NO: 27), LAHTG (SEQ ID NO: 28), LASTG (SEQ ID NO: 29), LPLTG (SEQ ID NO: 30), LSRTG (SEQ ID NO: 31), LPETG (SEQ ID NO: 32), VPDTG (SEQ ID NO: 33), IPQTG (SEQ ID NO: 34), YPRRG (SEQ ID NO: 35), LPMTG (SEQ ID NO: 36), LAFTG (SEQ ID NO: 37), LPQTS (SEQ ID NO: 38), LPXT, LAXT, LPXA, LGXT, IPXT, NPXT, NPQS (SEQ ID NO: 39), LPST (SEQ ID NO: 40), NSKT (SEQ ID NO: 41), NPQT (SEQ ID NO: 42), NAKT (SEQ ID NO: 43), LPIT (SEQ ID NO: 44), LAET (SEQ ID NO: 45), LPXAG (SEQ ID NO: 46), LPNAG (SEQ ID NO: 47), LPXTA (SEQ ID NO: 18), LPNTA (SEQ ID NO: 48), LGXTG (SEQ ID NO: 49), LGATG (SEQ ID NO: 50), IPXTG (SEQ ID NO: 51), IPNTG (SEQ ID NO: 52), IPETG (SEQ ID NO: 53), NPXTX, NP[Q/K]-[T/s]-[N/G/s], NPQTN (SEQ ID NO: 54), NPKTG (SEQ ID NO: 55), NSKTA (SEQ ID NO: 56), NPQTG (SEQ ID NO: 57), NAKTN (SEQ ID NO: 58), NPQSS (SEQ ID NO: 59), NA-[E/A/S/H]-TG (SEQ ID NO: 60), LAXTG (SEQ ID NO: 61), QVPTGV (SEQ ID NO: 62), LPXTX, LP[Q/K]T[A/S]T (SEQ ID NO: 63), or LPXT [A/S].

Sortase acceptor motifs include oligoglycines or oligoalanines, such as a 1-5 glycine fragment or a 1-5 alanine fragment. In some examples, the oligoglycine consists of 3 or 5 glycine residues. In other examples, the oligoalanine consists of 3 or 5 alanine residues.

A sortase transfer signature can be created by a sortase reaction. For instance, a sortase-mediated reaction of LPXTGG (SEQ ID NO: 2) with $(G)_n$ can produce a sortase transfer signature of LPXT$(G)_n$ (SEQ ID NO: 1). In embodiments, the sortase transfer signature comprises a sequence of a sortase recognition motif described herein, e.g., in this section. In embodiments, the sortase transfer signature further comprises one or more alanine or glycine amino acids, e.g., at the C-terminus of the sequence of the sortase recognition motif.

A variety of sortases are described, e.g., in WO2014/183071 (e.g., on pages 33-37 therein), which application is herein incorporated by reference in its entirety.

Second Agents Added by Various Methods

In some embodiments, a cell (e.g., enucleated erythroid cell) described herein comprises (in addition to its first agent) a second agent, e.g, an exogenous polypeptide agent. In some embodiments, the second agent is conjugated to the cell, e.g., using click chemistry. In some embodiments, the second agent comprises a protein expressed from an exogenous nucleic acid (e.g., DNA or RNA) introduced into the cell or a precursor thereof. In some embodiments, the second agent comprises a protein sortagged onto the cell. In some embodiments, the second agent is hypotonically loaded into the cell. In some embodiments, the second agent is not covalently linked to a click signature or a residual linker.

Non-Conjugation Methods of Adding an Agent to a Cell

While in many embodiments an agent is conjugated to a cell, e.g., using click chemistry, it is understood that any agent described herein may also be added to a cell using a variety of methods. Accordingly, in some aspects, the present disclosure provides a cell (e.g., an erythroid cell, e.g., an enucleated erythroid cell) comprising an agent, e.g., exogenous polypeptide agent, described herein, e.g., a polypeptide of Table 1, or a fragment or variant thereof. The cell can be made, e.g., by introducing a nucleic acid encoding the protein into the cell or a precursor thereof, by sortagging, by hypotonic loading, or by chemical conjugation.

Methods of Treatment with Compositions Herein, e.g., Erythroid Cells

Methods of administering engineered erythroid cells are described, e.g., in WO2015/153102 and WO2015/073587, each of which is incorporated by reference in its entirety.

In embodiments, the erythroid cells described herein are administered to a subject, e.g., a mammal, e.g., a human. Exemplary mammals that can be treated include without limitation, humans, domestic animals (e.g., dogs, cats and the like), farm animals (e.g., cows, sheep, pigs, horses and the like) and laboratory animals (e.g., monkey, rats, mice, rabbits, guinea pigs and the like). The methods described herein are applicable to both human therapy and veterinary applications.

In some embodiments, the erythroid cells described herein are administered to a subject for the treatment or prevention of inflammation and diseases associated with inflammation, including sepsis, autoimmune disease, cancer, and microbial infections. In some embodiments, the erythroid cells described herein are administered to a subject with an autoimmune disease, e.g., multiple sclerosis, type 1 diabetes, rheumatoid arthritis, membranous nephritis, or any of the diseases listed in Table F of WO2015/153102, which is incorporated by reference herein in its entirety.

In some aspects, the present disclosure provides a method of treating a disease or condition described herein, comprising administering to a subject in need thereof a composition described herein, e.g., an erythroid cell described herein. In some embodiments, the disease or condition is a cancer, e.g., a cancer described herein. In some aspects, the disclosure provides a use of an erythroid cell described herein for treating a disease or condition described herein, e.g., a cancer. In some aspects, the disclosure provides a use of an erythroid cell described herein for manufacture of a medicament for treating a disease or condition described herein, e.g., a cancer. Exemplary cancers are described in WO2015/073587, which is incorporated by reference herein in its entirety.

In some embodiments, the erythroid cells are administered intravenously, e.g., by intravenous infusion.

All references cited herein are incorporated herein by reference in their entirety.

EXAMPLES

In order that the invention described herein may be more fully understood, the following examples are set forth. The examples described in this application are offered to illustrate the compositions, preparations, and methods provided herein and are not to be construed in any way as limiting their scope.

Example 1: Preparation of an Erythroid Cell Comprising a Click Handle

A population of erythroid cells was prepared for labeling with a coupling reagent. Erythrocytes obtained from whole blood were filtered and concentrated to a density of $3.31 \times 10^9$ cells/mL. The cells were washed twice with ice-cold phosphate-buffered saline (PBS, 2×1 mL) and the residual volume was removed by pipette. PBS at pH 8 (100 uL) was then added to the cells.

Stock solutions of the following coupling reagents were prepared at 1 mM (DBCO-sulfo-NHS ester, DBCO-PEG5-NHS ester, 3-azidopropionic acid sulfo-NHS ester, and azido-PEG4-NHS ester), and each solution was added to a sample of cells for a final coupling reagent concentration of either 0.1 mM or 0.04 mM. The reaction was incubated at room temperature for 30 minutes, with gentle agitation every 10 minutes.

The labeling reaction was quenched by adding 1 mL PBSA (PBS with 0.1% BSA) to each reaction, and allowing each reaction to incubate for 5 minutes at room temperature. The cells were pelleted by centrifugation (5 minutes at 2500 rpm), and the supernatant was removed by aspiration. The cell pellet was then washed with PBS (1 mL) and pelleted again (5 minutes at 2500 rpm), and the supernatant was removed by aspiration.

In order to detect the level of labeling, a detection reagent stock solution comprising either Cy5-biotin-azide or Cy5-DBCO was prepared at 100 nM. The detection reagent (100 uL) was added to each reaction, and the reactions were incubated at room temperature for 30 minutes. The labeling efficiency was determined by flow cytometry, and is summarized below in Table 2.

Proteins were typically desalted, buffer exchanged to PBS, and concentrated to ≥1 mg/mL prior to labeling, and the pH was adjusted to pH 7-8. Antibodies were routinely deglycosylated with an endoglycosidase (e.g., EndoS) to prevent ADCC; the endoglycosidase was removed using an affinity purification prior to addition of the coupling reagent.

Stock solutions of coupling reagents were prepared as described in Example 1. For protein solutions with a concentration greater than 5 mg/mL, the coupling reagent was added at a 10-fold molar excess relative to the protein concentration. For protein solutions with a concentration less than 5 mg/mL, the coupling reagent was added at a 20-fold to 50-fold molar excess relative to the protein concentration. The protein labeling reaction was incubated at room temperature for 30 minutes, with gentle agitation every 10 minutes.

In order to detect the level of labeling, a detection reagent stock solution comprising either Cy5-biotin-azide or WS-

TABLE 2

Conjugation efficiency of click reactions

| Sample # | Click chemistry reagent | Detection reagent | Conjugation Efficiency (%) |
|---|---|---|---|
| 1 | DBCO-Sulfo-NHS ester 0.1 mM | Cy5 biotin Azide | 88.5 |
| 2 | DBCO-Sulfo-NHS ester 0.04 mM | Cy5 biotin Azide | 38.3 |
| 3 | Sulfo-DBCO-NHS ester 0.1 mM | Cy5 Azide | 74.4 |
| 4 | Sulfo-DBCO NHS ester 0.04 mM | Cy5 Azide | 55.1 |
| 5 | DBCO-PEG4-NHS ester 0.1 mM | Cy5 Azide | 97.4 |
| 6 | DBCO-PEG4-NHS ester 0.04 mM | Cy5 Azide | 96.1 |
| 7 | DBCO-PEG5-NHS ester 0.1 mM | Cy5 biotin Azide | 83.1 |
| 8 | DBCO-PEG5-NHS ester 0.04 mM | Cy5 biotin Azide | 29.7 |
| 9 | DBCO-PEG13-NHS ester 0.1 mM | Cy5 Azide | 98.0 |
| 10 | DBCO-PEG13-NHS ester 0.04 mM | Cy5 Azide | 95.5 |
| 11 | 3-Azidopropionic Acid Sulfo-NHS ester 0.1 mM | Cy5 DBCO | 99.8 |
| 12 | 3-Azidopropionic Acid Sulfo-NHS ester 0.04 mM | Cy5 DBCO | 97.9 |
| 13 | 6-Azidohexanoic Acid Sulfo-NHS ester 0.1 mM | Cy5 DBCO | 98.9 |
| 14 | 6-Azidohexanoic Acid Sulfo-NHS ester 0.04 mM | Cy5 DBCO | 99.3 |
| 15 | Azido-PEG4-NHS ester 0.1 mM | Cy5 DBCO | 99.1 |
| 16 | Azido-PEG4-NHS ester 0.04 mM | Cy5 DBCO | 67.0 |
| 17 | TCO-PEG4-NHS ester 0.1 mM | Cy5 Methyltetrazine | 1.4 |
| 18 | TCO-PEG4-NHS ester 0.04 mM | Cy5 Methyltetrazine | 3.0 |
| 19 | TCO-PEG12-NHS ester 0.1 mM | Cy5 Methyltetrazine | 96.7 |
| 20 | TCO-PEG12-NHS ester 0.04 mM | Cy5 Methyltetrazine | 80.5 |
| 21 | Methyltetrazine-Sulfo-NHS ester 0.1 mM | Cy5 TCO | 97.6 |
| 22 | Methyltetrazine-Sulfo-NHS ester 0.04 mM | Cy5-TCO | 95.1 |
| 23 | Methyltetrazine-PEG4-NHS ester 0.1 mM | Cy5-TCO | 97.5 |
| 24 | Methyltetrazine-PEG4-NHS ester 0.04 mM | Cy5-TCO | 98.7 |
| 25 | Control (N/A) | Cy5 biotin Azide | 0.74 |
| 26 | Control (N/A) | Cy5 DBCO | 0.43 |

Example 2: Preparation of an Agent Comprising a Click Handle

Proteins of interest were prepared for coupling to erythroid cells by labeling with a coupling reagent. Exemplary proteins for labeling included antibodies (e.g., an anti-PDL1 (rat anti-mouse PDL1 antibody) and anti-α4β7 (a rat anti-mouse α4β7 antibody)), 4-1BB ligand, and protein A/G. DBCO-biotin was prepared and added to each reaction, and the reactions were incubated at room temperature for 30 minutes. The labeling efficiency was determined by Western blotting, using an anti-biotin antibody for detection.

In an alternative method of detection for degree of labeling, the Nanodrop UV-Vis program was used to read approximately 1-3 &L of labeled protein at absorbance 280 nm and 309 nm with a baseline correction at 750 nm.

Figures 2A, 2B, 2C:
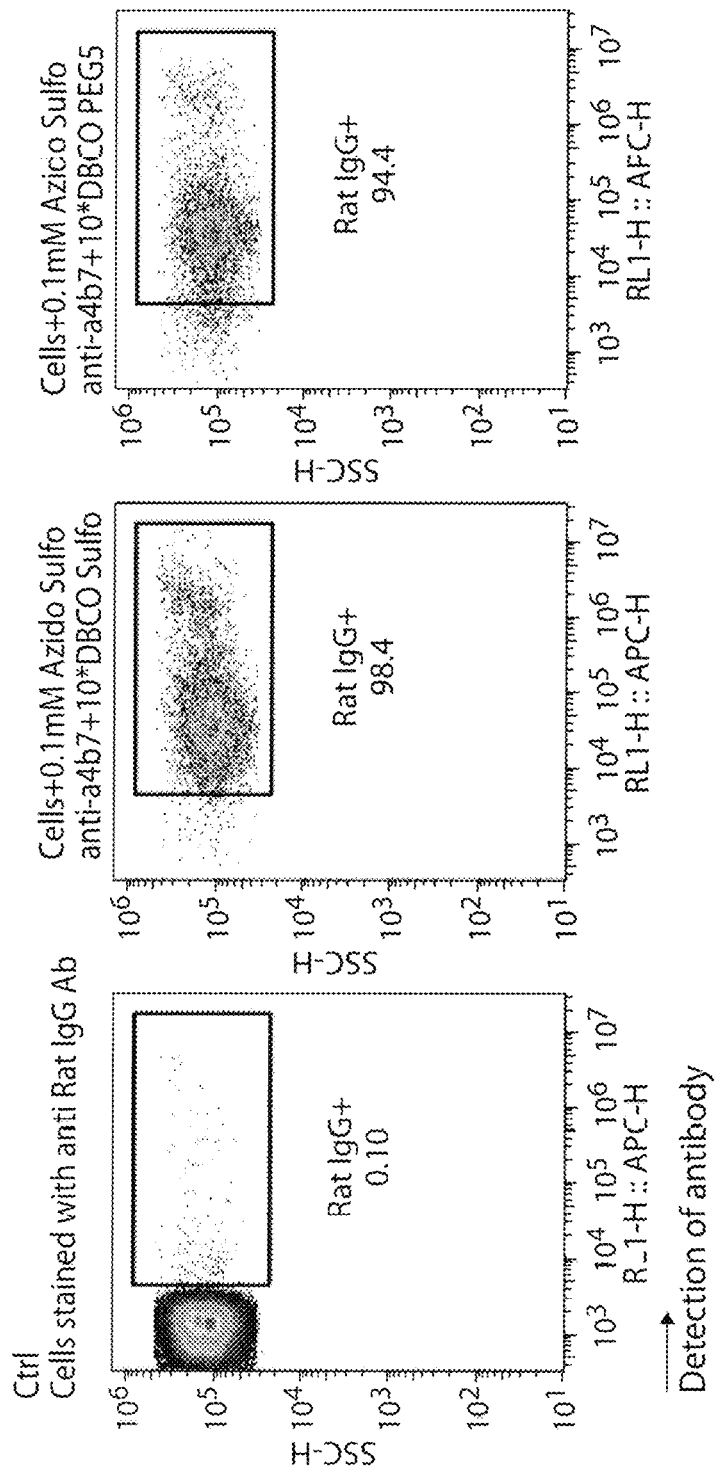
FIGS. 2A-2C are flow cytometry images of erythroid cells that have been coupled to an exemplary agent (an anti-α4β7 antibody) using the coupling reagents described herein.

Example 3: Production of Enucleated Erythroid Cells Comprising an Agent Covalently Linked to the Cell Surface by a Residual Linker Comprising a Click Signature Proteins were coupled to erythroid cells according to the general procedure described below. Erythroid cells labeled with 3-azidopropionic acid sulfo-NHS ester (Sample #1.1 in Table 2) as described in Example 1 were incubated with 1.5-3 molar equivalents of an anti-α4β7 (mouse) antibody labeled with DBCO-sulfo-NHS ester or DBCO-PEG5-NHS ester, and the reaction was incubated at room temperature for up to 12 hours at either room temperature or 4° C. The cells were then washed with PBS or PBSA, and stained with an anti-mouse antibody linked to a detection agent. The cells were then analyzed via flow cytometry to determine the protein labeling efficiency. As shown in FIGS. 2A-2C, the protein labeling efficiency was determined to be 98.4% for the DBCO-sulfo-NHS ester-linked anti-α4β7 antibody (FIG. 2B) and 94.4% for the DBCO-PEG5-NHS ester-linked anti-α4β7 antibody (FIG. 2C).

In another experiment, proteins were coupled to erythroid cells in small reaction volumes using high concentrations of protein. To perform the reaction, erythroid cells were labeled with 3-Azidopropionic acid Sulfo-NHS Ester (AS). An anti-α4β7 (rat) antibody was labeled with DBCO-sulfo-NHS ester (DS) or DBCO-PEG5-NHS ester (DP). The labeled cells were incubated with 1-20E6 molar equivalents per cell of the anti-α4β7 antibody in an undiluted in a volume of 5-10 μL, for 1 hour at 23° C. The cells were then washed with phosphate buffered saline with 0.1% bovine serum albumin, and stained with an anti-rat antibody linked to a fluorophore (fluorescein isothiocyanate). The cells were then analyzed via flow cytometry to determine the protein clicking efficiency. As shown in Table 3, the protein clicking-efficiency was determined to be in the range of 98.9-99.8%. A cell is considered positive for fluorescence if its fluorescence is greater than 99% of otherwise similar unlabeled cells. This experiment indicates that it is possible to label a very high percentage of the cells with a protein, e.g., by using a small reaction volume and high amount of protein. This experiment also indicates it is possible to link a multimer to the cell, as the antibody has two heavy chains and two light chains. This Example also indicates it is possible to link large moieties to a cell, as the antibody has a molecular weight of about 150 kDa.

TABLE 3

Efficiency of labeling cells with anti-α4β7

| Number of AS-labeled cells | Concentration of AS | Volume of click reaction | molar excess DBCO: protein | DBCO reagent | Percent cells positive for fluorescence |
|---|---|---|---|---|---|
| 1E7 | 0.1 mM | 5 ul | 10 | DS | 99.8% |
| 1E7 | 0.1 mM | 10 ul | 10 | DP | 98.9% |
| 1E7 | 0.1 mM | 10 ul | 50 | DS | 99.6% |
| 1E8 | 0.1 mM | 10 ul | 10 | DP | 99.7% |
| 1E8 | 0.1 mM | 10 ul | 50 | DS | 99.7% |

Example 4: Coupling of an Antibody Agent to Erythroid Cells Via a Residual Linker Comprising a Click Signature It is sometimes desirable to conjugate a protein having multiple subunits and/or post-translational modifications to a cell. This Example describes conjugation of an antibody to a cell surface.

An anti-PD-L1 antibody (aPD-L1) (rat IgG2b) was coupled to erythroid cells under different reaction conditions described in Table 4. To perform the reaction, erythroid cells were labeled with 0.1 mM 3-Azidopropionic Acid Sulfo-NHS ester (AS) (resuspended in DMSO) for a labeling concentration of 0.1 mM AS. aPD-L1 was labeled with 10× excess of DBCO-Sulfo-NHS ester (DS) (20 ul of 10 mM DS). The labeled cells were incubated with the concentration, volume and amount of the labeled aPD-L1 indicated in Table 4 for 1 hour at 25° C. The cells were then washed with PBS, and stained with an anti-rat kappa light chain antibody linked to a fluorophore (PE). The cells were then analyzed via flow cytometry to determine the protein labeling efficiency. As shown in Table 4, the protein labeling efficiency was determined to be in the range of 99.7-99.9%. A cell is considered positive for fluorescence if its fluorescence is greater than 99% of otherwise similar unlabeled cells. The number of aPD-L1 molecules present per cell was determined, and found to be 7000-15000 molecules of aPD-L1 per cell. The amount of protein (in ng) clicked per cell was also determined and is shown in Table 4. In general, adding higher concentrations of protein resulted in a higher percentage of cells being modified and a higher number of molecules conjugated per cell. This experiment demonstrates the production of a population of cells having a very high labeling efficiency with a protein, e.g., attaining an average number of molecules per cell in the range of 7000 to 14,000 molecules per cell. This experiment also demonstrates that a multimer can be linked to a cell, as the antibody has two heavy chains and two light chains. The experiment also indicates that large populations of cells, e.g., having 1E8 or 1E9 erythroid cells, can be labeled, with a high percentage of cells labeled and a desired amount of protein per cell achieved.

TABLE 4

Efficiency of labeling cells with aPD-L1

| Number of Cells | Volume of Protein | Concentration of Protein (mg/mL) | % Cells Clicked | Molecules/Cell | Protein (ng) |
|---|---|---|---|---|---|
| 1E7 | 10 ul | 4.5 | 99.9 | 6,955 | 2.88 |
| 1E7 | 10 ul | 2 | 99.8 | 7,014 | 2.91 |
| 1E7 | 10 ul | 0.5 | 99.7 | 6,728 | 2.78 |
| 1E8 | 50 ul | 4.5 | 99.9 | 13,892 | 57.61 |
| 1E8 | 50 ul | 2 | 99.8 | 10,934 | 45.30 |
| 1E8 | 50 ul | 0.5 | 99.7 | 9,797 | 40.55 |
| 1E9 | 100 ul | 4.5 | 99.9 | 14,916 | 618.61 |
| 1E9 | 100 ul | 2 | 99.8 | 12,126 | 502.40 |
| 1E9 | 100 ul | 0.5 | 99.7 | 7,476 | 309.43 |

Example 5: Coupling of a Protein Ligand Agent to Erythroid Cells Via a Residual Linker Comprising a Click Signature 41BB ligand (m41BBL) was coupled to erythroid cells. To perform the reaction, erythroid cells were labeled with 3-Azidopropionic acid Sulfo-NHS Ester (AS) and m41BBL was labeled with DBCO-sulfo-NHS ester (DS). The labeled cells were incubated with 1-5 mg/ml of labeled m41BBL, in a volume of 10-30 μL, for 1 hour at 23° C. The cells were then washed with phosphate buffered saline with 0.1% bovine serum albumin, and stained with fluorescent detection reagent (anti-m41BBL-PE). The cells were then analyzed via flow cytometry to determine the protein clicking efficiency. As shown in Table 5, the protein clicking efficiency was determined to be in the range of 1.14-99.9%. A cell is considered positive for fluorescence if its fluorescence is greater than 99% of otherwise similar unlabeled cells. This experiment demonstrates the production of a population of cells having a very high labeling efficiency with a protein ligand.

TABLE 5

Efficiency of labeling cells with m41BBL

| Number of cells | m41BBL concentration (mg/ml) | m41BBL molecules/cell | Percent cells positive for fluorescence |
|---|---|---|---|
| 1E7 | 1.024 | 44,158 | 88.7% |
| 1E8 | 1.024 | 40,926 | 86.5% |
| 1E8 | 5 | 94,874 | 99.9% |

Example 6: A Protein Ligand Coupled to Erythroid Cells has Binding Activity

It is often desirable to produce a cell population having a high percentage of labeled cells, and a high level of clicked protein per cell. At the same time, it is usually desirable to avoid "over-labeling", e.g., destroying a protein's functionality by conjugating linkers to too many sites on the protein. Consequently, functionalized erythroid cells having clicked proteins were tested for the ability to bind a physiological ligand.

41BB ligand (m41BBL) was coupled to erythroid cells as described in Example 5. The cells were then contacted with 41BB (the cognate binding partner of 41BBL), a Phycoerythrin-labeled antibody that binds 41BB, and an Allophycocyanin (APC)-labeled antibody that binds 41BB. Binding of the 41BB to the cells indicates that not only is 41BBL present on the cells, but that its binding site is functional and oriented to permit binding. Binding of the anti-41BBL antibody confirms that 41BBL is present on the cells. The cells were analyzed via flow cytometry to determine the protein labeling efficiency. As shown in Table 6, 41BB binding was determined to be in the range of 71.4-97.0%. A cell is considered positive for fluorescence if its fluorescence is greater than 99% of otherwise similar unlabeled cells. This experiment demonstrates the production of cells with very high labeling efficiency yet without "over-labeling", e.g., without destroying the ligand's binding site.

TABLE 6

Binding of erythroid cell-m41BBL to 41BB

| Number of cells | m41BBL degree of labeling w/ DS | Percent cells positive for fluorescence |
|---|---|---|
| 1E7 | ~2.64 | 71.4% |
| 1E8 | ~2.64 | 72.4% |
| 1E8 | ~1.74 | 97.0% |

Example 7: An Antibody Coupled to Erythroid Cells has Binding Activity

It is often desirable to produce a cell population having a high percentage of labeled cells, and a high level of clicked protein per cell, without "over-labeling." Consequently, a clicked antibody was tested for the ability to bind its antigen.

Anti-PD-L1 was coupled to erythroid cells. To perform the reaction, erythroid cells were labeled with 3-Azidopropionic acid Sulfo-NHS Ester (AS) and aPD-L1 was labeled with DBCO-sulfo-NHS ester (DS). The labeled cells were incubated with 2 mg/ml of labeled anti PD-L1, in a volume of 20 ul, for 1 hour at 20° C. The cells were then contacted with recombinant mouse PD-L1 having an Fc chimera tag. This can be detected with anti Fc antibody. Binding of the mouse erythroid cells that are clicked with aPD-L1 to the recombinant protein was demonstrated by a complete shift of the population so that all of the cells are double positive for rat antibody (indicating the presence of the antibody) as well as Fc tag (indicating binding to the recombinant protein).

Figure 3:
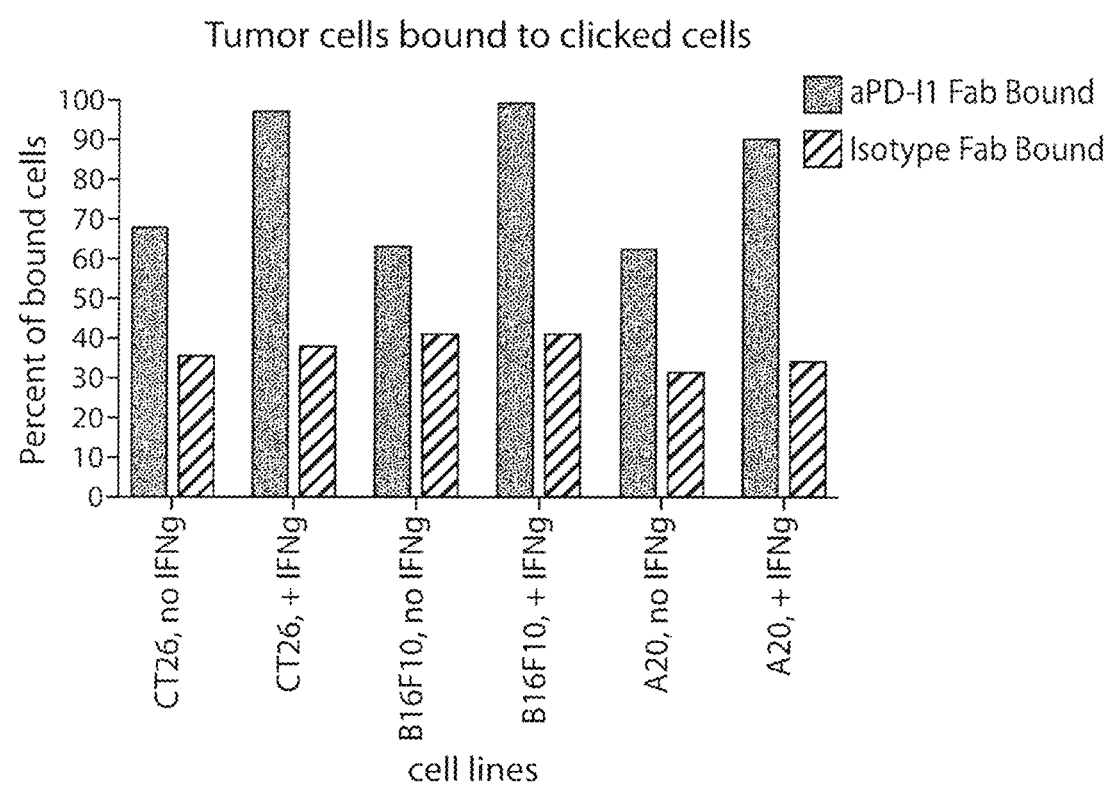
FIG. 3 is a graph showing the percentage of tumor cells bound by erythroid cells functionalized with anti-PD-L1 antibody or control cells functionalized with isotype control antibody.

Additionally, the ability of aPD-L1 labelled erythroid cells to bind to murine tumor cell lines that express PD-L1 was evaluated. Initially PD-L1 expression was evaluated in three cell lines: CT-26, B16F.10 and A20 with or without IFNg stimulation for 24 hr (which induces PD-L1 expression on the tumor cells). Expression of PD-L1 was evaluated by staining with aPD-L1 antibody in comparison with isotype control antibody. Binding of erythroid cells that are clicked with aPD-L1 to PD-L1 expressing cells was evaluated by incubating cancer cells that were prelabelled with cell trace Far red and erythroid cells at 4° C. for 2 hours. The cell suspension was stained with anti-Kappa chain antibody and assessed in flow cytometer. A population that is double positive for Far Red and kappa would indicated that the erythroid cells bound to tumor cells. This experiment evaluated conditions with or without IFNg pre-incubation and compared the aPD-L1 clicked erythroid cells to cells that are clicked with an isotype control antibody. The percentage of tumor cells that bound to aPD-L1 mouse erythroid cells ranged between 60-99% depending on the level of PD-L1 expression in the tumor cell line (FIG. 3). The percentage of tumor cells that bound to isotype control clicked mouse erythroid cells did not correlate with level of PD-L1 expression, as expected. Overall, the binding of aPD-L1 mouse erythroid cells to tumor cells was significantly enhanced with increased PD-L1 expression. Binding of erythroid cells expressing aPD-L1 to recombinant PD-L1 and to tumor cells expressing PD-L1 indicates that not only is anti-PD-L1 present on the cells, but that its binding site is functional and oriented to permit binding.

Example 8: Quantifying Unreacted Coupling Reagent on Cells and Proteins

In some embodiments, it is desirable to have no, or very low levels of, un-reacted click linker present on the cell and the protein to which it is linked. While not wishing to be bound by theory, in some embodiments, lower levels of un-reacted click linker are associated with lower immunogenicity of the functionalized cell. This example describes quantification of un-reacted click linker present on the cell and the protein.

Cells were labeled by reaction with 3-Azidopropionic acid Sulfo-NHS Ester (AS), and m41BBL protein was labeled by reaction with DBCO-sulfo-NHS ester (DS). The cells and protein were then combined to conjugate the protein to the cell surface. Residual unreacted linker was then detected by adding fluorescently labeled linker, wherein addition of Cy5 DBCO reacted with and identified residual linker on the cell, and addition of Cy5 biotin Azide reacted with and identified residual linker on the protein. The experiment indicated low levels of un-reacted linker on proteins, specifically 11.2%. This Example demonstrates the ability to detect previously unreacted linker sites on the manufactured cell and protein, e.g., as a quality control test.

It also demonstrates the ability to reduce the number of unreacted linker sites on the manufactured cell and protein by reacting them with a linker, e.g., a linker with low steric hindrance.

Example 9: Conjugating Exogenous Polypeptide Agents onto Various Cell Types

A mixture of cells was obtained from mouse spleen by mechanical disruption and lysing red blood cells. The remaining cells were labeled with 0.1 mM 3-Azidopropionic acid Sulfo-NHS Ester (AS). Purified *E. coli* asparaginase was labeled with DBCO. The labeled cells and protein were then combined to allow conjugation. Surface asparaginase was detected with a rabbit anti-asparaginase antibody and an anti-rabbit secondary antibody labeled with Alexa Fluor 657. The identity of each cell type was detected using the markers described in Table 7. The cells were analyzed by flow cytometry. The experiment indicated significant labeling of all cell types tested as indicated in Table 7, using a gating strategy designed to distinguish between different types of cells in the population.

TABLE 7

Labeling efficiency of different cell types

| Markers | Cell Type | Percent Clicked by Protein Detection |
|---|---|---|
| CD3+ CD4+ | CD4 T cells | 99.1% |
| CD3+ CD8+ | CD8 T cells | 99.2% |
| CD3− NK1.1+ | Natural Killer Cells | 99.4% |
| CD3+ NK1.1+ | Natural Killer T cells | 99.3% |
| CD11b+ | Myeloid Cells | 89.4% |
| CD11c+ | Dendritic Cells | 88.5% |
| CD19+CD61− | B cells | 95.0% |
| CD61+ CD19− CD11b− | Platelets | 96.7% |
| Ly6G++ | Neutrophils | 84.1% |

The experiment also demonstrates conjugation of an enzyme to the surface of numerous cells, including immune cells, nucleated cells, and enucleated cells.

Example 10: Erythroid Cells Conjugated to an Exogenous Polypeptide Agent Slow Tumor Growth In Vivo An MC38 mouse model system for colon cancer was used to test the effects of functionalized erythroid cells on tumor growth. Without being bound by theory, 41BBL is thought to slow tumor growth by eliciting diverse immune effector responses on both the innate and adaptive immune arms. The most potent responses stimulate CD8+ cytotoxic T cells to proliferate and increase their effector potential through increased interferon gamma production and expression of multiple granzymes. In contrast, published preclinical data using multiple 4-1BB agonists have shown little or no single agent antitumor activity in the MC38 or other models (Chen, et al, 2014; Kudo-Saito, et al, 2006; Kocak, et al, Canc Res 2006; Tirapu, et al, Int J Cancer 2004; John, et al, Canc Res 2012). These differences in activity suggest that recapitulating the cell-cell binding of 4-1BB effector cells (e.g. T cells, NK cells) using cellular presentation by 4-1BB-L-expressing erythroid cells is more effective in stimulating anti-tumor responses than agonist antibody-based approaches.

Cells were conjugated with 41BBL as described in Example 5. In this study, 94.7% of the cells were labelled with m4-1BB-L. The amount of molecules labelled per cell was quantified using flow cytometry. For dosing animals, there were an average of 1.1e9 m4-1BB-L mRBCs administered per dose with an average of 36,200 m4-1BB-L molecules per cell corresponding to 0.084 mg/kg m4-1BB-L per dose.

Fourteen female C57/B6 aged 6-8 weeks mice were inoculated s.c. in left flank with $5 \times 10^5$ MC-38 cells. Animals' weights and condition were recorded daily, and tumors were measured 3 times per week.

Tumors were measured three times a week by measuring each tumor in 2 dimensions. Tumor volumes were calculated using the standard formula: $(L \times W^2)/2$. The mean tumor weight and standard error of the mean was calculated for each group at each time point.

Figure 4:
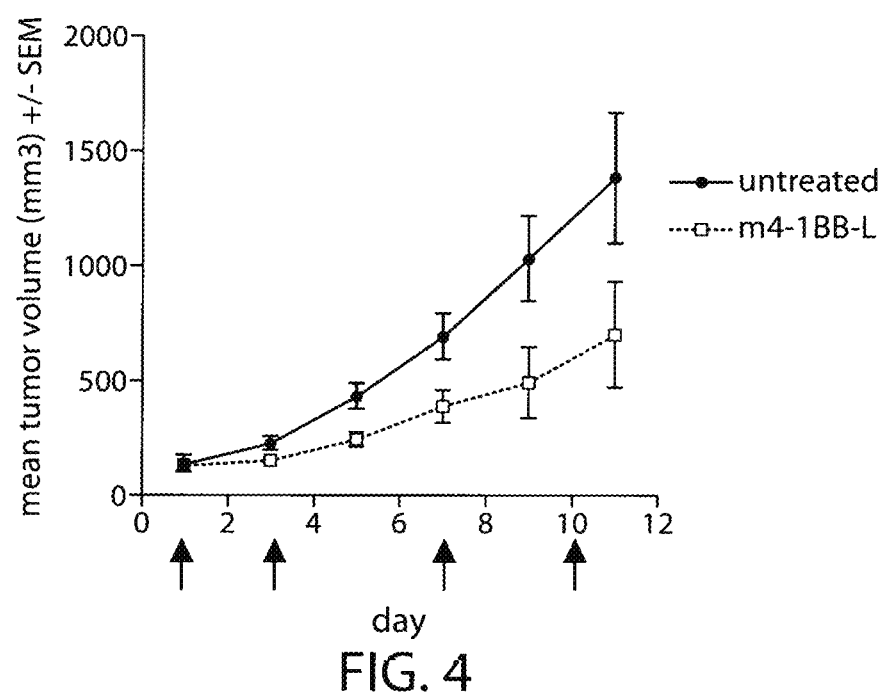
FIG. 4 is a time course showing tumor size in mice treated with 41BBL-RCT and an untreated control.

The observed anti-tumor activity of m4-1BB-L mRBC compared to untreated controls is shown in FIG. 4 and demonstrates a reduction in tumor growth in mice treated with m4-1BB-L mRBC. Tumor volume distributions demonstrated statistically significant differences between the groups as early as day 5 of the study and up until day 9 ($P<0.05$, T test).

Body weight was recorded daily. Changes in body weight were calculated for each mouse relatively to the body weight recorded on day 1. Treatment was well tolerated as indicated by overall increase in body weight for most mice. Mice that showed some decrease in body weight, did not lose more than 5% of the total body weight throughout the study.

These data support a significant efficacy and potency advantage of cellular presentation of 4-1BB-L via erythroid cells over agonistic antibody approaches. Significant anti-tumor activity was observed with m4-1BB-L mRBC in the MC38 model that was not previously seen with a 4-1BB agonist antibody dosed at a 10-fold higher level than m4-1BB-L in the same model (Chen, et al, 2014). The increased potency and activity of m4-1BB-L mRBC compared to agonist antibody approaches is consistent with 4-1BB-L cellular presentation and a corresponding 4-1BB receptor multimerization that is required to induce potent signaling via 4-1BB (Bremer, 2013) and that would normally occur within the immune synapse.

Example 11: Erythroid Cells Comprising Three Exogenous Polypeptide Agents Covalently Linked to the Cell Surface by a Residual Linker Comprising a Click Signature To test the ability to label cells with a plurality of agents, erythroid cells were functionalized with three different agents. The three agents (Factor VIIa, Factor Xa, and Cy5) were labeled with DBCO-sulfo-NHS ester (DS) or bought as DBCO labeled (i.e. Cy5). The cells were labeled with 3-Azidopropionic acid Sulfo-NHS Ester (AS). The labeled cells were the combined with the labeled agents to allow conjugation to occur. Presence of the three agents on the cells was detected by flow cytometry. The experiment indicated that 33.6% of cells were positive for all three of the agents.

Example 12: Agents Linked to Sugars

Agents can be linked directly to proteins on the cell surface, e.g., as described above. However, agents can also be linked to sugars on the cell surface, e.g., to glycan chains on glycoproteins as described in this Example. Cells having glycans at the cell surface are labeled with a bifunctional linker having one click handle and one group that reacts with a glycan.

In one approach, the click handle is added to the glycan using an adaptation of a commercially available kit developed for labeling glycans on antibodies. In this adaptation, the cells rather the antibody are first treated with endoglycosidase to hydrolyze glycans after the core GlcNAc. Then, the cells are washed and treated with an engineered galactosyl transferase, GalT(Y289L) and GalNAzide. The GalT attaches a GalNAzide residue to the exposed GlcNAc, resulting in an azide available for a biocompatible strain-promoted azide-alkyne chemistry reaction with an alkyne modified protein.

In another approach, sugar moieties within glycans are first modified to create aldehydes and ketones via a mild periodate-mediated oxidation of vicinal diols using methodology described in de Bank et al Biotechnol Bioeng 81: 800-808, 2003. An alkyne containing or azide containing click handle can then be added to the resulting aldehyde and ketone groups using alkyne hydrazide or ethymyl hydrazide, respectively. The agent can then be labeled with the corresponding azide or alkyne as described in other examples above. The labeled agent is then incubated with the labeled cells to allow conjugation to occur. Linkage of the agent to the cell can be detected by flow cytometry, e.g., as described above.

The linkage can also involve a sugar on the agent. For example, an agent (e.g., an exogenous protein or antibody) having a sugar can be labeled with a bifunctional linker having one click handle and one group that reacts with a glycan, e.g., one of the linkers described above. A cell can be labeled with a second linker, e.g., a linker that reacts with a protein or a sugar at the cell surface. The labeled cell and labeled agent are then mixed together to allow conjugation to occur. Linkage of the agent to the cell can be detected by flow cytometry, e.g., as described above.

Example 13: Measuring Immunogenicity of Functionalized Erythroid Cells

In some embodiments, functionalized erythroid cells have low immunogenicity. Immunogenicity can be tested by measurement of antibodies generated against a protein expressed on an erythroid or other cell. One standard method to measure these antibodies is using a direct ELISA. Immunogenicity against a protein or agent linked to the erythroid cell can be measured by administering the functionalized erythroid cell to an animal or patient and then obtaining plasma or serum samples over a period of days or weeks. Serial dilutions of the samples are prepared and then incubated for 10-120 minutes in ELISA plate wells that have been precoated with the protein or agent used to functionalize the erythroid cell so that any antibodies generated against the protein or agent can bind. Plates are then washed and incubated with enzyme-labeled (e.g. horseradish peroxidase) polyclonal antibodies that bind to any antibodies that have bound to protein or agent. The wells are then washed and the level of enzyme activity remaining in the well is measured to assess the level of antibodies raised against the protein or agent used to functionalize the erythroid cell.

Example 14: Functionalizing Erythroid Cells with an Erythroid Cell Cytotoxic Agent This example describes how a cell can be functionalized with a toxic agent, e.g., an agent which if expressed in the erythroid cell would be toxic to it, e.g., an agent that reduces growth rate, viability, cell life span, or function (erythroid cell cytotoxic). Cytotoxic agents include, e.g., enzymatic proteins which degrade amino acids and impair the growth and expansion of a cell, enzymes which are involved in modifying or degrading key metabolic molecules or molecular intermediates, or proteins or molecules such as ricin that interfere with critical cellular processes.

One example of an erythroid cell cytotoxic agent is asparaginase, which is used clinically to starve cancer cells. Overexpression of asparaginase in maturing erythroid cells interferes with cell growth and cellular maturation.

Cells, e.g., murine red blood cells from B6.129S7-Rag1$^{tm1Mom}$IJ (Rag1 knockout mice), are labeled in vivo by injecting mice with 2 mg of 3-azidopropionic acid sulfo-NHS ester and then harvesting cells 2 days later.

A erythroid cell cytotoxic agent, e.g., asparaginase, is labeled with 5× and 2.5× molar excess of DBCO-sulfo-NHS ester for 30 minutes at 25° C. 5× molar excess of DBCO-sulfo-NHS ester leads to ~2 labels per asparaginase monomer and 2.5× molar excess of DBCO-sulfo-NHS ester leads to ~1.2 labels per asparaginase monomer.

The labeled cells are then combined with 2 different concentrations of asparaginase-labeled DBCO to different degrees for 60 minutes to allow conjugation to occur and attain cells labeled to different degrees. Presence of the agent on the surface of the cell can be detected using an activity assay for asparaginase, using flow cytometry with an antibody against asparaginase.

TABLE 8

Asparaginase activity of labeled cells

| | Cell labeling reaction | Asparaginase activity of labeled cells |
|---|---|---|
| Higher degree of labeling | 1e9 cells + 1.6 mg asparaginase modified with ~2 labels/tetramer | 2.16e−10 units/cell |
| Lower degree of labeling | 1e9 cells + 0.2 mg asparaginase modified with ~1.2 labels/tetramer | 4.32e−11 units/cell |

The relative ability of the red blood cell conjugated asparaginase versus unconjugated asparaginase to deplete serum asparaginase over time can be tested in mice. Mice were injected with control red blood cells, RBC labeled with high or low amounts of asparaginase together, or with low, medium, or high amounts of unconjugated recombinant asparaginase as depicted in Table 9. Control and asparaginase conjugated RBCs were additionally labeled with a fluorescent tag, Cy5, to determine the pharmacokinetics of the RBCs following injection. Blood samples are then taken at various times after injection to determine the levels of asparagine and labeled RBCs levels.

TABLE 9

Set-up for injection of asparaginase-labeled cells in mice.

| | Recipient mouse | Number of animals | Description | Number of cells injected | Total units of Asparaginase injected |
|---|---|---|---|---|---|
| Group 1 | C57BL/6 | 3 | Cell not labeled with asparaginase | 1e9 | — |
| Group 2 | C57BL/6 | 3 | Cells labeled with higher dose of asparaginase | 1e9 | 0.22 |
| Group 3 | C57BL/6 | 3 | Cells labeled with lower dose of asparaginase | 1e9 | 0.043 |
| Group 4 | C57BL/6 | 3 | 2.8 ug recombinant asparaginase | — | 0.19 |
| Group 5 | C57BL/6 | 3 | 0.39 ug recombinant asparaginase | — | 0.025 |
| Group 6 | C57BL/6 | 3 | 15 ug recombinant asparaginase | — | 0.97 |
| Group 7 | B6.129S7-Rag1$^{tm1Mom}$IJ | 3 | Cell not labeled with asparaginase | 1e9 | — |
| Group 8 | B6.129S7-Rag1$^{tm1Mom}$IJ | 3 | Cells labeled with higher dose of asparaginase | 1e9 | 0.22 |
| Group 9 | B6.129S7-Rag1$^{tm1Mom}$IJ | 3 | Cells labeled with lower dose of asparaginase | 1e9 | 0.043 |
| Group 10 | B6.129S7-Rag1$^{tm1Mom}$IJ | 3 | 2.83 ug recombinant asparaginase | — | 0.19 |
| Group 11 | B6.129S7-Rag1$^{tm1Mom}$IJ | 3 | 0.385 ug recombinant asparaginase | — | 0.025 |

Figure 5:
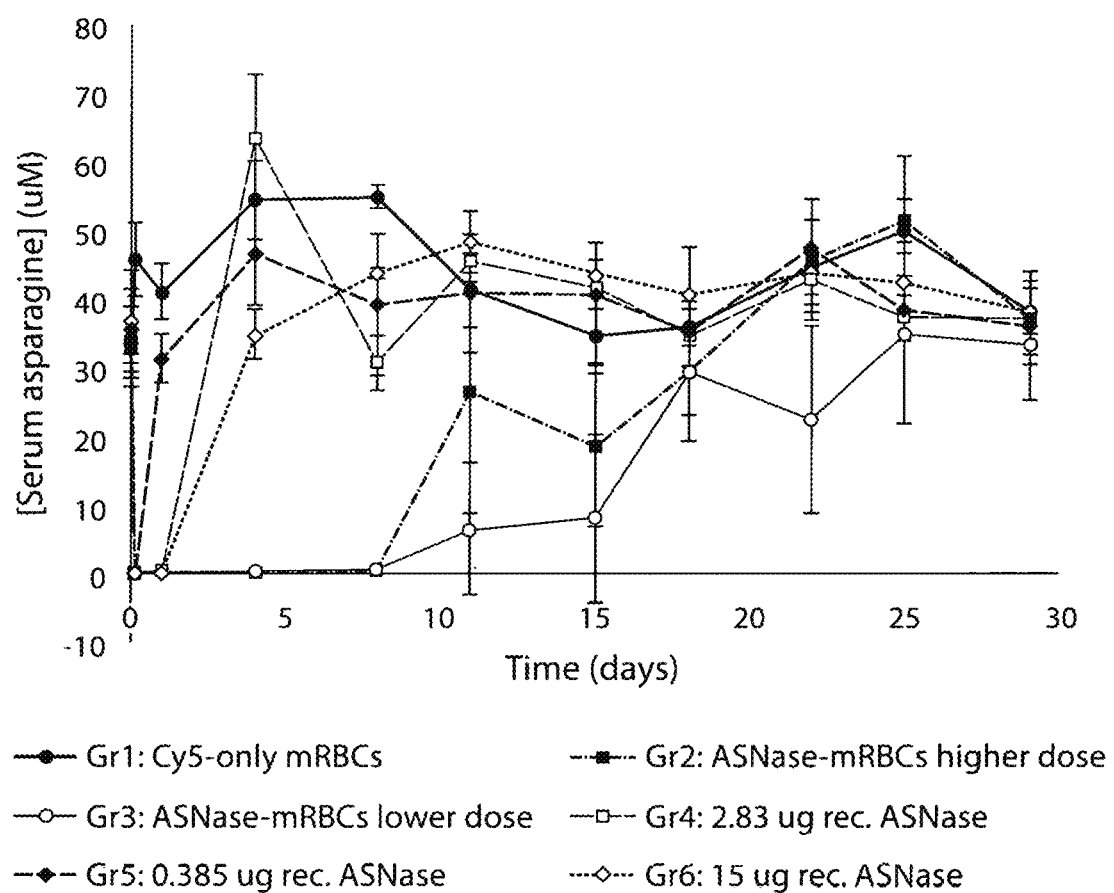
FIG. 5 is a graph showing serum asparagine levels over time in C57BL/6 mice treated with RCT-asparaginase.
Figure 6:
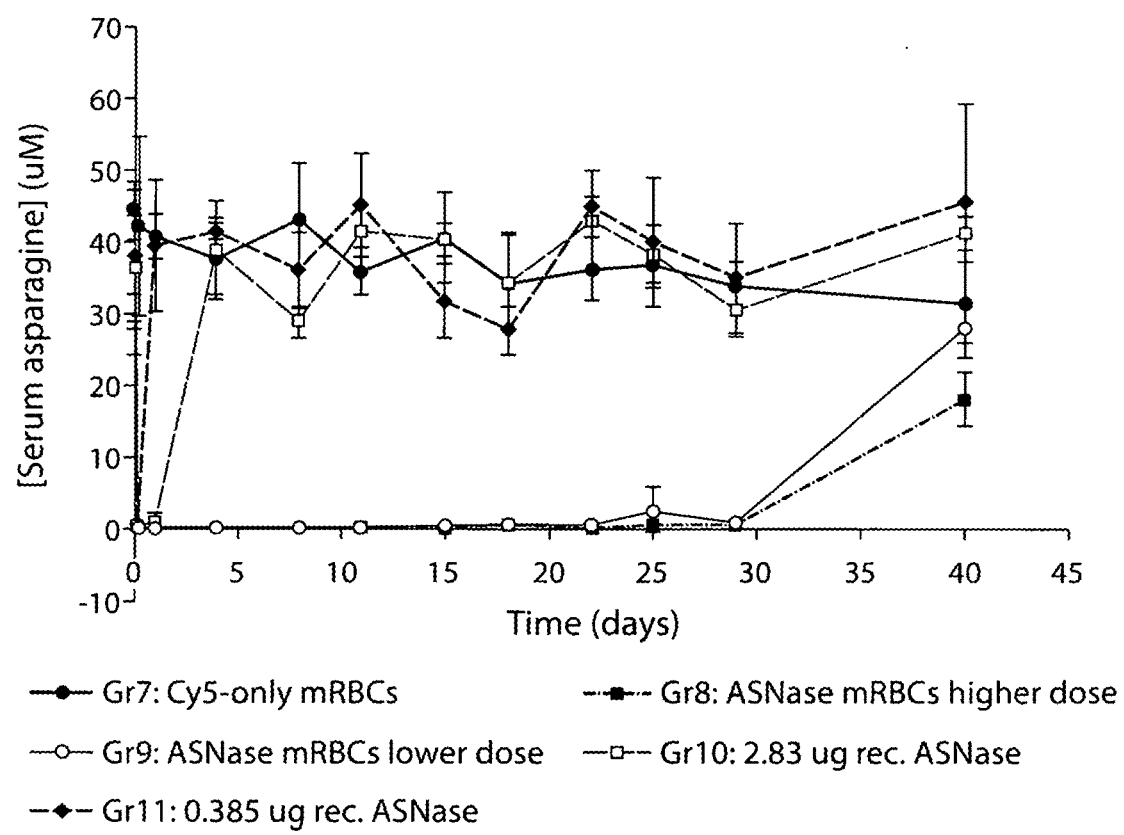
FIG. 6 is a graph showing serum asparagine levels over time in Rag1−/− mice treated with RCT-asparaginase.
Figure 7A:
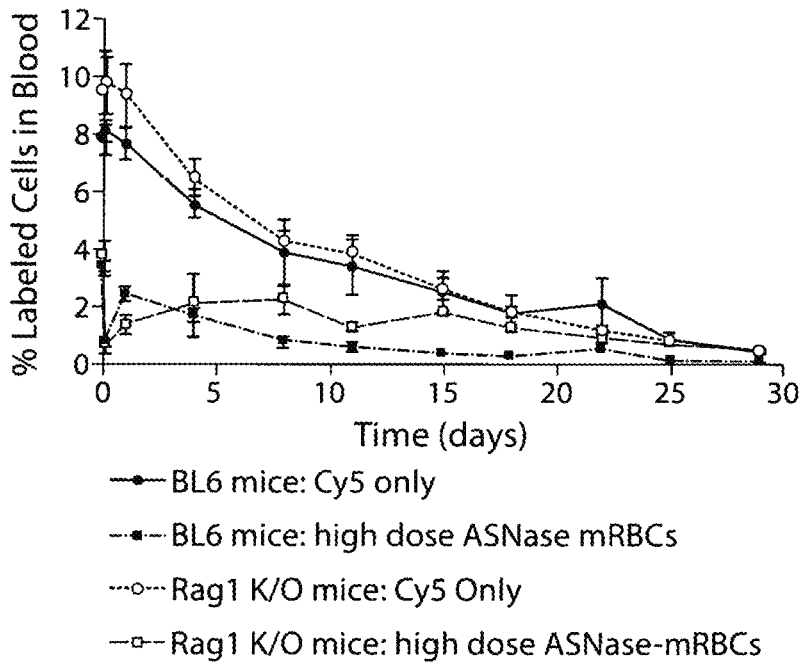
FIGS. 7A and 7B are graphs showing fluorescence over time in mice treated with Cy5-labeled RCT-asparaginase.
Figure 7B:
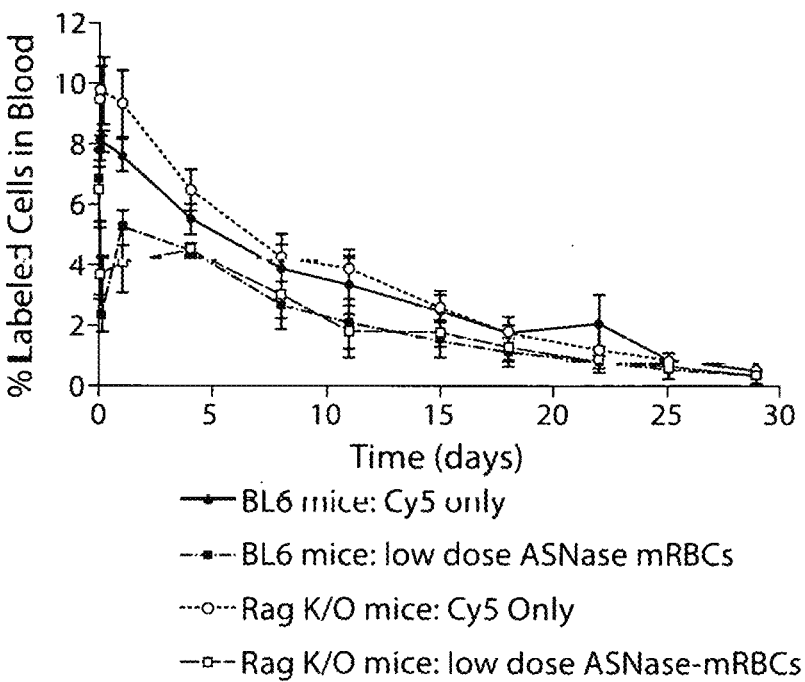

When 0.39, 2.8, or 15 micrograms of recombinant asparaginase was injected into C557BL/6 mice injected into mice, serum asparagine was reduced to near zero 6 hours after injection (FIG. 5). However, for the 0.39 ug group, serum asparagine levels rose to near normal levels by 1 day post injection, while the 2.8 and 15 ug dose groups rose near or above normal levels by day 4. In contrast, the asparagine levels were reduced to near zero from 6 hours out to 8 days in C57BL/6 mice dosed with either low or high amounts of asparaginase coupled to red blood cells with levels starting to rise again by day 11 (FIG. 5). Similar results were obtained in the Rag1 mice (FIG. 6); however, in contrast to the C57BL/6 mice, the asparagine levels remained near zero up to day 29 (FIG. 6). The pharmacokinetics of the ASNase conjugated cells is also measured by detecting the percentage of Cy5-positive cells at various times after injection using flow cytometry. One day after injection the clearance of the remaining ASNase-conjugated cells was similar to the Cy5-labeled cells (FIGS. 7A and 7B). Approximately 20% of the RBCs present in the circulation at day 1 remained in the blood by day 18. For cells with a higher level of ASNase, the initial rapid clearance of cells was larger than for the cells with lower levels of ASNase. Despite this initial rapid clearance, the cells remaining in the circulation after the first day remained detectable in the circulation to at least day 22. This experiment demonstrates that conjugating asparaginase to red blood cells dramatically improves the circulation time of asparaginase in the blood. This enhanced exposure is associated with a dramatic improvement in the ability to reduce serum asparagine levels over days and weeks with a single dose.

In addition, the pharmacokinetic profile for the asparaginase-labeled RBCs also did not change with repeated dosing, indicating a lack of immunogenic response to the asparaginase-labeled RBCs for all three levels of asparaginase, as detectable by this assay.

Example 15: Coupling of an Enzyme Agent to Erythroid Cells Via a Residual Linker Comprising a Click Signature Factor Xa (FXa) was coupled to erythroid cells. To perform the reaction, 1e9-1.36e10 cell/ml erythroid cells were labeled with 3-Azidopropionic acid Sulfo-NHS Ester (AS) and FXa was labeled with DBCO-sulfo-NHS ester (DS). The labeled cells were incubated with 0.5-1.7 mg/ml of labeled FXa, in a volume of 101 μL-3 mL, for 1 hour at 23° C. The cells were then washed with phosphate buffered saline with 0.1% bovine serum albumin, and stained with fluorescent detection reagent (anti-FXa-PE). The cells were then analyzed via flow cytometry to determine the protein clicking efficiency. Protein clicking efficiency was determined to be in the range of 99%. This experiment demonstrates the production of a population of cells having a very high labeling efficiency with an enzyme.

The number of Factor Xa protein molecules per cell was quantified by antibody binding capacity to be 1,000-250,000 molecules per cell. The number of proteins per cell can be tuned, e.g., using protein concentration, number of cells, and reaction volume, e.g., as described in Example 4.

Activity of Factor Xa was quantified by TGA activity as up to 14,000 active molecules per cell.

Example 16: Coupling of Protein Agents to Human Erythroid Cells Via a Residual Linker Comprising a Click Signature Factor Xa (FXa) and Asparaginase (ASNase) were coupled to human erythroid cells. To perform the reaction, erythroid cells were labeled with 3-Azidopropionic acid Sulfo-NHS Ester (AS) and FXa and ASNase was labeled with DBCO-PEG5-NHS ester (DP) and DBCO-sulfo-NHS ester (DS), respectively. The labeled cells were incubated with 1.03 mg/ml of labeled FXa and 4.535 mg/ml ASNase, in a volume of 10 μL, for 1 hour at 23° C. The cells were then washed with phosphate buffered saline with 0.1% bovine serum albumin, and stained with fluorescent detection reagent (anti-FX-PE and anti-ASNase-AlexaFluor 488). The cells were then analyzed via flow cytometry to determine the protein clicking efficiency. The protein clicking efficiency was determined to be in the range of 99.9% for FXa and 71.1% for ASNase. This experiment demonstrates the production of a population of human erythroid cells having a very high labeling efficiency with different proteins.

Example 17: Coupling of a Peptide Agent to Erythroid Cells Via a Residual Linker Comprising a Click Signature Biotinylated myelin oligodendrocyte glycoprotein 35-55 (MOG) peptide was coupled to erythroid cells. To perform the reaction, erythroid cells were labeled with different amounts (high and low) of 3-Azidopropionic acid Sulfo-NHS Ester (AS) and MOG peptide was labeled with DBCO-sulfo-NHS ester (DS). The labeled cells were incubated with 2.7 mg/ml of labeled MOG-DBCO, in a volume of 10 µL, for 1 hour at 23° C. The cells were then washed with phosphate buffered saline with 0.1% bovine serum albumin, and stained with fluorescent detection reagent (anti-biotin-PE). The cells were then analyzed via flow cytometry to determine the peptide clicking efficiency. The peptide clicking efficiency was determined to be in the range of 67.4% to 91.8% for MOG. This experiment demonstrates the production of a population of cells having a tunable degree of labeling efficiency with peptide. This experiment also demonstrates that a short peptide (about 20 amino acids) can be efficiently clicked onto erythroid cells.

Example 18: Coupling of a Cytokine Agent to Erythroid Cells Via a Residual Linker Comprising a Click Signature Human IL10 (hIL10) was coupled to erythroid cells. To perform the reaction, erythroid cells were labeled with 3-Azidopropionic acid Sulfo-NHS Ester (AS) and hIL10 was labeled with DBCO-sulfo-NHS ester (DS). The labeled cells were incubated with 0.24-0.79 mg/ml of labeled hIL10, in a volume of 2 µL, for 1-3 hours at 23° C. or 16 hours at 4° C. The cells were then washed with phosphate buffered saline with 0.1% bovine serum albumin, and stained with a fluorescent detection reagent (anti-hIL10-PE). The cells were then analyzed via flow cytometry to determine the protein clicking efficiency. As shown in Table 10, the protein clicking efficiency was determined to be in the range of 76.7-100%. A cell is considered positive for fluorescence if its fluorescence is greater than 99% of otherwise similar unlabeled cells. This experiment demonstrates the production of a population of cells having a very high labeling efficiency, e.g., over 200,000 molecules per cell.

TABLE 10

Efficiency of labeling cells with hIL10

| Number of cells | hIL10 concentration (mg/ml) | Click reaction time (hours) | hIL10 molecules/ cell | Percent cells positive for fluorescence |
| --- | --- | --- | --- | --- |
| 4E7 | 0.79 | 1 | 69,964 | 76.7% |
| 4E7 | 0.79 | 3 | 128,766 | 99.9% |
| 4E7 | 0.24 | 16 | 158,572 | 99.9% |
| 4E7 | 0.583 | 1 | 208,519 | 100% |

Example 19: A Cytokine Coupled to Erythroid Cells has Binding Activity

Functionalized erythroid cells having clicked proteins were tested for the ability to bind a physiological ligand. As discussed above, it is often desirable to have a high percentage of labeled cells and a high level of clicked protein per cell while preserving the protein's binding activity.

Human IL10 (hIL10) was coupled to erythroid cells as described in Example 18. The cells were then contacted with human IL10 receptor alpha Fc fusion (the cognate binding partner of hIL10), an allophycocyanin (APC)-labeled antibody that binds Fc was used to detect interaction of hIL10 clicked onto cells and its binding to human IL10 receptor alpha. Binding of the hIL10 receptor alpha to the cells indicates that not only is hIL10 present on the erythroid cells, but that its binding site is functional and oriented to permit binding. The cells were analyzed via flow cytometry to determine the protein labeling efficiency. As shown in Table 11, hIL10 binding was determined to be in the range of 90.0-95.0%. A cell is considered positive for fluorescence if its fluorescence is greater than 99% of otherwise similar unlabeled cells. This experiment demonstrates the production of cells with very high labeling efficiency yet without "over-labeling", e.g., without destroying the ligand's binding site.

TABLE 11

Binding of erythroid cell-hIL10 to hIL10 receptor alpha

| Number of cells | hIL10 degree of labeling w/ DS | Percent cells positive for fluorescence |
| --- | --- | --- |
| 5E6 | ~0.63 | 93.3% |
| 5E6 | ~1.39 | 95.0% |
| 1E7 | ~0.43 | 90.0% |

Example 20: Coupling of a Cytokine in Combination with Targeting Moiety to Erythroid Cells Human IL10 (hIL10) in combination with an anti-α4β7 Fab was coupled to erythroid cells. To perform the reaction, erythroid cells were labeled with 3-Azidopropionic acid Sulfo-NHS Ester (AS), hIL10 and anti-α4β7 Fab were individually labeled with DBCO-sulfo-NHS ester (DS). The labeled cells were incubated with 0.583 mg/ml of labeled hIL10, in a volume of 30 µL, and with 2.434 mg/ml of labeled anti-α4β7 Fab, in a volume of 19.35 µL, for 2 hours at 23° C. The cells were then washed with phosphate buffered saline with 0.1% bovine serum albumin, and stained with fluorescent detection reagents (anti-hIL10-BV421 and anti-rat kappa light chain-PE). The cells were then analyzed via flow cytometry to determine the protein clicking efficiency. The dual protein clicking efficiency was determined to be approximately 98.3%. A cell is considered positive for fluorescence if its fluorescence is greater than 99% of otherwise similar unlabeled cells. This experiment demonstrates the production of a population of cells having a very high labeling efficiency with a cytokine and a targeting moiety.

Example 21: Click Specificity

This Example demonstrates the specificity of click labeling. Three samples were assayed. First, untreated murine red blood cells (lacking a click handle) were mixed with a protein agent (anti-a4b7 Fab) having a DBCO click handle. Second, murine red blood cells having an azide click handle were mixed with an anti-a4b7 Fab that lacked a click handle. Third, murine red blood cells having an azide click handle were mixed with an anti-a4b7 Fab having a compatible DBCO click handle. The reactions were allowed to proceed for 1 hour at room temperature in PBS. The cells were then assayed for presence of the anti-a4b7 Fab by contacting them with an anti-rat IgG Kappa conjugated with PE (phycoerythrin) antibody and performing flow cytometry. A cell was considered positive for fluorescence if its signal was greater than that of 99% of untreated, otherwise similar cells in the presence of the detection reagent, but in the absence of anti-a4b7 Fab protein. As expected, the first and second samples had low fluorescence (1.81% and 1.53% of the cells fluoresced, respectively), while the third sample was highly fluorescent (95.2% of the cells fluoresced). This example demonstrates that click labeling is highly specific.

Example 22: Conjugation of a Click Handle to the N-Terminus of an Agent

It is often desirable to prevent disruption of protein biology, for example, by biasing labeling towards the N-terminus of a protein of interest, e.g., to better preserve functionality of a C-terminal domain. Proteins of interest were prepared for coupling to erythroid cells by labeling with a coupling reagent. To better preserve the functionality of human IL10, NHS ester chemistry was biased towards N-terminal labeling. Proteins were desalted, and buffer was exchanged to PBS and then concentrated to ≥1 mg/mL prior to labeling. The pH maintained at neutral pH, approximately 7-7.4.

Stock solutions of coupling reagents were prepared as described in Example 1. The coupling reagent was added at a 1-to-1 molar ratio relative to the protein concentration. The protein labeling reaction was incubated at room temperature for 1 hour to 1 hour and 30 minutes, with gentle agitation every 10 minutes. In order to detect the level of labeling, the Nanodrop UV-Vis program was used to read approximately 1-3 µL of labeled protein at absorbance 280 nm and 309 nm with a baseline correction at 750 nm. Degree of labeling ranged from 0.63-1.39 DBCO click handle molecules per protein.

Example 23: Conjugation of a Click Handle to an Agent Comprising a Free Cysteine Residue, e.g., Situated in a π-Clamp, Using Maleimide Chemistry It can be desirable to better preserve protein biology, for example, by introducing a free cysteine into a protein of interest for site specific maleimide chemistry conjugation. Proteins of interest (e.g., mouse 41BBL) were prepared for coupling to erythroid cells by labeling with a coupling reagent. To better preserve the protein functionality, a free cysteine was introduced into the recombinant 41BBL protein in the four amino acid sequence (FCPF, SEQ ID NO: 64) known as a "π-clamp" for site specific maleimide chemistry conjugation. Although a π-clamp is used in this example, it is contemplated that any free cysteine residue may be used for site specific conjugation, e.g., as described herein. Proteins were desalted, buffer exchanged to PBS, and concentrated to ≥1 mg/mL prior to labeling. Proteins were reduced with 1 mM DTT, incubated for 1 hour at room temperature, and desalted on a NAP5 column.

The maleimide coupling reagent was added at a 5 fold molar excess relative to the protein concentration. The protein labeling reaction was incubated at room temperature for 4 hours and desalted using a NAP10 column. In order to detect the level of labeling, the Nanodrop UV-Vis program was used to read approximately 1-31 µL of labeled protein at absorbance 280 nm and 309 nm with a baseline correction at 750 nm. Degree of labeling ranged from 6-7.6 DBCO click handle molecules per protein.

Example 24: Conjugation of a Click Handle to an Agent Comprising Two Cysteine Residues, Using ThioLinker Chemistry It can be desirable to introduce a click handle at a specific site in a protein of interest and/or in a particular orientation. Proteins of interest were prepared for coupling to erythroid cells by labeling with a coupling reagent. In one method, ThioLinker chemistry was introduced to recombinant anti-CTLA4 Fab protein for site specific click handle conjugation through bridging a disulfide bond. Fabs were desalted, buffer exchanged to PBS, and concentrated to ≥1 mg/mL prior to labeling. Fabs were then reduced with 5 mM DTT, incubated for 1 hour at 37° C., and then buffer exchanged into PBS. The ThioLinker coupling reagent was added at a 15 fold molar excess relative to the protein concentration to label the reduced disulfide bond. The protein labeling reaction was incubated at 4° C. for 16-18 hours and desalted using a Zeba column. In order to detect the level of labeling, the Nanodrop UV-Vis program was used to read approximately 1-3 µL of labeled protein at absorbance 280 nm and 309 nm with a baseline correction at 750 nm. Degree of labeling was 8.3 DBCO click handle molecules per protein. ThioLinker oriented click handle labeling on anti-CTLA-4 Fab was compared to other click handle reagents and found to result in substantial labeling of cells. ThioLinker-labeled anti-CTLA-4 was also found to significantly increase functional binding to recombinant CTLA4.

Figure 8A:
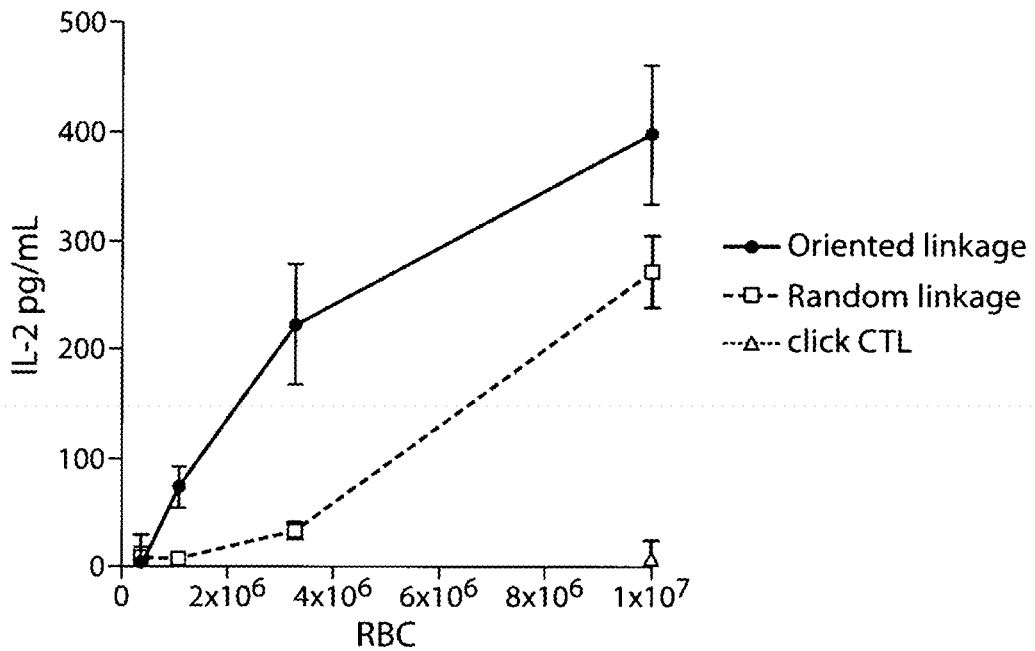
FIGS. 8A and 8B are graphs showing the oriented labeling of HIS6 mouse 41BBL using a ThioLinker click handle results in increased functional activity of coupled cells.
Figure 8B:
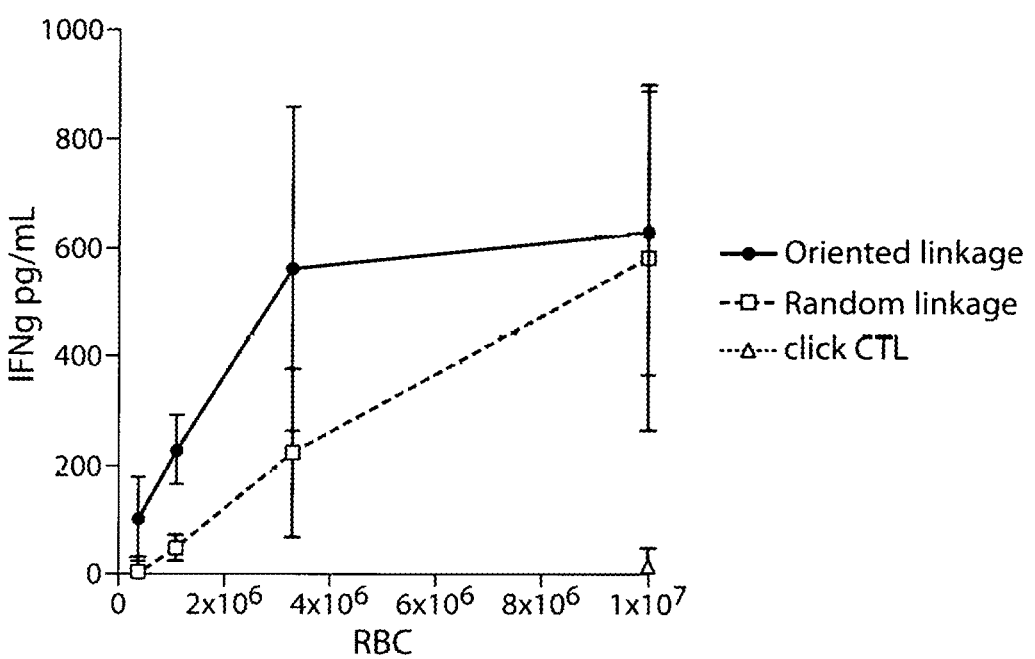

In another method, ThioLinker chemistry was used to site specifically label a recombinant protein (HIS6 mouse 41BBL) through the HIS6 purification tag. Proteins were typically desalted, buffer exchanged to PBS, and concentrated to ≥1 mg/mL prior to labeling. The ThioLinker coupling reagent was then added at a 20 fold molar excess relative to the protein concentration to label the HIS6 tag of the protein (non-reduced). The protein labeling reaction was incubated at room temperature for 3 hours and buffer exchanged to PBS using a Zeba desalting column. ThioLinker labeling of HIS6 mouse 41BBL clicked onto AS-labeled RBC resulted in increased functional ability for 41BBL-clicked cells to activate immune cells, as shown by IL-2 production (FIG. 8A) and interferon-γ (IFN-γ) production (FIG. 8B), respectively. It was observed that oriented linkage of HIS6 mouse 41BBL resulted in substantially greater IL-2 and IFN-γ secretion compared to random linkage, although the latter induced significantly greater cytokine secretion than click CTL control (AS-labeled RBCs only).

Example 25: Production of an Agent Comprising a Non-Canonical Amino Acid (ncAA)

Figure 9A:
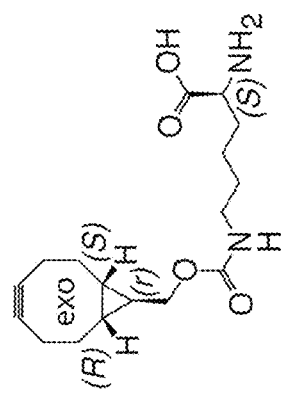
FIGS. 9A and 9B show site-specific incorporation of a non-canonical amino acid, exo(BCN)-lysine, into mouse 41BBL, to create a clickable mouse 41BBL.

It can be desirable to introduce a coupling reagent at a specific site of interest within a protein of interest, for example, by incorporating non-canonical amino acids (ncAA) into a protein of interest in a site-specific manner. In this example, proteins of interest were produced through co-transfection of Expi293 cells with a plasmid containing a tRNA/amino-acyl-tRNA synthase pair and a plasmid encoding the protein of interest (mIg-mouse 41BBL) with an amber stop codon (TAG) incorporated at a site of interest. Cells were plated and plasmids were transfected at 1.5 µg/mL of each plasmid using the ExpiFectamine kit on day 1. Different concentrations (2 mM, 1.3 mM, 1 mM, 250 µM)

of ncAA (Exo(BCN)-Lys; FIG. 9A) were added to the transfected cells for site specific incorporation in place of the amber stop codon the same day. At day 3 after transfection, media was harvested to obtain secreted proteins. Secreted proteins were confirmed to have site specific ncAA incorporation through incubation with Azide-Biotin Cy5 for 30 min at room temperature and then western blot analysis. Proteins were detected with an anti-41BBL antibody and a secondary HRP antibody, and click handle incorporation was detected with an anti-biotin-HRP antibody.

TABLE 12

| Proteins clicked | |
| --- | --- |
| Protein | Labeling chemistry |
| Ovalbumin | DBCO-Sulfo-NHS ester |
| Erwinase (Erwinia asparaginase) | DBCO-Sulfo-NHS ester |
| Uricase | DBCO-Sulfo-NHS ester |
| Lysozyme | DBCO-Sulfo-NHS ester |
| Anti-CTLA4 Fab | ThioLinker-DBCO |
| Anti-CD3 Fab | ThioLinker-DBCO |
| Anti-PDL1 Fab | ThioLinker-DBCO |

Figure 9B:
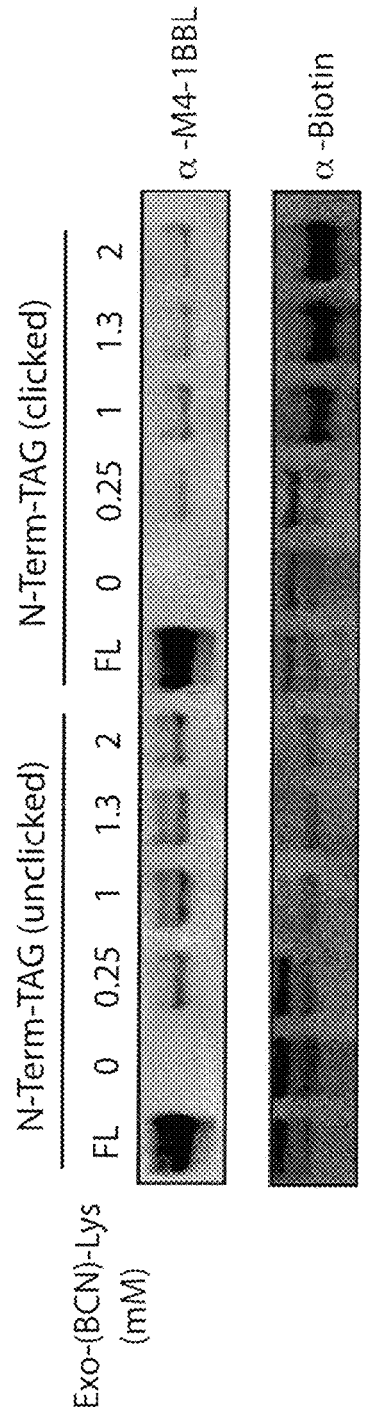

As shown in FIG. 9B, site-specific incorporation of the ncAA exo(BCN)-lysine resulted in the production of clickable murine 41BBL.

Example 26: Coupling of Urate Oxidase to Erythroid Cells Via a Linker Having a Click Signature Recombinant *Candida utilis* His$_6$-urate oxidase was expressed and purified from *E. coli* and labeled with DBCO-sulfo-NHS ester yielding urate oxidase at a ratio of approximately 1 label per monomer. Murine red blood cells (RBCs) were labeled with 6-Azidohexanoic Acid Sulfo-NHS ester. Coupling reactions were performed in which 1e9 labeled murine RBCs were incubated in the presence of either 0 uM or 75 uM DBCO-labeled urate oxidase for 2 hours at room temperature. The degree of urate oxidase conjugation was evaluated by staining the murine RBCs for His$_6$-urate oxidase with DyLight 488-labeled anti-His$_6$ antibody, followed by flow cytometry analysis. 100% of the RBCs incubated with 75 uM urate oxidase were labeled with the enzyme; in contrast only 0.16% of negative control cells treated with 0 uM urate oxidase showed positive fluorescence in this assay.

The RBCs coupled to urate oxidase were able to efficiently deplete uric acid, showing a urate oxidase activity of about 4.6e−12 units/cell.

Example 27: Erythroid Cells Comprising Exogenous Polypeptide Agent are Active In Vivo Enucleated erythroid cells were conjugated with anti-PD-L1 at their surface and tested for the ability to infiltrate tumors in mice.

Mice were inoculated with B16F10 cells SC. Tumors were allowed to grow to 400 cubic mm before dosing. Murine RBC were conjugated with fragments antibody (Fab) from anti murine PD-L1 and isotype control. Conjugated murine RBC were labeled with CTFR according to the manufacturer's protocol. Cells were infused into the animals. One day after infusion, tumors were collected. Tumors were sectioned and stained with anti CD31 to visualize tumor vasculature and DAPI to visualize nuclei. Stained sections were scanned and pictures were taken. Using Halo software, the tumor areas and vasculature areas were identified. Total cell counts of labeled RBC in these two areas were taken for both isotype control and anti-PD-L1. The ratio between the RBC found in the tumor and the RBC found in the vessels was calculated. The ratio between RBC in the vessels and RBC in the tumor is 1 (average of measurement in tumors from 8 mice) for the isotype control conjugated RBC, indicating similar amounts in the tumor and the vasculature. The ratio between RBC in the vessel and RBC in the tumor is 1.7 for the anti PD-L1 treated mice, indicating enrichment of RBC in the tumor in the anti-PD-L1 group in comparison with the isotype control mice. The difference in ratio between the 2 groups was statistically significant with P<0.01 (student T test).

While not wishing to be bound by theory, tumors expressing higher levels of PD-L1 may respond better to RCTs comprising anti-PD-L1 than tumors that express lower levels of PD-L1. The B16F10 cells expressed about 300,000 copies per cell of PD-L1 when stimulated with IFN-gamma at 10 ng/ul. In contrast, CT26 cells expressed about 150,000 copies per cell of PD-L1 and A20 cells expressed about 100,000 copies per cell of PD-L1 under the same conditions. PD-L1 copy number was measured using a Quantum Simply Cellular kit (Bangs Laboratories). Erythroid cells comprising an anti-PD-L1 antibody at their surface showed greater binding to the IFN-gamma treated B16F10 cells and CT26 than to the A20 cells, consistent with greater levels of PD-L1 expression on the tumor cells leading to increased binding of the erythroid cells to the tumor cells.

What is claimed is:

1. A method of making an enucleated erythroid cell functionalized with an exogenous polypeptide, the method comprising:
   (a) providing an activated cell comprising an enucleated erythroid cell covalently bound to a first click handle, wherein the activated cell was made using a process that does not comprise contacting an enucleated erythroid cell or a precursor thereof with a sugar comprising the first click handle,
   (b) providing an activated agent comprising the exogenous polypeptide covalently bound to a second click handle capable of reacting with the first click handle, and
   (c) contacting the activated cell with the activated agent, thereby producing the enucleated erythroid cell functionalized with the exogenous polypeptide,
   wherein one or both of the activated cell and the enucleated erythroid cell functionalized with the exogenous polypeptide lack(s) a sortase transfer signature; and
   wherein reaction between the first click handle and the second click handle in step (c) does not require a copper ion catalyst.

2. The method of claim 1, wherein the exogenous polypeptide is greater than about 30 kilodaltons.

3. The method of claim 1, wherein the exogenous polypeptide is greater than about 500 amino acids in length.

4. The method of claim 1, wherein the process results in covalent linking of the activated agent to an amino acid side chain of an endogenous protein at the surface of the enucleated erythroid cell functionalized with the exogenous polypeptide.

5. The method of claim 1, wherein the method further comprises contacting an enucleated erythroid cell with a first coupling reagent comprising the first click handle, thereby producing the activated cell.

6. The method of claim 5, wherein the method further comprises:
   (d) contacting the activated cell with a second coupling reagent comprising a third click handle, and
   (e) contacting the activated cell with a second activated agent comprising a second exogenous polypeptide covalently bound to a fourth click handle capable of reacting with the third click handle.

7. The method of claim 5, wherein the first click handle comprises an azide or an alkyne.

8. The method of claim 7, wherein the first click handle is an azide, and wherein the azide comprises 3-azidopropionic acid sulfo-NHS ester or 6-azidohexanoic acid sulfo-NHS ester.

9. The method of claim 7, wherein the first click handle is an alkyne, and wherein the alkyne comprises DBCO-sulfo-NHS ester or DBCO-PEG-NHS ester.

10. The method of claim 9, wherein the alkyne comprises DBCO-PEG-NHS ester, and the DBCO-PEG-NHS ester is either DBCO-PEG4-NHS ester or DBCO-PEG5-NHS ester.

11. The method of claim 5, wherein the first coupling reagent comprises a linker.

12. The method of claim 1, wherein the method further comprises contacting the activated cell with an activated agent comprising a second exogenous polypeptide covalently bound to the second click handle capable of reacting with the first click handle.

13. The method of claim 1, wherein the enucleated erythroid cell functionalized with the exogenous polypeptide comprises at least 5,000 copies of the exogenous polypeptide.

14. The method of claim 1, wherein the method further comprises contacting the exogenous polypeptide with a second coupling reagent comprising the second click handle, thereby producing the activated agent.

15. The method of claim 14, wherein the second click handle comprises an azide or an alkyne.

16. The method of claim 15, wherein the second click handle is an azide, and wherein the azide comprises 3-azidopropionic acid sulfo-NHS ester or 6-azidohexanoic acid sulfo-NHS ester.

17. The method of claim 15, wherein the second click handle comprises an alkyne, and wherein the alkyne comprises DBCO-sulfo-NHS ester or DBCO-PEG-NHS ester.

18. The method of claim 17, wherein the alkyne comprises DBCO-PEG-NHS ester, and the DBCO-PEG-NHS ester is either DBCO-PEG4-NHS ester or DBCO-PEG5-NHS ester.

19. The method of claim 14, wherein the second coupling reagent comprises a linker.

20. The method of claim 1, wherein the exogenous polypeptide comprises an enzyme, an antigen, an antibody, an antibody-like molecule, a growth factor, a transporter, a cytokine, a chemokine, a growth factor receptor, a cytokine receptor, a chemokine receptor, a DNA binding protein, or an RNA binding protein.

21. The method of claim 1, wherein the activated cell lacks a sortase transfer signature.

22. The method of claim 1, wherein the enucleated erythroid cell functionalized with the exogenous polypeptide lacks a sortase transfer signature.

23. The method of claim 1, wherein both of the activated cell and the enucleated erythroid cell functionalized with the exogenous polypeptide lack a sortase transfer signature.

24. The method of claim 1, wherein the method does not comprise a sortagging step.

25. A method of making an enucleated erythroid cell functionalized with an exogenous polypeptide, the method comprising:
  (a) providing an activated cell comprising an enucleated erythroid cell covalently bound to a first click handle, wherein the activated cell was made using a process that does not comprise contacting an enucleated erythroid cell or a precursor thereof with a sugar comprising the first click handle,
  (b) providing an activated agent comprising the exogenous polypeptide covalently bound to a second click handle capable of reacting with the first click handle, and
  (c) contacting the activated cell with the activated agent, thereby producing the enucleated erythroid cell functionalized with the exogenous polypeptide,
  wherein one or both of the activated cell and the enucleated erythroid cell functionalized with the exogenous polypeptide lack(s) a sortase transfer signature, and wherein:
  (i) the first click handle comprises a cyclooctyne and the second click handle comprises and azide;
  (ii) the first click handle comprises an azide and the second click handle comprises a cyclooctyne;
  (iii) the first click handle comprises a transcycloalkene and the second click handle comprises a tetrazine; or
  (iv) the first click handle comprises a tetrazine and the second click handle comprises a transcycloalkene.

26. The method of claim 25, wherein the exogenous polypeptide is greater than about 30 kilodaltons.

27. The method of claim 25, wherein the exogenous polypeptide is greater than about 500 amino acids in length.

28. The method of claim 25, wherein the process results in covalent linking of the activated agent to an amino acid side chain of an endogenous protein at the surface of the enucleated erythroid cell functionalized with the exogenous polypeptide.

29. The method of claim 25, wherein the method further comprises contacting an enucleated erythroid cell with a first coupling reagent comprising the first click handle, thereby producing the activated cell.

30. The method of claim 29, wherein the first coupling reagent comprises a linker.

31. The method of claim 25, wherein the method further comprises contacting the activated cell with an activated agent comprising a second exogenous polypeptide covalently bound to the second click handle capable of reacting with the first click handle.

32. The method of claim 29, wherein the method further comprises:
  (d) contacting the activated cell with a second coupling reagent comprising a third click handle, and
  (e) contacting the activated cell with a second activated agent comprising a second exogenous polypeptide covalently bound to a fourth click handle capable of reacting with the third click handle.

33. The method of claim 25, wherein the enucleated erythroid cell functionalized with the exogenous polypeptide comprises at least 5,000 copies of the exogenous polypeptide.

34. The method of claim 25, wherein the method further comprises contacting the exogenous polypeptide with a second coupling reagent comprising the second click handle, thereby producing the activated agent.

35. The method of claim 34, wherein the second coupling reagent comprises a linker.

36. The method of claim 25, wherein the exogenous polypeptide comprises an enzyme, an antigen, an antibody, an antibody-like molecule, a growth factor, a transporter, a cytokine, a chemokine, a growth factor receptor, a cytokine receptor, a chemokine receptor, a DNA binding protein, or an RNA binding protein.

37. The method of claim 25, wherein the activated cell lacks a sortase transfer signature.

38. The method of claim 25, wherein the enucleated erythroid cell functionalized with the exogenous polypeptide lacks a sortase transfer signature.

39. The method of claim 25, wherein both of the activated cell and the enucleated erythroid cell functionalized with the exogenous polypeptide lack a sortase transfer signature.

40. The method of claim 25, wherein the method does not comprise a sortagging step.

41. The method of claim 25, wherein the first click handle comprises a cyclooctyne and the second click handle comprises and azide.

42. The method of claim 25, wherein the first click handle comprises an azide and the second click handle comprises a cyclooctyne.

43. The method of claim 25, wherein the first click handle comprises a transcycloalkene and the second click handle comprises a tetrazine.

44. The method of claim 25, wherein the first click handle comprises a tetrazine and the second click handle comprises a transcycloalkene.

* * * * *